(12) United States Patent
Freedman, Jr. et al.

(10) Patent No.: US 7,666,213 B2
(45) Date of Patent: Feb. 23, 2010

(54) APPARATUS FOR ALTERING THE BODY TEMPERATURE OF A PATIENT

(75) Inventors: Robert J. Freedman, Jr., Alexandria, LA (US); Robert B. Schock, Sparta, NJ (US); Marc Cote, Cornwall, NY (US); William J. Ohley, Wakefield, RI (US)

(73) Assignee: Life Recovery Systems HD, LLC, Alexandria, LA (US)

( * ) Notice: Subject to any disclaimer, the term of this patent is extended or adjusted under 35 U.S.C. 154(b) by 699 days.

(21) Appl. No.: 10/950,152

(22) Filed: Sep. 24, 2004

(65) Prior Publication Data

US 2005/0096714 A1    May 5, 2005

Related U.S. Application Data

(63) Continuation-in-part of application No. 10/193,635, filed on Jul. 11, 2002, now Pat. No. 6,969,399.

(51) Int. Cl.
*A61F 7/00* (2006.01)
(52) U.S. Cl. .......................................... 607/104; 4/585
(58) Field of Classification Search ......... 607/104–112, 607/96; 4/515, 518, 585, 584
See application file for complete search history.

(56) References Cited

U.S. PATENT DOCUMENTS

| | | |
|---|---|---|
| 26,663 A | 1/1860 | French |
| 998,804 A | 7/1911 | Salisbury |
| 1,936,960 A | 11/1933 | Bowman |
| 2,043,721 A | 6/1936 | Warwick |
| 2,093,834 A | 9/1937 | Gaugler |

(Continued)

FOREIGN PATENT DOCUMENTS

GB    1095988    12/1967

(Continued)

OTHER PUBLICATIONS

Author Unknown, "Enhanced External Counterpulsation (EECP)", date unknown, p. 130.

(Continued)

*Primary Examiner*—Roy D Gibson
(74) *Attorney, Agent, or Firm*—Armstrong Teasdale, LLP

(57) ABSTRACT

An apparatus for adjusting the body temperature of a patient comprises an enclosure defining an interior space for receiving at least a portion of a patient's body therein. The enclosure is adapted for substantially sealingly enclosing the portion of the patient's body within the interior space with the enclosure. Heat transfer liquid may then be circulated through the interior space of the enclosure via an inlet and an outlet for flow over the patient's body in direct liquid contact therewith to promote heat transfer between the patient's body and said heat transfer liquid. The heat transfer liquid may be either warmer or cooler than the patient's body temperature, to either warm or cool the portion. Controlled cooling may be employed to induce therapeutic hypothermia, while controlled warming may be employed to counteract unintended hypothermia. The apparatus further comprises a portable control unit that includes a liquid delivery system, a power source, a control system and a user interface for powering and controlling the liquid delivery system.

72 Claims, 29 Drawing Sheets

U.S. PATENT DOCUMENTS

| | | | |
|---|---|---|---|
| 2,224,876 A | 12/1940 | Matys | |
| 2,272,481 A * | 2/1942 | Rinkcs et al. | 601/166 |
| 2,416,788 A | 3/1947 | Andrews | |
| 2,471,302 A | 5/1949 | Nellie | |
| 2,493,067 A | 1/1950 | Goldsmith | |
| 2,566,600 A | 9/1951 | Colon | |
| 2,702,552 A | 2/1955 | Moodie | |
| 2,832,336 A | 4/1958 | Davis et al. | |
| 3,051,180 A | 8/1962 | Adams-Ray et al. | |
| 3,266,064 A | 8/1966 | Figman | |
| 3,477,424 A | 11/1969 | Tracy | |
| 3,587,577 A | 6/1971 | Smirnov et al. | |
| 3,670,347 A | 6/1972 | Weinstein | |
| 3,757,362 A | 9/1973 | Bowlin et al. | |
| 3,866,994 A * | 2/1975 | Bonin | 312/236 |
| 4,057,861 A | 11/1977 | Howorth | |
| 4,068,326 A | 1/1978 | Deschler | |
| 4,074,369 A | 2/1978 | Harmon | |
| 4,139,004 A | 2/1979 | Gonzalez | |
| 4,141,585 A | 2/1979 | Blackman | |
| 4,149,529 A | 4/1979 | Copeland et al. | |
| 4,191,028 A * | 3/1980 | Audet et al. | 62/259.1 |
| 4,300,547 A | 11/1981 | Pasternack | |
| 4,353,359 A | 10/1982 | Milbauer | |
| 4,376,437 A | 3/1983 | Sundheim et al. | |
| 4,442,838 A | 4/1984 | Samson et al. | |
| 4,572,188 A | 2/1986 | Augustine et al. | |
| 4,586,500 A | 5/1986 | Glynn | |
| 4,648,392 A | 3/1987 | Cartier et al. | |
| 4,691,762 A | 9/1987 | Elkins et al. | |
| 4,738,119 A | 4/1988 | Zafred | |
| 4,747,408 A | 5/1988 | Chuan-Chih | |
| 4,765,338 A | 8/1988 | Turner et al. | |
| D300,194 S | 3/1989 | Walker | |
| 4,858,259 A | 8/1989 | Simmons et al. | |
| 4,865,012 A | 9/1989 | Kelley | |
| 4,935,971 A | 6/1990 | Dunn et al. | |
| 4,945,901 A | 8/1990 | Burcke, Jr. | |
| 4,959,877 A | 10/1990 | Covil | |
| 4,962,761 A | 10/1990 | Golden | |
| 4,987,618 A | 1/1991 | Tolbert | |
| 4,987,896 A | 1/1991 | Nakamatsu | |
| 5,016,304 A | 5/1991 | Ryhiner | |
| 5,025,515 A * | 6/1991 | Rhines | 4/585 |
| 5,033,136 A | 7/1991 | Elkins | |
| 5,063,924 A | 11/1991 | Galvan et al. | |
| 5,074,285 A | 12/1991 | Wright | |
| 5,146,625 A | 9/1992 | Steele et al. | |
| 5,149,331 A | 9/1992 | Ferdman et al. | |
| 5,172,689 A | 12/1992 | Wright | |
| 5,235,709 A * | 8/1993 | Terlep | 4/515 |
| 5,241,958 A | 9/1993 | Noeldner | |
| 5,243,706 A | 9/1993 | Frim et al. | |
| 5,246,061 A * | 9/1993 | Zalite | 165/10 |
| 5,249,318 A | 10/1993 | Loadsman | |
| 5,257,429 A | 11/1993 | Genis | |
| 5,265,599 A | 11/1993 | Stephenson et al. | |
| 5,292,347 A | 3/1994 | Pompei | |
| 5,295,949 A | 3/1994 | Hathaway | |
| 5,300,100 A | 4/1994 | Hickle et al. | |
| 5,305,471 A | 4/1994 | Steele et al. | |
| 5,305,542 A | 4/1994 | Phelps | |
| D347,491 S | 5/1994 | Holloway | |
| 5,330,519 A | 7/1994 | Mason et al. | |
| 5,336,250 A | 8/1994 | Augustine | |
| 5,342,411 A | 8/1994 | Maxted et al. | |
| 5,350,417 A | 9/1994 | Augustine | |
| 5,351,345 A | 10/1994 | Sills et al. | |
| 5,358,467 A | 10/1994 | Milstein et al. | |
| 5,383,918 A | 1/1995 | Panetta | |
| 5,405,370 A | 4/1995 | Irani | |
| 5,411,494 A | 5/1995 | Rodriguez | |
| 5,416,935 A | 5/1995 | Nieh | |
| D360,692 S | 7/1995 | Gambino | |
| 5,441,477 A | 8/1995 | Hargest | |
| 5,447,504 A | 9/1995 | Baker | |
| D365,378 S | 12/1995 | Wolfe | |
| D366,084 S | 1/1996 | Wolfe | |
| 5,490,820 A | 2/1996 | Schock et al. | |
| 5,496,357 A | 3/1996 | Jensen et al. | |
| 5,507,792 A | 4/1996 | Mason et al. | |
| 5,584,084 A | 12/1996 | Klearman et al. | |
| 5,603,728 A | 2/1997 | Pachys | |
| 5,603,729 A | 2/1997 | Brown et al. | |
| 5,642,539 A | 7/1997 | Kuo | |
| D383,834 S | 9/1997 | Frankel | |
| 5,683,438 A | 11/1997 | Grahn | |
| 5,688,225 A | 11/1997 | Walker | |
| 5,722,482 A | 3/1998 | Buckley | |
| 5,755,756 A | 5/1998 | Freedman, Jr. et al. | |
| 5,800,480 A | 9/1998 | Augustine et al. | |
| 5,814,009 A | 9/1998 | Wheatman | |
| 5,817,147 A | 10/1998 | Wolf | |
| D405,291 S | 2/1999 | Yu | |
| 5,871,526 A | 2/1999 | Gibbs et al. | |
| 5,879,316 A | 3/1999 | Safar et al. | |
| 5,887,304 A | 3/1999 | von der Heyde | |
| D410,084 S | 5/1999 | Tumey | |
| 5,906,588 A | 5/1999 | Safar et al. | |
| 5,913,885 A | 6/1999 | Klatz et al. | |
| 5,913,886 A | 6/1999 | Soloman | |
| 5,927,273 A | 7/1999 | Federowicz et al. | |
| 5,948,012 A | 9/1999 | Mahaffey et al. | |
| 5,950,234 A | 9/1999 | Leong et al. | |
| 5,957,964 A | 9/1999 | Ceravolo | |
| 5,975,081 A | 11/1999 | Hood et al. | |
| 5,980,561 A | 11/1999 | Kolen et al. | |
| 5,989,285 A | 11/1999 | DeVilbiss et al. | |
| 5,991,948 A | 11/1999 | Stanley et al. | |
| 6,030,412 A | 2/2000 | Klatz et al. | |
| 6,052,853 A | 4/2000 | Schmid | |
| 6,079,070 A | 6/2000 | Flick | |
| 6,086,609 A * | 7/2000 | Buckley | 607/104 |
| 6,109,338 A | 8/2000 | Butzer | |
| 6,109,895 A | 8/2000 | Ray et al. | |
| 6,128,795 A | 10/2000 | Stanley et al. | |
| D433,508 S | 11/2000 | Crowther | |
| 6,149,674 A | 11/2000 | Borders | |
| 6,165,208 A | 12/2000 | Reyes et al. | |
| D436,175 S | 1/2001 | Tumey | |
| 6,182,316 B1 | 2/2001 | Thomas et al. | |
| 6,183,855 B1 | 2/2001 | Buckley | |
| 6,188,930 B1 | 2/2001 | Carson | |
| D438,623 S | 3/2001 | Tantau | |
| 6,197,045 B1 | 3/2001 | Carson | |
| 6,210,427 B1 | 4/2001 | Augustine et al. | |
| 6,228,106 B1 | 5/2001 | Simbruner et al. | |
| 6,238,427 B1 | 5/2001 | Matta | |
| 6,245,094 B1 | 6/2001 | Pompei | |
| 6,276,155 B2 | 8/2001 | Siman-Tov et al. | |
| 6,277,144 B1 | 8/2001 | Tomic-Edgar et al. | |
| 6,336,231 B1 | 1/2002 | Smith | |
| 6,352,550 B1 | 3/2002 | Gildersleeve et al. | |
| 6,375,674 B1 | 4/2002 | Carson | |
| D461,900 S | 8/2002 | Siepmann | |
| 6,461,379 B1 | 10/2002 | Carson et al. | |
| 6,508,831 B1 | 1/2003 | Kushnir | |
| 6,517,510 B1 | 2/2003 | Stewart et al. | |
| 6,520,982 B1 | 2/2003 | Boynton et al. | |
| D471,987 S | 3/2003 | Hoglund et al. | |
| D472,322 S | 3/2003 | Hoglund et al. | |
| 6,551,347 B1 | 4/2003 | Elkins | |
| D474,061 S | 5/2003 | Cook | |
| D474,544 S | 5/2003 | Hoglund et al. | |

| | | | |
|---|---|---|---|
| 6,565,593 | B2 | 5/2003 | Diana |
| 6,585,709 | B2 * | 7/2003 | Maimets ..................... 604/355 |
| 6,602,277 | B2 | 8/2003 | Grahn et al. |
| 6,620,187 | B2 | 9/2003 | Carson et al. |
| 6,645,232 | B2 | 11/2003 | Carson |
| 6,648,905 | B2 | 11/2003 | Hoglund et al. |
| D483,125 | S | 12/2003 | Hoglund et al. |
| 6,656,208 | B2 | 12/2003 | Grahn et al. |
| 6,660,027 | B2 | 12/2003 | Gruszeckl et al. |
| 6,669,715 | B2 | 12/2003 | Hoglund et al. |
| 6,673,098 | B1 * | 1/2004 | Machold et al. ............... 607/96 |
| 6,673,099 | B2 | 1/2004 | Grahn et al. |
| 6,682,550 | B2 | 1/2004 | Clifton et al. |
| 6,685,731 | B2 | 2/2004 | Kushnir et al. |
| 6,692,518 | B2 | 2/2004 | Carson |
| 6,695,872 | B2 | 2/2004 | Elkins |
| 6,699,267 | B2 | 3/2004 | Voorhees et al. |
| 6,709,447 | B1 | 3/2004 | Gammons |
| 6,718,785 | B2 | 4/2004 | Bieberich |
| 6,730,115 | B1 | 5/2004 | Heaton |
| 6,739,001 | B2 | 5/2004 | Flick et al. |
| 6,743,250 | B2 | 6/2004 | Renfro |
| 6,749,624 | B2 | 6/2004 | Knowlton |
| 6,764,502 | B2 | 7/2004 | Bieberich |
| 6,799,063 | B2 | 9/2004 | Carson |
| 6,800,087 | B2 | 10/2004 | Papay et al. |
| 6,800,088 | B1 | 10/2004 | Karapetyan |
| 6,802,855 | B2 | 10/2004 | Ellingboe et al. |
| 6,818,012 | B2 | 11/2004 | Ellingboe |
| 6,855,158 | B2 | 2/2005 | Stolpmann |
| D527,822 | S | 9/2006 | Trevino |
| 7,380,302 | B2 | 6/2008 | Gilchrest, Jr. et al. |
| 2002/0116041 | A1 | 8/2002 | Daoud |
| 2002/0177837 | A1 | 11/2002 | Barnitz |
| 2003/0024684 | A1 | 2/2003 | Lyons et al. |
| 2003/0097163 | A1 | 5/2003 | Kane et al. |
| 2003/0125649 | A1 | 7/2003 | McIntosh et al. |
| 2003/0195596 | A1 | 10/2003 | Augustine et al. |
| 2003/0236561 | A1 | 12/2003 | Lennox |
| 2004/0049252 | A1 | 3/2004 | Gluderer |
| 2004/0064170 | A1 | 4/2004 | Radons et al. |
| 2004/0064171 | A1 | 4/2004 | Briscoe et al. |
| 2004/0068310 | A1 | 4/2004 | Edelman |
| 2004/0087606 | A1 | 5/2004 | Voorhees et al. |
| 2004/0093050 | A1 | 5/2004 | Beard et al. |
| 2004/0158303 | A1 | 8/2004 | Lennox et al. |
| 2004/0186537 | A1 | 9/2004 | Heaton et al. |
| 2004/0187512 | A9 | 9/2004 | Becker et al. |
| 2004/0204748 | A1 | 10/2004 | Hansen et al. |
| 2004/0225341 | A1 | 11/2004 | Schock et al. |
| 2004/0243202 | A1 | 12/2004 | Lennox |
| 2005/0027218 | A1 | 2/2005 | Filtvedt et al. |
| 2005/0060012 | A1 | 3/2005 | Voorhees et al. |

FOREIGN PATENT DOCUMENTS

| | | |
|---|---|---|
| GB | 2263872 | 8/1993 |
| JP | 10/033626 | 2/1998 |
| WO | WO 88/10074 A1 | 12/1988 |
| WO | WO 94/05238 A1 | 3/1994 |
| WO | WO 96/13234 A1 | 5/1996 |
| WO | WO 98/40039 A1 | 9/1998 |
| WO | WO 99/09916 A1 | 3/1999 |
| WO | WO 99/39678 A1 | 8/1999 |
| WO | WO 99/44552 A1 | 9/1999 |
| WO | WO 01/50988 A1 | 7/2001 |
| WO | WO 2004023982 | 3/2004 |

OTHER PUBLICATIONS

Bernard, S.A., et al., "Treatment of Comatose Survivors of Out-of-Hospital Cardiac Arrest with Induced Hypothermia", New England Journal of Medicine, Feb. 21, 2002, pp. 557-563, vol. 346, No. 8, Massachusetts Medical Society, Boston, Massachusetts, United States.

Blair, D., et al., "The Increase in Tone in Forearm Resistance Blood Vessels Exposed to Increased Transmural Pressure", The Journal of Physiology, Jul. 1959, pp. 614-625, vol. 149, Cambridge University Press, London, Great Britain.

Felberg, R., et al., "Hypothermia After Cardiac Arrest: Feasibility and Safety of an External Cooling Protocol", Circulation, 2001, pp. 1799-1804, vol. 104, American Heart Association, Dallas, Texas, United States.

Future Medical Products, Inc., "Enhanced External Counterpulsation (EECP) Fact Sheet", Mar. 1994, pp. 1-3.

Gordon, "Blood-Pump Cuffs Curb Angina", Apr. 21, 1994, p. 1.

Grahn, D., et al., "Recovery from Mild Hypothermia can be Accelerated by Mechanically Distending Blood Vessels in the Hand", Journal of Applied Physiology, Nov. 1998, pp. 1643-1648, vol. 85, No. 5, The American Physiological Society, Bethesda, Maryland, United States.

Guyton, A.C., "Body Temperature, Temperature Regulation, and Fever", Textbook of Medical Physiology, 1986, p. 859, W.B. Saunders Company.

Henriksen, O., "Local Sympathetic Reflex Mechanism in Regulation of Blood Flow in Human Subcutaneous Adipose tissue", ACTA Physiologica Scandinavica, 1977, 48 pages, Supplement 450, Almqvist & Wiksell, Uppsala, Sweden.

Henriksen, O., "Sympathetic Reflex Control of Blood Flow in Human Peripheral Tissues", ACTA Physiologica Scandinavica, 1991, pp. 33-39, vol. 143, Supplement 603, ACTA Physiologica Scandinavica, Stockholm, Sweden.

Holzer, M., et al., "Mild Therapeutic Hypothermia to Improve the Neurologic Outcome after Cardiac Arrest", New England Journal of Medicine, Feb. 21, 2002, pp. 549-556, vol. 346, No. 8, Massachusetts Medical Society, Boston, Massachusetts, United States.

Oakley, E., et al., "Can Recovery From Mild Hypothermia be Accelerated so Much by Mechanically Distending Locally Heated Blood Vessels?", Journal of Applied Physiology, Aug. 1999, pp. 867-868, vol. 87, No. 2, The American Physiology Society, Bethesda, Maryland, United States.

Janicki, et al., "Comparison of Two Different Temperature Maintenance Strategies During Open Abdominal Surgery", Anesthesiology, Oct. 2001, pp. 868-874, vol. 95.

Kirklin, et al., "Hypothermia, Circulatory Arrest, and Cardiopulmonary Bypass", Chapter 2, 1993, pp. 113-114, vol. 1, Second Edition, Churchill Livingston.

Koscheyev et al., "Augmentation of Blood Circulation to the Fingers by Warming Distant Body Areas", European Journal of Applied Physiology and Occupational Physiology (2000), pp. 103-111, 82.

Lawson, W.E., et al., "Efficacy of Enhanced External Counterpulsation in the Treatment of Angina Pectoris", Oct. 1, 1992, pp. 859-862.

Lawson, W.E., et al., "Efficacy of Enhanced External Counter-pulsation in the Treatment of Angina Pectoris", 1992, p. 1.

Lawson, W.E., et al., "Benefits are Sustained at 3-Year Follow-up in Patients Who Have Been Treated With Enhanced External Counterpulsation", Mar. 13, 1994, p. 1.

Mellergard, "Changes in Human Intracerebral Temperature in Response to Different Methods of Brain Cooling", Neurosurgery, Oct. 1992, pp. 671-677, vol. 31, No. 4.

Nag, et al., "Efficacy of a Water-Cooled Garment for Auxiliary Body Cooling in Heat", Ergonomics, 1998, pp. 179-187, vol. 41, No. 2.

Nesher, et al., "A Novel Thermoregulatory System Maintains Perioperative Normothermia in Children Undergoing Elective Surgery", Pediatric Anesthesia, 2001, pp. 555-560.

Oster, M.D., "Guidelines for the Submission of Abstracts", Apr. 30, 1993, p. 1.

Plattner, et al., "Efficacy of Intraoperative Cooling Methods", Anesthesiology, Nov. 1997, pp. 1089-1095, vol. 87(5), printed from www.anesthesiology.org.

Raven, et al., "Hemodynamic Changes During Whole Body Surface Cooling and Lower Body Negative Pressure", Aviation, Space, and Environmental Medicine, Jul. 1981, pp. 387-391.

Taguchi, A., et al., "Negative Pressure Rewarming vs. Forced Air Warming in Hypothermic Postanesthetic Volunteers", Anesthesia &

Analgesia, Jan. 2001, pp. 261-266, vol. 92, No. 1, International Anesthesia Research Society et al., San Francisco, California, United States.

Wolthuis, R., et al., "Physiological Effects of Locally Applied Reduced Pressure in Man", Physiological Reviews, 1974, pp. 566-595, vol. 54, The American Physiological Society, Bethesda, Maryland, United States.

Zhen-Sheng Zheng, et al., "Sequential External Counterpulsation (SECP) in China", 1983, pp. 1-5.

Zhen-Sheng Zheng, et al., "New Sequential External Counterpulsation for the Treatment of Acute Myocardial Infarction", Aug. 1984, pp. 470-476.

"Treatment of Refractory Fever in Neurosciences Critical Care Unit Using a Novel, Water-Circulating Cooling Device", Journal of Neurosurgical Anesthesiology, vol. 15, No. 4, pp. 313-318, 2003.

Effects of Inducted Hypothermia on Samatosensory Evoked Potentials in Patients with Chronic Spinal Cord Injury, Paraplegia 31, 730-741, 1993.

Gardella et al., "Lowering Body Temperature with a Cooling Suit as Symptomatic Treatment for Thermosensitive Multiple Scherosis Patients", Ital. J. Neurol. Sci., 1995.

Syndulko et al., "Preliminary Evaluation of Lowering Tympani Temperature for the Symptomatic Treatment of Multiple Sclerosis", J. Neuro. Rehab., vol. 9, No. 4, 1995.

Ku et al., "Hemodynamic and Thermal Responses to Head and Neck Cooling in Men and Women", Am J Phys Med Rehabil, 75:443-450, 1996.

Spinoff, "New Help for MS Patients" 1993.

"Acute Effects of Cooling in Multiple Sclerosis: Pilot Study to Compare Two Cooling Garments", 1995.

Flensner et al., "The Cooling-Suit: Case Studies of its Influence on Fatigue Amoung Eight Individuals with Multiple Sclerosis", Journal of Advanced Nursing 37(6), 541-550, Mar. 2002.

Ku et al., "Physiologic and Functional Responses of MS Patients to Body Cooling", Multiple Sclerosis, Sep./Oct. 2000, 427-434.

Regan et al., "Effect of body temperature on visual evoked potential delay and visual perception in multiple sclerosis", Journal of Neurology, Neurosurgery, and Psychiatry, 1977, 40, 1083-1091.

Greenleaf, et al., Fluid-electrolyte shifts and thermoregulation: Rest and work in heat with head cooling, Aug. 1980, vol. 51, No. 8, ASEMCG 5(8): 747-850.

* cited by examiner

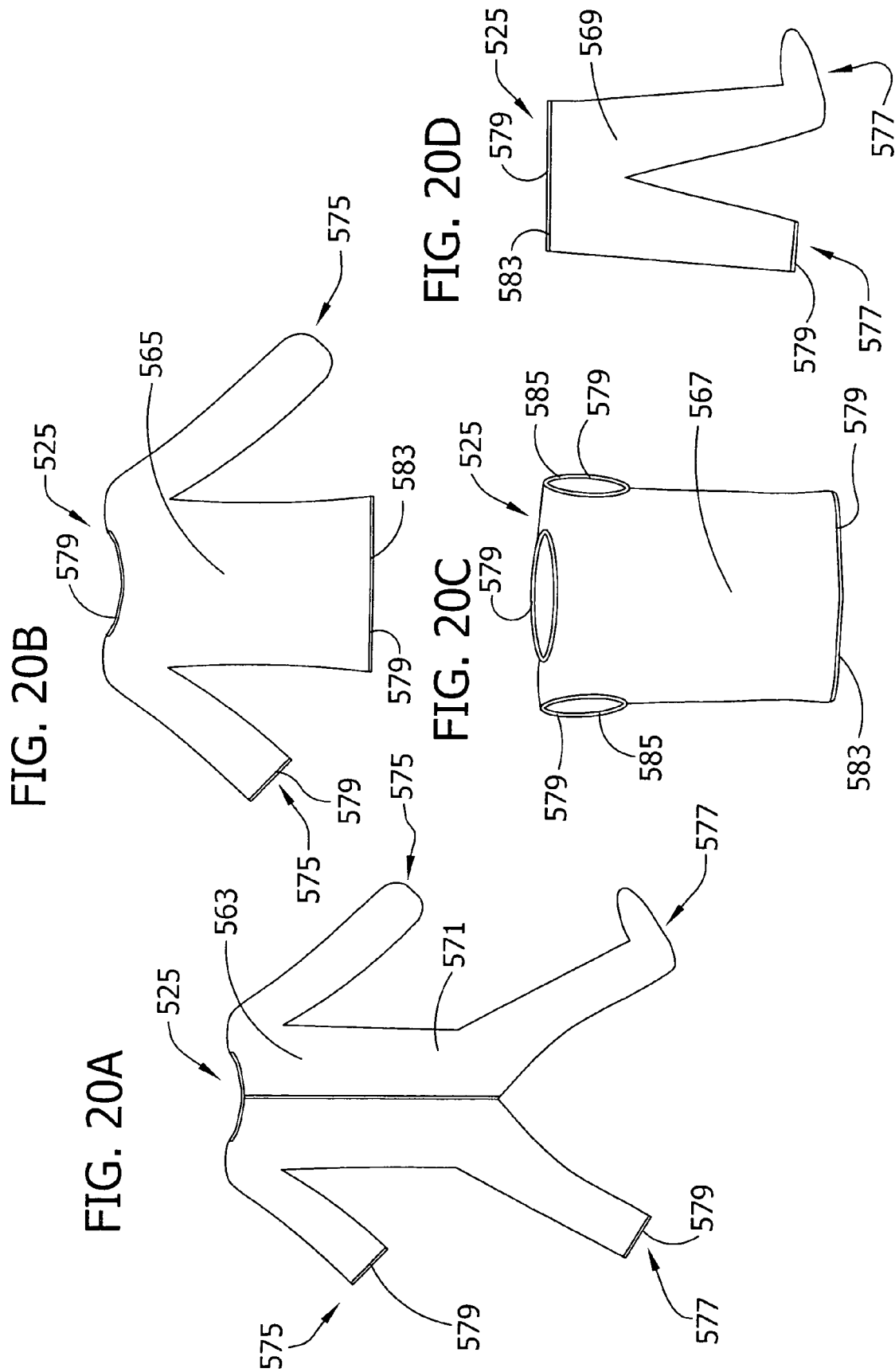

APPARATUS FOR ALTERING THE BODY TEMPERATURE OF A PATIENT

CROSS-REFERENCE TO RELATED APPLICATION

This application is a continuation-in-part of co-pending U.S. application Ser. No. 10/193,635 filed Jul. 11, 2002.

BACKGROUND OF THE INVENTION

This invention generally relates to medical apparatus for altering the body temperature of a patient and more particularly to apparatus that enables efficient, quick control of the body temperature of a patient, especially to induce hypothermia.

Sudden cardiac arrest remains a serious public health issue. Approximately 350,000 individuals are stricken in the United States annually, with overall survival rates of roughly 5 percent. Even with the immediate availability of the most advanced care currently available, including cardiopulmonary resuscitation (CPR), drugs, ventilation equipment, and automatic external defibrillators, a survival rate of 25 percent may be the probable best case scenario. Improved therapies to deal with this condition are clearly needed.

Numerous incidences of recovery following accidental hypothermia and cardiac arrest have been reported. This observation has led researchers to consider therapeutic hypothermia as a possible treatment for reducing the adverse consequences of circulatory arrest. Various studies have shown that moderate systemic hypothermia (approximately 3-5° C. (5.4-9.0 ° F.)) can reduce damage to vital organs, including the brain. Hypothermia induced both during and following cardiac arrest has demonstrated this benefit. The use of cardiopulmonary bypass has also been effective in rapidly achieving this goal. Direct flushing of cooled fluids into the arterial system has also been employed with success. Both invasive measures, however, require large bore intravascular catheters and rapid introduction of sterile solutions into the patient. Such invasive approaches have obvious disadvantages in dealing with out-of-hospital emergencies.

Noninvasive cooling, if sufficiently effective and portable, would be a preferable approach. Direct cooling of the head alone has produced variable results. However, post-resuscitative cooling of the entire body to approximately 33° C. (91.4° F.) by noninvasive treatment has been demonstrated to be surprisingly effective in recent clinical studies. The use of cold gel and ice packs produced cooling of approximately 0.9° C. (1.6° F.) per hour, and resulted in a nearly 100 percent improvement in neurologically intact survival (Bernard S. A. et al., *Treatment of Comatose Survivors of Out-of-Hospital Cardiac Arrest with Induced Hypothermia*, 346 NEW ENG. J. MED. 557-563 (2002)). In another study, cold air was found to be capable of cooling patients at a rate of about 0.25 ° C. (0.45° F.) per hour, which caused a 40 percent improvement in the same endpoint (Sterz F. et al., *Mild Therapeutic Hypothermia to Improve the Neurologic Outcome after Cardiac Arrest*, 346 NEW ENG. J. MED. 549-556 (2002)). In yet another study, a combination of water-filled cooling blankets and ice packs applied to the skin resulted in a cooling rate of 0.8° C. (1.4° F.) per hour (Felberg et al., *Hypothermia After Cardiac Arrest—Feasibility and Safety of an External Cooling Protocol*, 104 CIRCULATION 1799-1804 (2001)). Despite the success of these studies, increasing the rate of cooling may produce a higher rate of patient salvage.

Based on the current cooling procedures and systems, the present invention explores a unique solution to the problem of accelerated body cooling. Namely, the present invention is based upon the hypothesis that full body contact with a liquid medium, such as cold water, would induce high rates of heat transfer. Beyond immersion, controlling the liquid temperature and flow rate may allow further control of the cooling process, thereby producing a valuable system.

SUMMARY OF THE INVENTION

Among the several objects and features of the present invention may be noted the provision of an apparatus and method capable of decreasing the time required to induce hypothermia in a patient; the provision of an apparatus and method capable of controlled warming of a patient; the provision of such an apparatus and method that permits the delivery of temperature responsive pharmaceuticals during cooling or warming; the provision of such an apparatus and method in which cooling liquid is brought into direct contact with skin; the provision of such an apparatus and method that allows for cooling or warming of the patient in a remote environment without electricity; and the provision of such an apparatus that allows for cooling or warming while the patient is in transport.

Generally, the present invention is directed to apparatus for adjusting the body temperature of a patient. The apparatus comprises an enclosure defining an interior space for receiving a portion of a patient's body. The enclosure is constructed for receiving heat transfer liquid into the interior space for direct liquid contact with the portion of the patient's body to promote heat transfer between the patient and the heat transfer liquid. At least a portion of the enclosure includes an outer layer, and a porous inner fluid transfer layer engageable with the portion of the patient's body for carrying the heat transfer liquid. The transfer layer is formed from a substantially hydrophobic material.

In another aspect of the present invention, apparatus for adjusting the body temperature of a patient generally comprises an enclosure defining an interior space for receiving a portion of a patient's body. The enclosure is constructed for receiving heat transfer liquid into the interior space for direct liquid contact with the portion of the patient's body to promote heat transfer between the patient's body and the heat transfer liquid. At least a portion of the enclosure includes a sheet-like body-facing component and a sheet-like outer component. The sheet-like body-facing component and sheet-like outer component are in face-to-face relationship with one another. The components are further joined to one another along their facing sides to form at least one liquid passage between the components. The liquid passage is in fluid communication with the interior space of the enclosure. The body-facing component has at least one inlet therein corresponding to the liquid passage for allowing liquid to pass from the liquid passage to between the body-facing component and the portion of the patient's body. A liquid delivery system drives the heat transfer liquid to flow through the liquid passage and inlet into the interior space.

In still another aspect of the present invention, apparatus for adjusting the body temperature of a patient generally comprises an enclosure defining an interior space for receiving at least a portion of a patient's body therein. An inlet, in fluid communication with the interior space of the enclosure, receives heat transfer liquid for flow over the portion of the patient's body in direct liquid contact therewith to promote heat transfer between the patient's body and the heat transfer liquid. An outlet, also in fluid communication with the interior space of the enclosure, exhausts the heat transfer liquid from the enclosure. At least one sensor is disposed within the enclosure for directly measuring a property of the heat transfer liquid within the enclosure. A control unit processes the property of the heat transfer liquid and correspondingly distributes the heat transfer liquid within the enclosure in response to the property of the heat transfer liquid.

In still another aspect of the present invention, apparatus for adjusting the body temperature of a patient generally comprises an enclosure defining an interior space for receiving a portion of a patient's body. A liquid delivery system drives heat transfer liquid into the interior space of the enclosure for direct liquid contact with the portion of the patient's body received therein to promote heat transfer between the patient's body and the heat transfer liquid. The liquid delivery system has a thermally conductive fluid reservoir for holding the heat transfer liquid.

In still another aspect of the present invention, apparatus for adjusting the body temperature of a patient generally comprises an enclosure defining an interior space for receiving a portion of a patient's body. A liquid delivery system drives heat transfer liquid into the interior space of the enclosure for direct liquid contact with the portion of the patient's body received therein to promote heat transfer between the patient's body and the heat transfer liquid. The liquid delivery system has a fluid reservoir. The reservoir has a first compartment for holding a phase change material and a second compartment for holding the heat transfer liquid. The compartments are arranged such that the phase change material alters the temperature of the heat transfer liquid.

In still another aspect of the present invention, apparatus for adjusting the body temperature of a patient generally comprises an enclosure defining an interior space for receiving a portion of a patient's body. A liquid delivery system drives heat transfer liquid into the interior space of the enclosure for direct liquid contact with the portion of the patient's body received therein to promote heat transfer between the patient's body and the heat transfer liquid. The liquid delivery system has a pump for transferring the heat transfer liquid. The pump includes a detachable pumphead.

In still another aspect of the present invention, apparatus for adjusting the body temperature of a patient generally comprises an enclosure defining an interior space for receiving a portion of a patient's body. A liquid delivery system drives heat transfer liquid into the interior space of the enclosure for direct liquid contact with the portion of the patient's body received therein to promote heat transfer between the patient's body and the heat transfer liquid. At least a portion of the liquid delivery system is in direct fluid communication with the heat transfer liquid after it has contacted the portion of the patient's body. The portion of the liquid delivery system is disposable.

Another aspect of the present invention is directed to a method of administering a temperature responsive pharmaceutical to the body of a patient with a fluid as a carrying agent. The method generally comprises enclosing at least a portion of the patient's body within an enclosure defining an interior space for receiving the portion of a patient's body therein. The enclosure has an inlet in fluid communication with the interior space of the enclosure for receiving the fluid into the interior space, and an outlet in fluid communication with the interior space of the enclosure for exhausting the fluid from the enclosure. The method also includes delivering the temperature responsive pharmaceutical into the interior space of the enclosure for direct liquid contact with the portion of the patient's body.

In still another aspect of the present invention is generally directed to a method for adjusting the body temperature of a patient. The method comprises substantially enclosing at least a portion of a patient's body within an interior space of an enclosure. The enclosure has an inlet for receiving heat transfer liquid into the interior space for flow over the patient's body in direct liquid contact therewith to promote heat transfer between the patient's body and the heat transfer liquid, and an outlet in fluid communication with the interior space of the enclosure for exhausting the heat transfer liquid from the enclosure. The method also includes directing the heat transfer liquid through the inlet of the enclosure into the interior space to the outlet of the enclosure. Simultaneously with the step of directing heat transfer liquid, the patient is administered at least one therapy selected from a group of therapies including iced saline infusion, cardiopulmonary bypass, veno-veno bypass, intravascular cooling catheters, temperature-controlled ventilation, intravascular infusion of a slurry of ice and saline, and intrapulmonary infusion of a slurry of ice and saline.

Other objects and features will be in part apparent and in part pointed out hereinafter.

BRIEF DESCRIPTION OF THE DRAWINGS

FIG. 20A shows an another version of the enclosure in the form of a jumpsuit having optional hand and foot barrier cuffs or enclosures;

FIG. 20B shows still another version of the enclosure in the form of a shirt having an optional hand barrier cuff or enclosure;

FIG. 20C show yet another version of the enclosure in the form of a vest having arm and neck barrier cuffs;

FIG. 20D shows another version of the enclosure in the form of a pair of pants having an optional foot barrier cuff or enclosure;

Corresponding reference characters indicate corresponding parts throughout the several views of the drawings.

DETAILED DESCRIPTION OF THE PREFERRED EMBODIMENT

Figure 1:
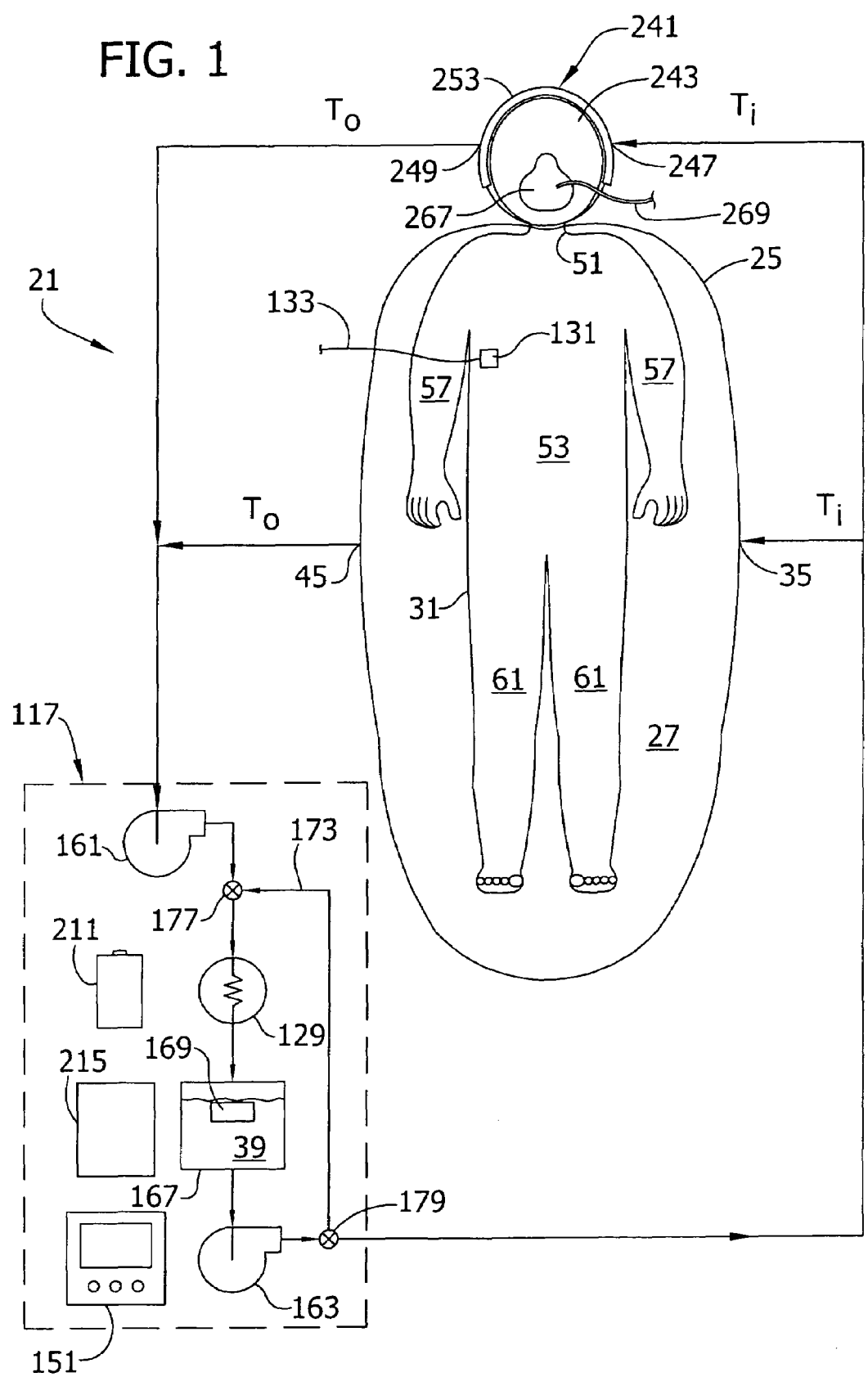
FIG. 1 is a schematic of apparatus of the present invention for altering the body temperature of a patient.

Referring now to the drawings and particularly to FIG. 1, reference number 21 generally indicates an apparatus for adjusting the body temperature of a patient. The apparatus 21 generally comprises an enclosure 25 defining an interior space 27 for receiving at least a portion 31 of a patient's body therein. The enclosure 25 is configured for enclosing the portion 31 of the patient's body (illustrated in FIG. 1 as all of the patient's body below the head) within the interior space 27 with the enclosure generally contiguous with the patient's body. An inlet 35 of the enclosure 25 is adapted to receive heat transfer liquid 39, such as water, saline or other biocompatible liquids, into the enclosure. The inlet 35 is further in fluid communication with the interior space 27 of the enclosure 25 to direct heat transfer liquid 39 into the interior space 27 for flowing over the patient's body portion 31 in direct contact therewith to promote heat transfer between the patient's body portion and the heat transfer liquid. The enclosure 25 also has an outlet 45 in fluid communication with the interior space 27 of the enclosure for exhausting the heat transfer liquid 39 from the enclosure. More particularly, the enclosure 25 is adapted to generally conform to the portion of the patient's body 31 disposed within the interior space 27. Additionally, the inlet 35 and outlet 45 are positioned on the enclosure such that upon enclosure of the patient's body portion 31 within the interior space 27, the inlet faces a side of the patient's body portion opposite the outlet. Although any portion of the patient's body may be placed inside the enclosure 25, in one embodiment the portion enclosed includes the body of the patient from the neck 51 of the patient downward, including the torso 53, arms 57 and legs 61 of the patient.

Figure 2:
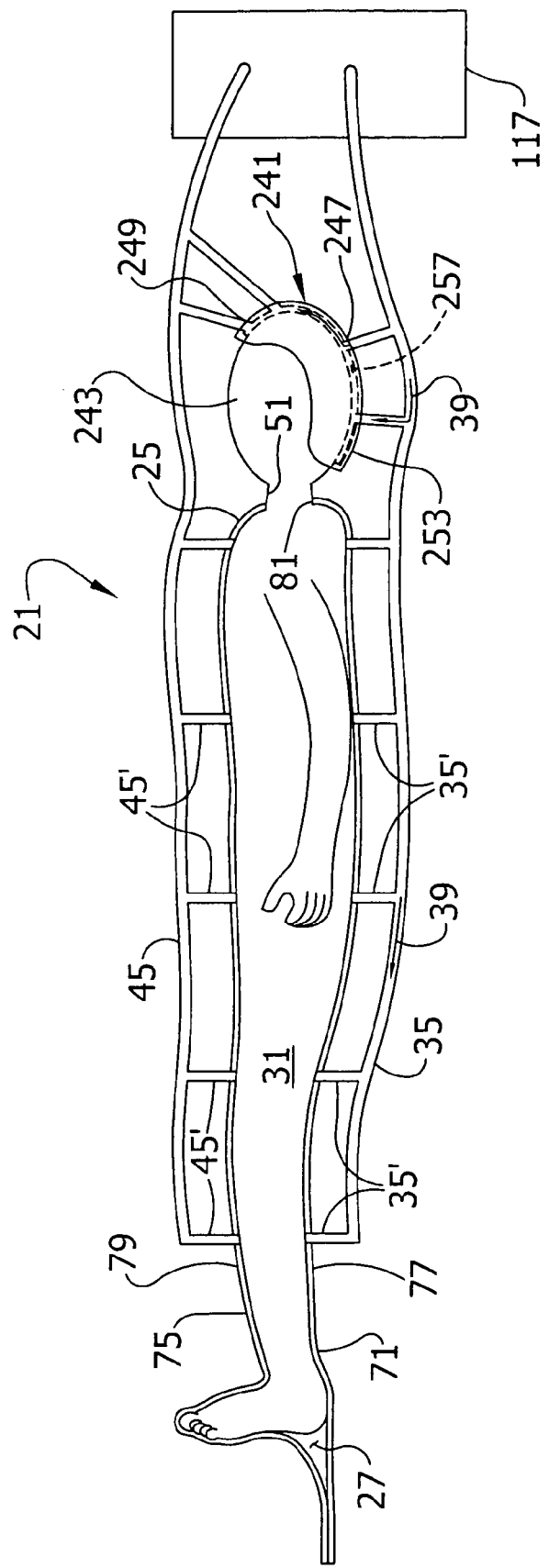
FIG. 2 is a partial elevation of the apparatus of FIG. 1 with portions of an enclosure of the apparatus removed to show detail.

In one embodiment, shown in FIG. 2, the enclosure 25 comprises a first sheet member 71 and a second sheet member 75 in sealing engagement with one another generally at their respective edge margins to form the interior space 27 for receiving the body portion 31. Here, the inlet 35 extends through the first sheet member 71 and the outlet 45 extends through the second sheet member 75. The sheet members 71,75 are disposed respectively above and below the body portion 31 of the patient, thereby arranging the inlet 35 and the outlet 45 on opposite sides of the patient. As shown in FIG. 2, the inlet 35 and outlet 45 may comprise multiple sub-inlets 35' and sub-outlets 45'. These sub-inlets and sub-outlets facilitate the flow of heat transfer liquid 39 over a larger area of the enclosed portion 31 of the patient's body, thereby promoting increased contact between the liquid and the portion of the patient's body.

More specifically, the first sheet member 71 may comprise a lower member 77 for placement beneath the body portion 31 and the second sheet member 75 may comprise an upper member 79 for placement above the body portion. The enclosure 25 of FIG. 2 depicts such a configuration, and is shown for illustrative purposes only. It is contemplated, for instance, that the outlet 45 may extend through the first sheet member 71, or lower member 77, while the inlet 35 may extend through the second sheet member 75, or upper member 79 (not shown). In the configuration depicted in FIG. 2, where the inlet 35 lies below the outlet 45, air trapped within the interior space 27 of the enclosure 25 will move up toward the outlet and be purged from the enclosure via the outlet. Purging air from the enclosure 25 increases the liquid contact with the body portion 31, thereby promoting more heat transfer between the body portion and liquid 39 for better control of body temperature. The first sheet member 71 and the second sheet member 75 of the illustrated embodiment additionally cooperate to form at least one neck opening 81 in the enclosure 25 (FIG. 2). The neck opening 81 is sized and shaped for sealing engagement of the sheet members 71,75 with the neck 51 of the patient at the opening. The enclosure 25 may include a strap, a hook and loop fastener or other sealing device (not shown) at the neck opening 81 to further promote sealing of the neck opening about the neck 51 of the patient at the opening. Adhesive hydrogels may also be applied to the neck 51 of the patient to further encourage sealing of the enclosure 25 about the patient's neck.

Figure 3:
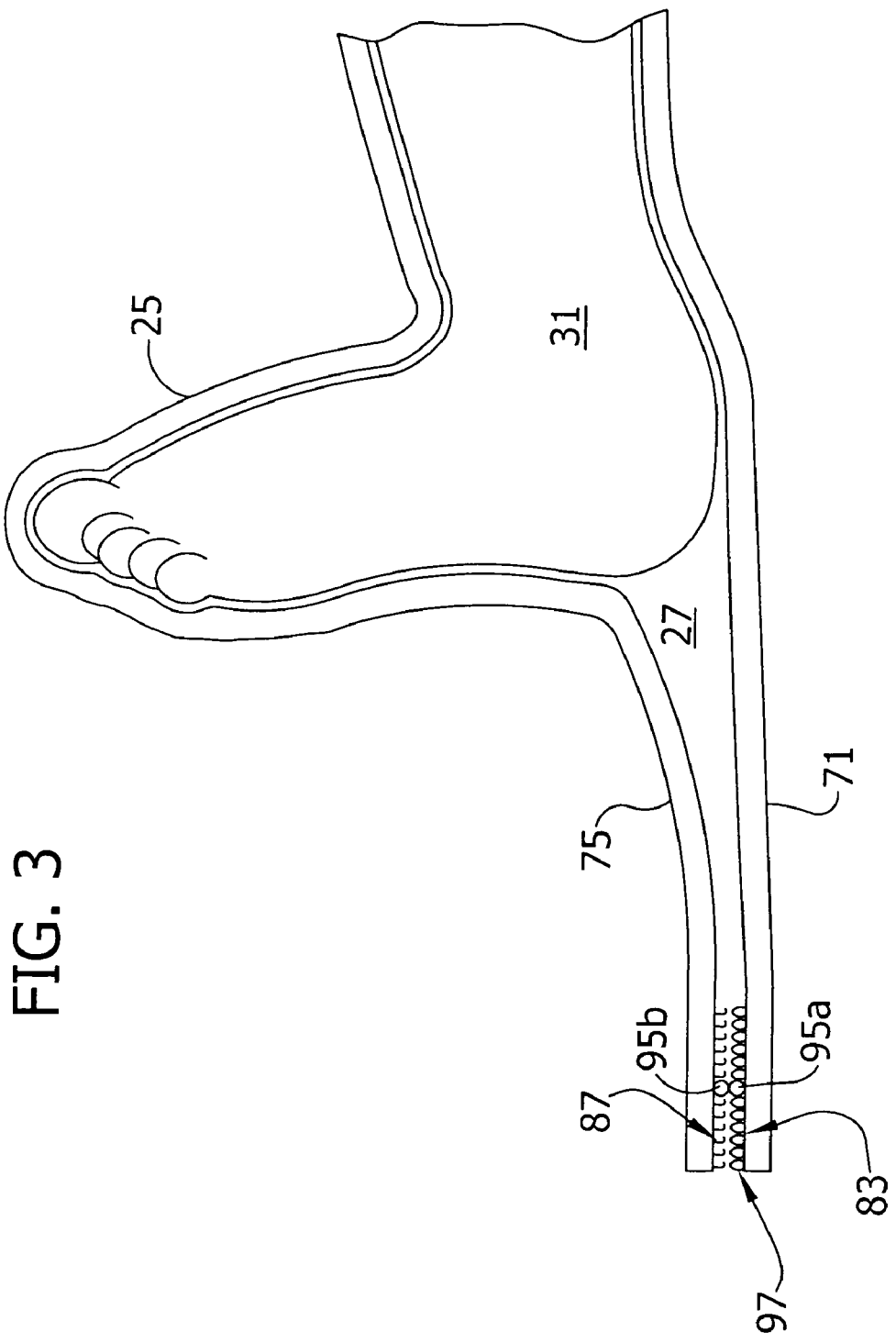
FIG. 3 is an enlarged fragmentary section of the enclosure of FIG. 2.
Figure 4:
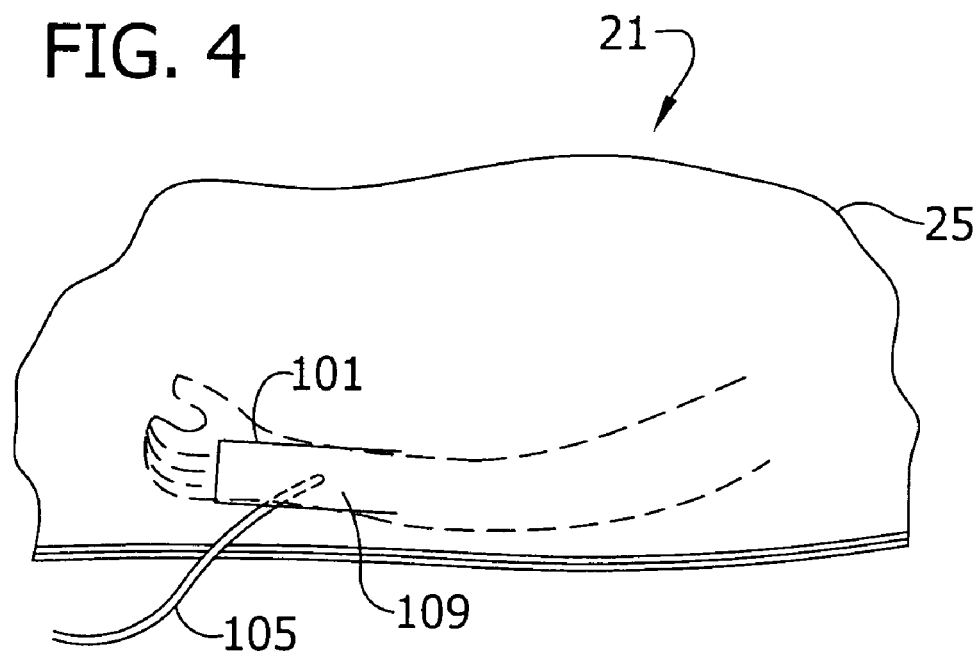
FIG. 4 is a fragmentary elevation of the apparatus with a sealable opening formed by a pivotable flap.

The first sheet member 71 includes a first sealing portion, generally indicated at 83, and the second sheet member 75 includes a second sealing portion, generally indicated at 87 (FIG. 3). The sealing portions 83,87 are sealingly engageable with one another for sealing the interior space 27 of the enclosure 25. The first and second sealing portions 83,87 each further comprise a gasket 95, for sealing the first and second sheet members 71,75, and a hook and loop fastener, generally indicated 97, for holding the sheet members in sealed engagement. The gasket 95 includes a first bead 95a on the first sealing portion 83 and a second bead 95b on the second sealing portion 87. Such beads 95a,95b may be formed from an elastomeric material, such as rubber. A hook and loop fastener, generally indicated 97, is positioned on opposite lateral sides of the beads 95a,95b, such that the hook and loop fastener portions compress the beads, forming a sealed enclosure 25. This seal inhibits liquid 39 leakage from the enclosure 25, or a loss of negative pressure within the interior space 27 of the enclosure.

Figure 5:
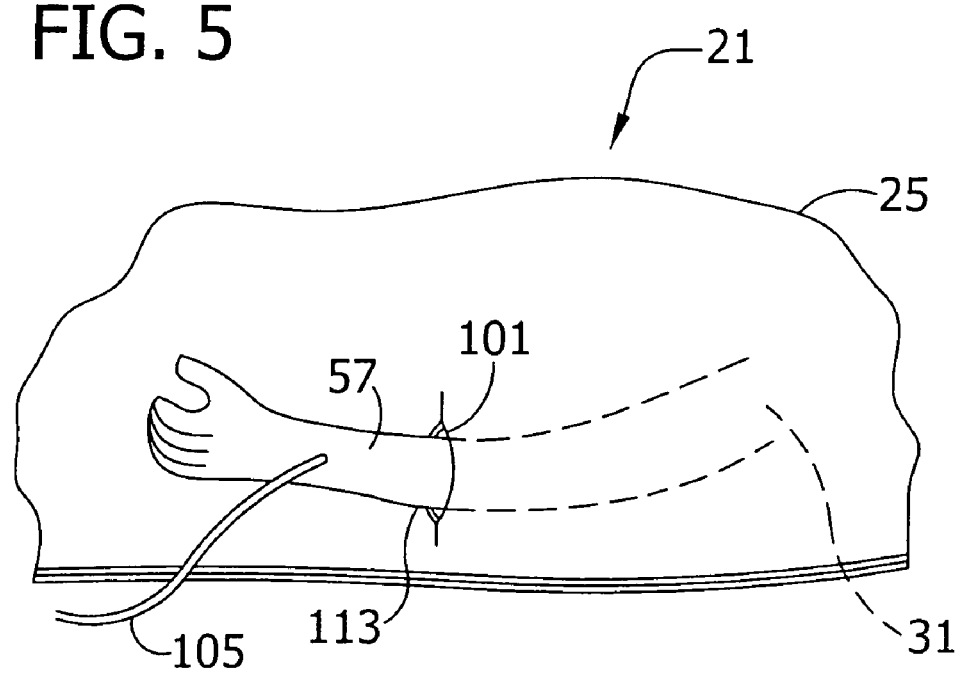
FIG. 5 is a fragmentary elevation of the apparatus with a sealable opening sealed about an arm of the patient.
Figure 6:
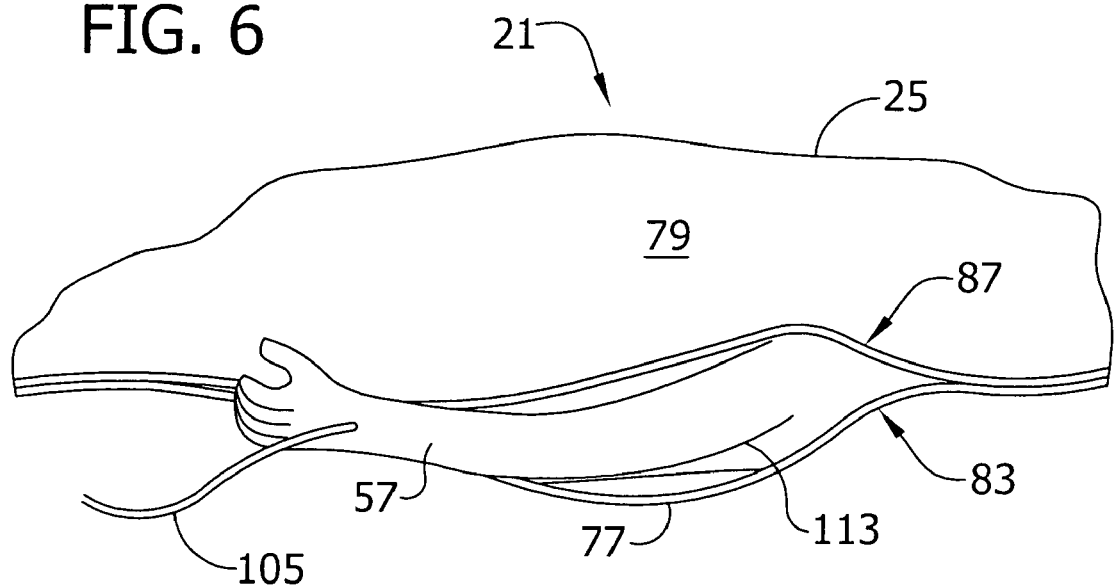
FIG. 6 is a fragmentary elevation of the apparatus with an arm of the patient passing between an upper member and lower member.
Figure 7:
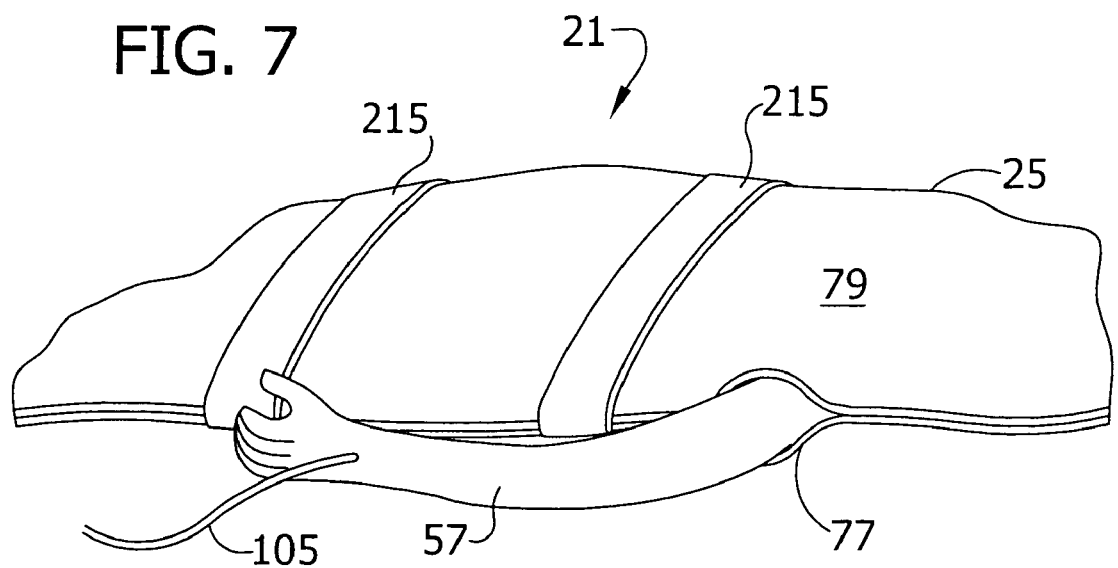
FIG. 7 is a fragmentary elevation of the apparatus of FIG. 6 with the upper and lower members sealed together about the patient's arm.

Referring now to FIGS. 4-7, the enclosure 25 further includes a sealable opening 101 for accessing the interior space 27 of the enclosure. Such a sealable opening 101 may be used for accessing the patient during use of the apparatus 21. The sealable opening 101 may also be sealed about an object, such as medical tubing 105, cords or other items which need to pass through the enclosure 25 into the interior space thereof. In one configuration, depicted in FIG. 4, a pivotable flap 109 defines a closure for the sealable opening 101. Medical tubing 105 or other items may pass through the opening 101 with the flap 109 sealed about them. For example, the opening 101 may provide access to the patient for administering a second therapy for altering the temperature of a patient such as iced saline infusion, cardiopulmonary bypass, veno-veno bypass, intravascular cooling catheters, temperature-controlled ventilation, intravascular infusion of a slurry of ice and saline, and intrapulmonary infusion of a slurry of ice and saline. Moreover, as shown in FIG. 5, the sealable opening 101 may be secured about a second body portion 113 of the patient's body, such as an arm 57 or leg, thereby allowing the second body portion to extend exterior of the enclosure 25 while substantially sealingly enclosing the body portion 31. This is particularly important where access to the second body portion 113 of the patient for performing a medical procedure, such as drawing blood or placing a medical device, e.g., an intravenous catheter, is warranted. As shown in FIGS. 6 and 7, the second body portion 113 may also extend out from the enclosure between the lower member 77 and upper member 79, e.g., without the use of an additional opening 101. In this configuration, the first and second sealing portions 83,87 cooperate to form a seal about the second body portion 113 as it extends out from the enclosure 25, as shown in FIG. 7. In each of these configurations, adhesive hydrogels may be applied to the second body portion 113 of the patient to further promote sealing of the enclosure 25 about the second body portion.

Figure 8:
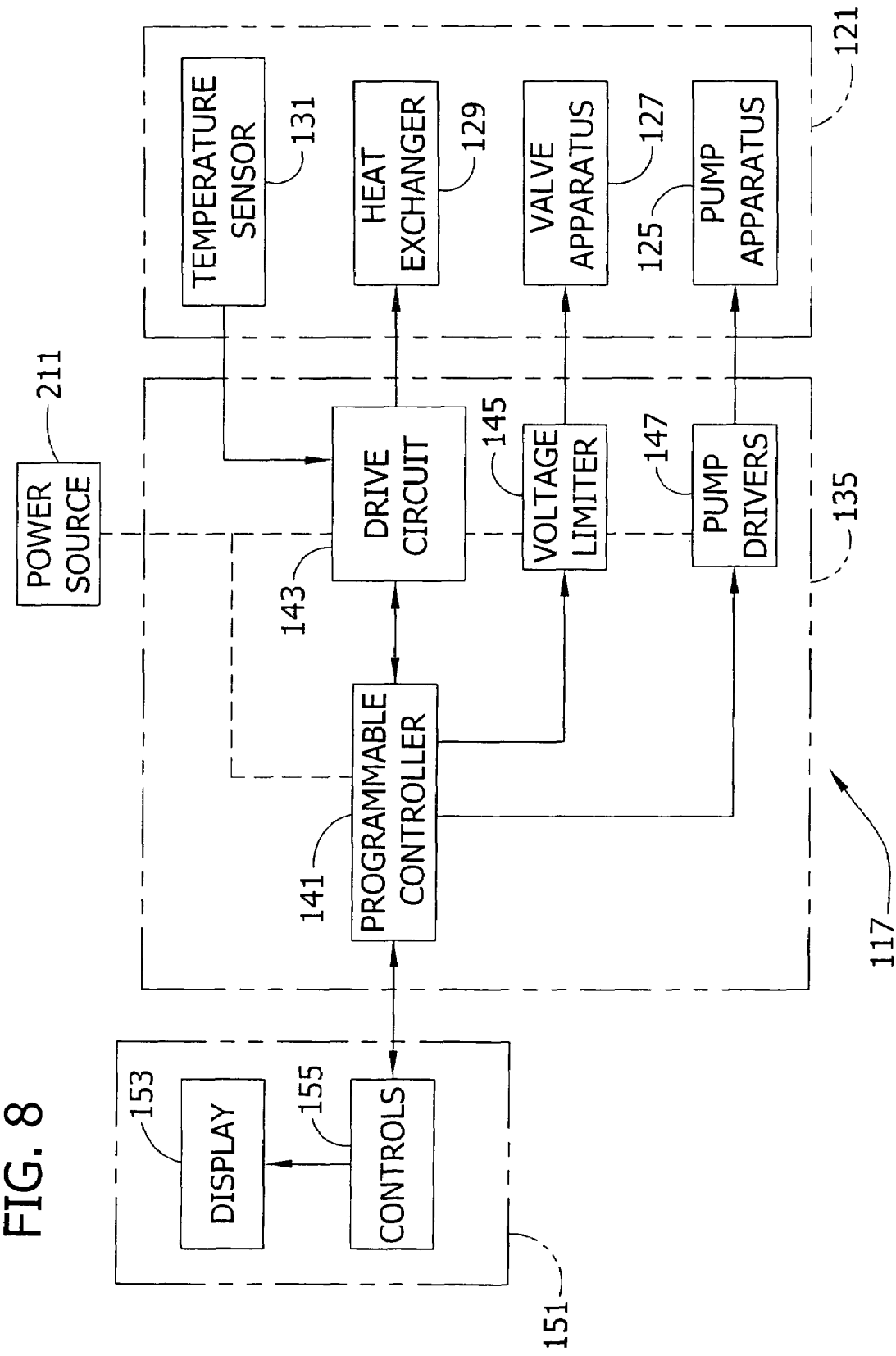
FIG. 8 is a schematic of a portable control unit of the apparatus of the present invention.

Referring now to FIG. 8, the apparatus 21 further comprises a portable control unit, generally indicated at 117, for controlling operation of the apparatus. The control unit 117 comprises a liquid delivery system 121 for directing the heat transfer liquid 39 to flow through the inlet 35 of the enclosure 25 into the interior space 27 to the outlet 45 of the enclosure. The liquid delivery system 121 comprises a pump apparatus 125, a valve apparatus 127, a heat exchanger 129 and a temperature sensor 131. The liquid delivery system 121 is a generally closed, continuous flow system whereby liquid 39 exhausted from the outlet 45 is directed to flow back to the inlet 35 for flow into the interior space 27 of the enclosure 25. A control system 135 communicates with the liquid delivery system 121 to control the flow of liquid 39 through the enclosure 25. The temperature sensor 131 is adapted for sending a body temperature reading of the patient to the control system 135, so that the control system can use this information to control the pump apparatus 125, valve apparatus 127 and heat exchanger 129. The control system 135 comprises a programmable controller 141, an H-bridge drive circuit 143, a voltage limiter 145 and pump drivers 147. The control system 135 provides temperature regulation, drives the pump apparatus 125 and controls the valve apparatus 127. The apparatus 21 further includes a user interface 151 for communicating the status of the system to the user. The user interface 151 includes a display 153 for visually indicating particular parameters of the system and controls 155 that allow the user of the system to selectively control particular system functions. For example, such controls may allow the user to input a set-point, or target, body temperature for the patient. The display 153, for example, could display this set-point temperature along with the actual body temperature of the patient, the liquid 39 temperature and the liquid flow rate, among other things.

Referring back to FIG. 1, the pump apparatus 125 of the portable control unit 117 comprises an outlet pump 161 in fluid communication with the outlet 45 for exhausting heat transfer liquid 39 from the enclosure 25 and an inlet pump 163 in fluid communication with the inlet 35 for pumping heat transfer liquid into the enclosure. The heat exchanger 129 is in fluid communication with the outlet pump 161 and the inlet pump 163, such that liquid 39 exhausted from the enclosure 25 by the outlet pump passes through the heat exchanger before entering the inlet pump. For example, the pumps 161, 163 may be 12 volt direct current pumps having a pumping capacity of 2.4 liters per minute (0.63 gallons per minute). The pumping capacity of such pumps may be increased to 3.0 liters per minute (0.79 gallons per minute) with 18 volts, but not without degrading pump life. Should higher flow rates or other parameters be required, alternative pumps, such as higher capacity gear or centrifugal pumps, may be used without departing from the scope of the present invention.

The pump apparatus 125 further comprises a reservoir 167 in fluid communication with the inlet pump 163 and the heat exchanger 129, such that liquid 39 passing through the heat exchanger flows into the reservoir before flowing into the inlet pump. The relative positions of the reservoir 167 and heat exchanger 129 may also be reversed, such that liquid 39 from the enclosure 25 flows directly into the reservoir for storage, until passing from the reservoir and through the heat exchanger immediately before reentering the enclosure. Such an arrangement might be useful if rapid changes in the liquid 39 temperature were required. Returning now to the original configuration, the reservoir 167 collects liquid 39 at the temperature induced by the heat exchanger 129 and stores it before the inlet pump 163 pumps the liquid into the enclosure 25. The reservoir 167 may have insulation (not shown) to help maintain and/or alter the temperature of the heat transfer liquid 39 before it is pumped into the enclosure 25. Although any size reservoir may be used, the reservoir of one embodiment has a capacity of about 16 liters (4.2 gallons). A reservoir with a smaller volume, such as 4 liters (1.1 gallons), ensures continued cycling of liquid through the apparatus 21. It is also contemplated that reservoirs with larger volumes, such as 30 liters (8 gallons), could also be used.

Figure 1A:
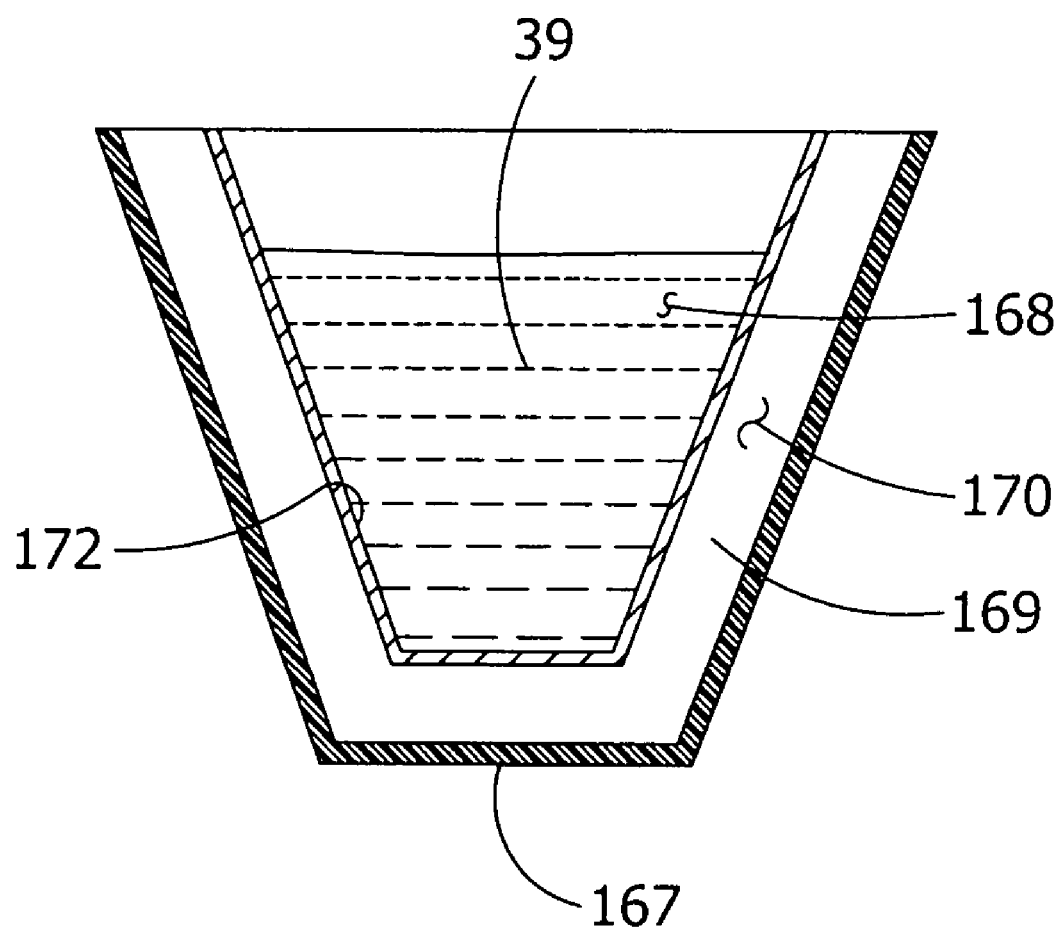
FIG. 1A is a section of a reservoir having two compartments.

Referring to FIG. 1, the reservoir 167 may also comprise a liquid temperature change component 169 in heat transfer communication with the liquid 39 for changing the temperature of the liquid. The component 169 may also provide temperature stabilization once the liquid 39 within the reservoir 167 reaches a particular temperature. The component 169 may be any material capable of absorbing or releasing heat, such as ice or another phase change material. In one configuration, the liquid temperature change component 169 is in direct contact with the liquid 39 within the reservoir 167 (FIG. 1). In another configuration, the liquid temperature change component 169 is placed in a separate compartment of the reservoir 167 and does not directly contact the liquid 39 within the reservoir (FIG. 1A). In this configuration, heat transfer occurs through the wall 172 dividing the reservoir compartments. Although the reservoir 167 may have any shape, in one configuration, the reservoir has two compartments 168 and 170 that have tapered cross-sections. The reservoir compartment 168 for holding the liquid 39 is smaller and adapted to be received in a second compartment 170 for holding the liquid temperature change component 169. As a result of its shape, the surface area of the wall 172 between the liquid temperature change component 169 and the liquid 39 is increased to help alter and/or maintain the temperature of the heat transfer liquid 39. Furthermore, the wall 172 between the two compartments 168, 170 is made from a thermally conductive material, such as aluminum, to thereby increase the effect the liquid temperature change component 169 has on the liquid 39.

In addition, Peltier devices can be used to maintain the two compartments at different temperatures. For example, the compartment 170 for holding the liquid temperature change component 169 may be maintained at −10° C. and the reservoir compartment may be maintained at 2° C. The use of Peltier devices inhibits the premature degradation of the liquid temperature change component 169 while maintaining the liquid 39 in a cooled state. As a result, the integrity of the liquid temperature change component 169 is preserved and the liquid 39 is maintained at a temperature suitable for contact with a patient. Since at least a portion of the reservoir 167 contacts the heat transfer liquid 39, which has been in direct contact with the patient, the reservoir or a portion thereof may be disposable to prevent cross-contamination to subsequent patients.

The pump apparatus 125 further comprises a bypass conduit 173 in fluid communication with the heat exchanger 129 and the inlet pump 163. The bypass conduit 173 communicates at one end with a first three-way valve 177, between the outlet pump 161 and the heat exchanger 129, and at its other end with a second three-way valve 179, between the inlet pump 163 and the enclosure 25. While operating in a normal mode, without use of the bypass conduit 173, the liquid 39 passes through the outlet pump 161, the first three-way valve 177, the heat exchanger 129, the reservoir 167, the inlet pump 163, the second three-way valve 179 and the enclosure 25. The normal mode is used when a patient is enclosed within the enclosure 25 and liquid 39 is being passed over the body portion 31. In bypass mode, as directed by the user with the controls 155 of the user interface 151 (FIG. 8), the position of the first and second three-way valves 177,179 switch to divert flow of the liquid 39 from the enclosure 25 to the bypass conduit 173. In addition, the outlet pump 161 is turned off during bypass mode, since liquid bypasses the outlet pump. As a result, liquid 39 flows through the first three-way valve 177, the heat exchanger 129, the reservoir 167, the inlet pump 163, the second three-way valve 179 and the bypass line 173. Bypass mode allows the pump apparatus 125 to control the temperature of the liquid 39, without passing the liquid through the enclosure 25. The bypass mode is particularly useful for pre-cooling or pre-heating the liquid 39 within the reservoir 167. This allows the apparatus 21 to prepare the liquid for use before the patient is placed within the enclosure 25.

In operation, the functioning of the liquid delivery system 121 can control the pressure within the interior space 27 of the enclosure by controlling the movement of liquid 39 through the enclosure 25. For example, where the flow rate of the outlet pump 161 is greater than the flow rate of the inlet pump 163, the flow rate difference will create a negative gage pressure, or vacuum, within the interior space 27 of the enclosure 25. Furthermore, a lower pressure within the interior space 27 of the enclosure 25, relative to the exterior of the enclosure, is beneficial in that it (i) draws the enclosure against the body of the patient to maintain the liquid close to the patient's skin, (ii) minimizes leakage of the enclosure, (iii) encourages blood flow to the skin surface, (iv) minimizes the amount of liquid needed to fill the enclosure and (v) allows the patient's body to be manually compressed or decompressed. Decompression may be readily facilitated by the addition of a hook and loop fastener on the outside of the enclosure 25 (not shown), to which medical personnel could attach a mating decompression tool. The negative pressure may be further enhanced by directing the flow of liquid 39 into the bottom of the enclosure 25 and out the top. By requiring the pump to raise the liquid 39 as it passes through the enclosure 25, the pressure drop across the enclosure will increase as flow rates remain constant. A negative pressure within the enclosure 25 creates a gage pressure within the interior space 27 of between about 0 kiloPascal (0 pounds per square inch) and about −14 kiloPascals (−2.0 pounds per square inch). Alternately, positive gage pressure may be maintained within the enclosure 25, as discussed later herein.

The heat transfer liquid 39 has a temperature less than the temperature of the body portion 31 of the patient so that the liquid cools the body portion of the patient. The heat transfer liquid 39 may have a temperature in a range of about 0° C. (32° F.) to about 5° C. (41° F.), such as about 1° C. (34° F.) to about 2° C. (36° F.). Such a temperature range provides adequate cooling while minimizing any adverse affects to the skin of the patient. Heat transfer liquid 39 introduced into the enclosure 25 at such a temperature has been found to cool the body at a sufficient rate to induce hypothermia. Examples of hypothermia inducement in animal subjects are described in greater detail below.

Alternately, the enclosure 25 may be used to warm the body portion 31 of the patient within the enclosure if the heat transfer liquid 39 has a temperature greater than the temperature of the portion of the patient's body. One application of such a warming enclosure 25 would be to warm a patient suffering from unintended hypothermia. The heat transfer liquid may have a temperature in a range of about 37° C. (99° F.) to about 47° C. (117° F.), such as about 45° C. (113° F.).

As described briefly above, the apparatus 21 of the present invention comprises a heat exchanger 129 in fluid communication with the liquid delivery system 121 for altering the temperature of the liquid 39 from an outlet temperature $T_o$, measured after the liquid exits the enclosure 25, to an inlet temperature $T_i$, measured before the liquid enters the enclosure (FIG. 1). After passing through the heat exchanger 129, the liquid 39 may be reintroduced into the enclosure 25 as described above. This allows the same liquid 39 to be used repeatedly between the enclosure 25 and the liquid delivery system 121. Various types of heat exchangers 129 are contemplated as being within the scope of the present invention.

For instance, the heat exchanger 129 of the present invention may incorporate a Peltier device or a phase-change material to facilitate returning the liquid 39 to its inlet temperature after passing through the enclosure 25 and being altered by the temperature of the body portion 31 of the patient. Such a heat exchanger 129 requires a flow rate of at least 1.5 liters per minute (0.40 gallons per minute) to maintain adequate efficiency.

Figure 9:
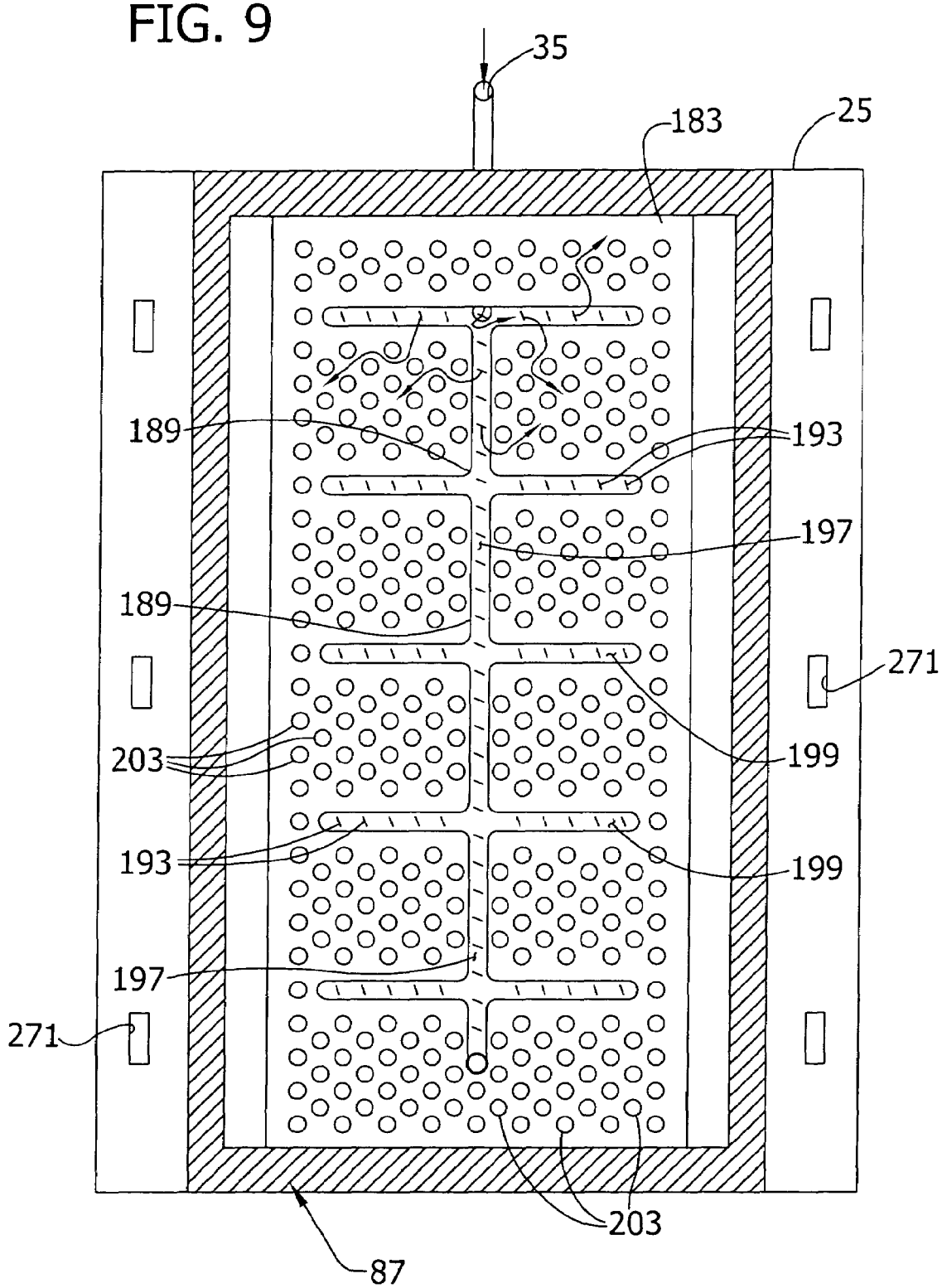
FIG. 9 is a bottom view of the upper member of the apparatus showing liquid passages formed in the apparatus.
Figure 10:
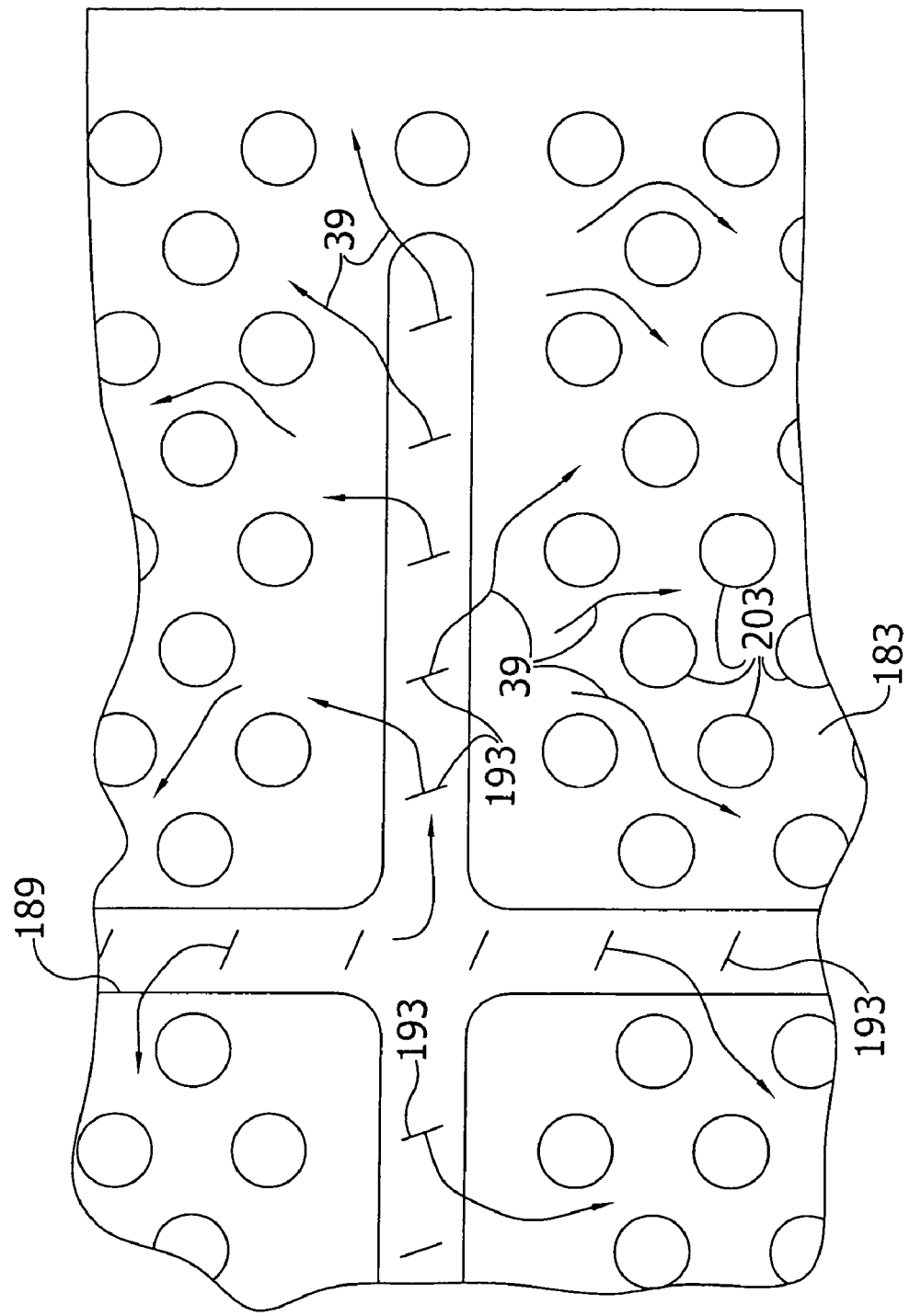
FIG. 10 is an enlarged fragmentary view of the upper member of FIG. 9.
Figure 11:
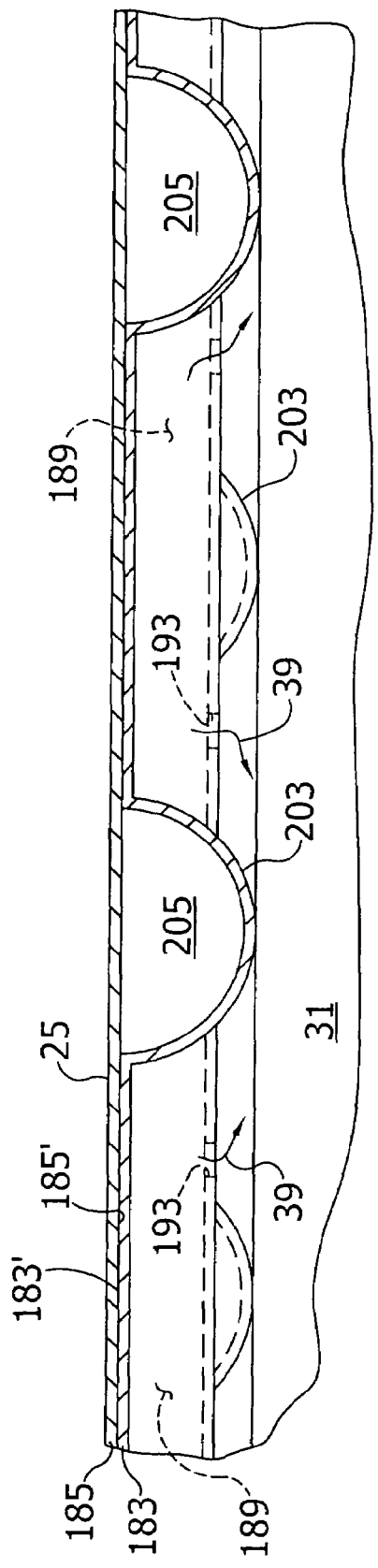
FIG. 11 is a fragmentary side section of the upper member of FIG. 9.

In another embodiment, depicted in FIGS. 9-11, the enclosure 25 comprises a sheet-like body-facing component 183 and a sheet-like outer component 185 that are adapted for face-to-face engagement with one another. The components 183,185 are joined to one another along their facing sides to form at least one liquid passage 189 between the components. The liquid passage 189 is shaped and sized for fluid communication with the inlet 35 for receiving the heat transfer liquid 39. The body-facing component 183 further has at least one opening 193 therein corresponding to the liquid passage 189 for allowing the liquid 39 to pass from the liquid passage to between the body-facing component 183 and the portion of the patient's body 31. Before the liquid passage 189 fills with heat transfer liquid 39, the sheet-like body-facing component 183 and sheet-like outer component 185 of the passage lie flat against one another. Once liquid 39 flows inside the passage 189, the cross-sectional area of the passage increases to allow liquid to flow between the components 183,185. To seal the components together to form the liquid passage 189, heat sealing is used because it provides adequate strength without requiring additional raw materials. Other methods of sealing the components 183,185 to one another, such as adhesives, are also contemplated as being within the scope of the present invention.

The liquid passage 189 of the present configuration may be further configured to distribute liquid 39 over a larger surface area of the patient's body. For example, the liquid passage 189 may comprise at least one main liquid passage 197 extending longitudinally of the enclosure 25, and at least two secondary liquid passages 199 extending laterally out from the main liquid passage. The main liquid passage 197 may branch into many secondary liquid passages 199 to further distribute liquid 39 to the patient's body portion 31 within the enclosure 25. The path of these passages may vary without departing from the scope of the present invention.

Figure 12:
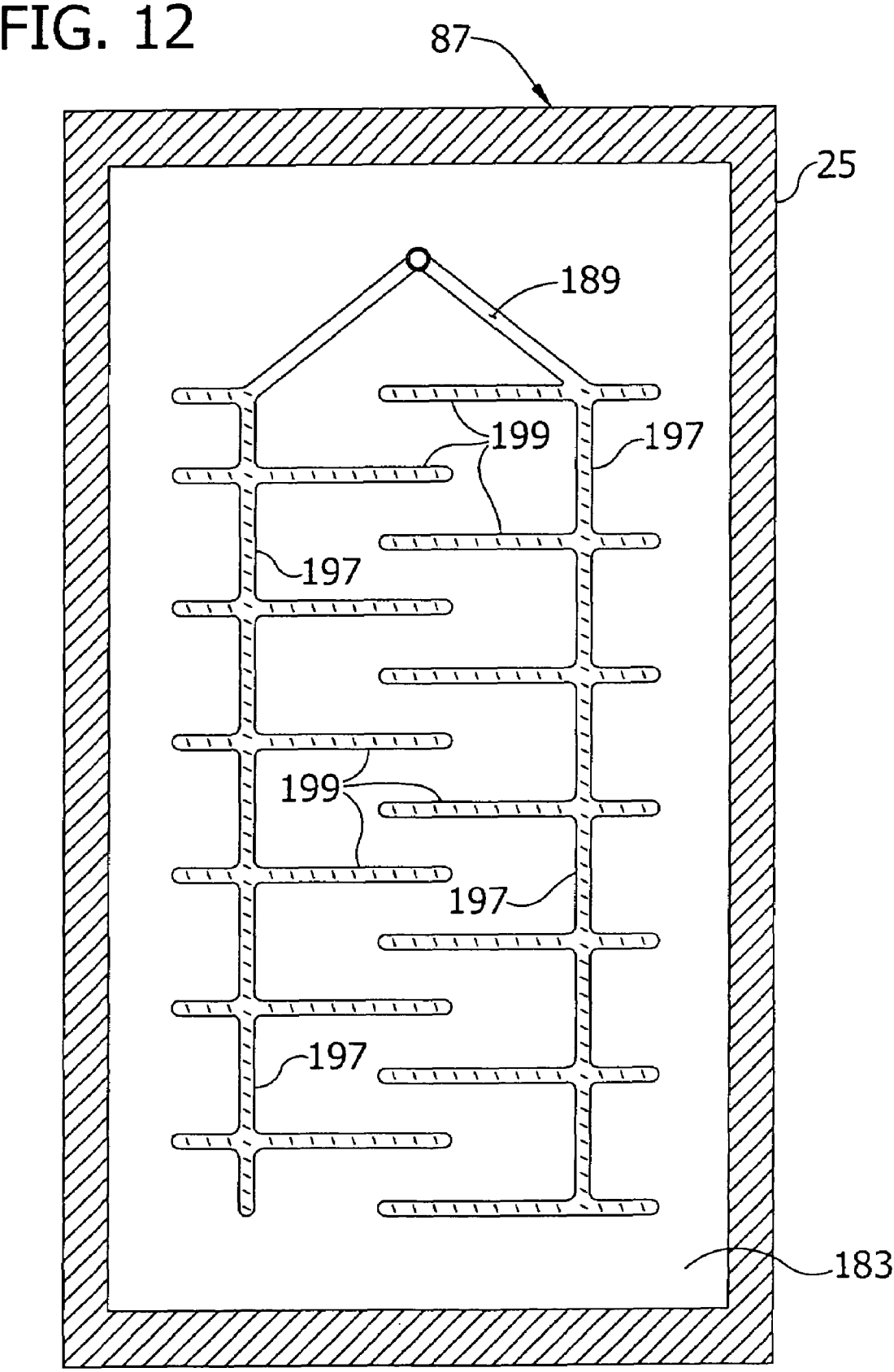
FIG. 12 is a bottom view of a modified upper member of the apparatus shown as having liquid passages formed therein.

The components 183,185 may be joined further along their opposed sides 183',185' to form gas pockets 203. Such pockets 203 are at least partially filled with gas 205 (e.g., air) such that the pockets act as cushions to engage the body portion 31, holding an adjacent portion of the body-facing component 183 slightly away from the body portion of the patient to increase the interior space 27. As the pockets 203 lift and hold the body-facing component 183 away from the patient's body portion 31, they facilitate liquid 39 movement between the body-facing component and the portion of the patient's body. Because the pockets 203 are rounded, their contact area with the patient's body portion 31 is limited, so that more liquid 39 can contact the skin, thereby increasing the heat transfer effect of the liquid. Where the liquid passages 189 extend abundantly throughout the enclosure 25, air pockets 203 may not be necessary for holding the body-facing component 183 slightly away from the patient's body.

Where the torso 53, arms 57 and legs 61 of the patient are within the interior space 27 of the enclosure 25 (e.g., FIG. 1), the main liquid passages 197 are arranged to engage the patient's torso at a position offset from the medial (e.g., longitudinal center) line of the patient's body, as shown in FIG. 12. This feature is particularly useful where CPR is to be administered to the patient, because chest compressions occur generally along the medial line of the patient. Where the patient is placed within the enclosure 25 and the main liquid passage 197 corresponds approximately with the medial line of the patient, chest compressions may systematically block the flow of liquid 39 through the main liquid passage, thereby reducing liquid flow through the enclosure 25. Where the main liquid passages 197 are offset from the medial line of the patient as shown in FIG. 12, chest compressions performed in rendering CPR treatment are less disruptive of liquid 39 flow through the enclosure 25. Although not shown in FIG. 12, gas pockets 203, as disclosed previously, may be incorporated into the present configuration. Other passage arrangements are also contemplated as being within the scope of the present invention.

A further embodiment of the present invention includes a portable control unit 117 comprising the liquid delivery system 121, a user interface 151, a power source 211 and the control system 135 for powering and controlling the liquid delivery system (FIG. 1). Such a portable control unit 117 would be particularly useful where the apparatus 21 is to be used at a remote site, where electricity is unavailable. Moreover, the self-contained nature of the portable control unit 117 allows it to be carried to the patient, administered to the patient and remain operational while the patient is transported to a medical facility. In one embodiment, the power source 211 is a battery. Other portable power sources, such as engine-based generators and motorized vehicles (e.g., electrical power derived from either) are also contemplated as potential sources of power. In order for the control system 135 to properly control the flow of liquid 39 through the enclosure 25 to control the body temperature of the patient, the temperature sensors 131 of the portable control unit engage the patient's body 31 via wires 133 to monitor the temperature of the patient. Inputs from these temperature sensors 131 feed into the control system 135 for monitoring and controlling the temperature of the patient.

In another embodiment, controlling the liquid delivery system 121 can control the fluid pressure within the enclosure by controlling the flow of liquid 39 through the enclosure 25. For instance, where the flow rate generated by the outlet pump 161 is less than the flow rate generated by the inlet pump 163, the flow rate differential will create a positive gage pressure, e.g., greater than atmospheric pressure, within the interior space 27 of the enclosure 25. Pressurizing the interior space 27 generally applies a compressive force to the patient's body portion 31 as the heat transfer liquid 39 flows over the patient. The positive gage pressure within the interior space 27 may be between about 0 kiloPascals (0 pounds per square inch) and about 28 kiloPascals (4 pounds per square inch).

However, without restraining the size of the enclosure 25, a positive gage pressure within the interior space 27 would tend to expand the enclosure as more liquid 39 enters the unrestrained enclosure. Thus, several embodiments are contemplated for limiting such outward expansion of the enclosure 25 under positive internal pressure. For example, at least one strap 215 may surround the exterior of the enclosure 25 to inhibit or otherwise limit outward expansion of the enclosure and exerting pressure upon the body portion 31 within the enclosure (e.g., FIG. 7). The strap 215 may further be selectively positionable for engagement with particular portions of the enclosure 25 in contact with particular portions of the patient's body 31 to apply pressure in a particular area. This feature may be particularly useful where the patient is bleeding and pressure upon a specific area may inhibit further bleeding.

Figure 13:
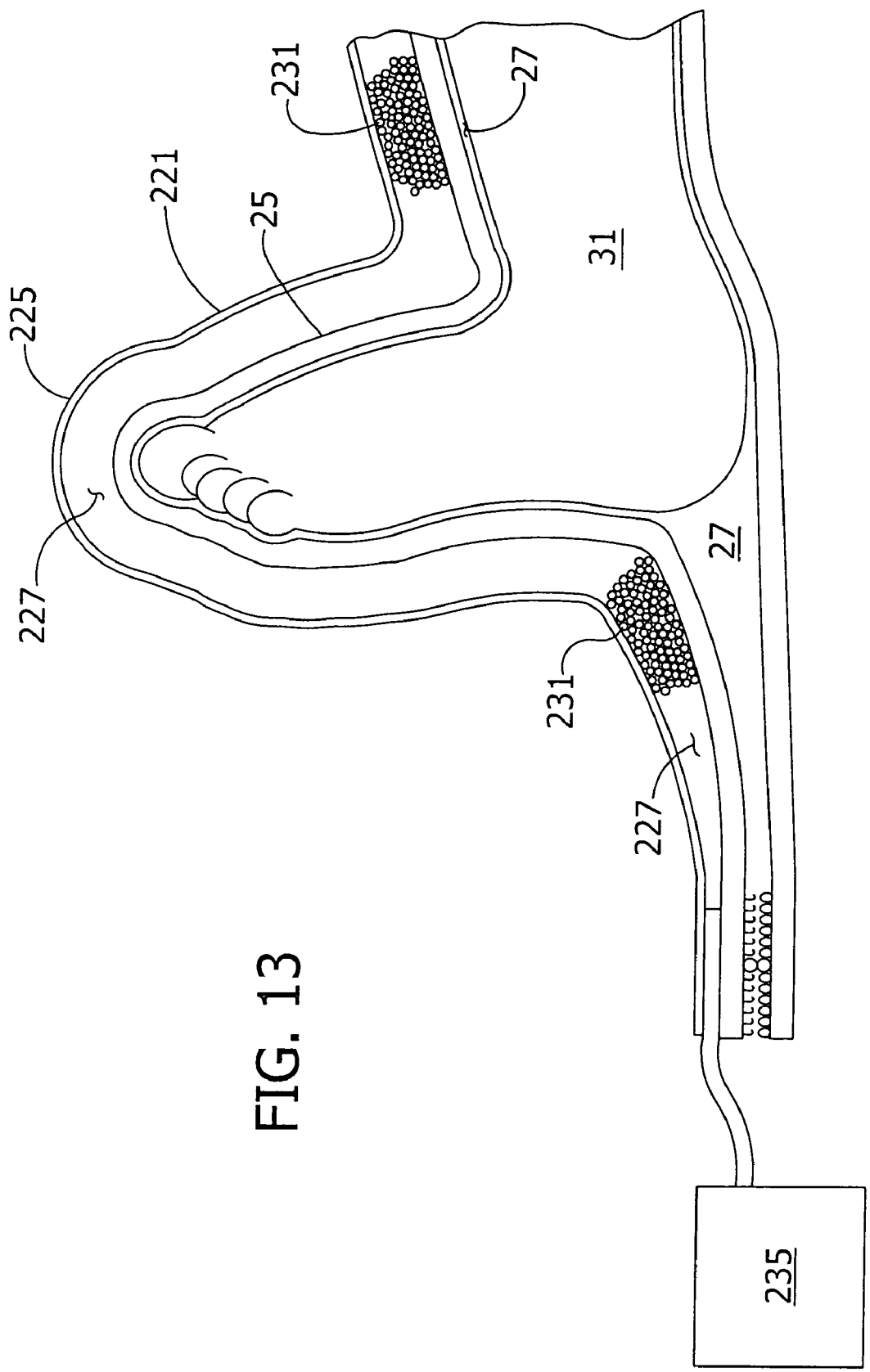
FIG. 13 is a fragmentary section of an apparatus having a jacket with a rigidifiable layer.
Figure 14:
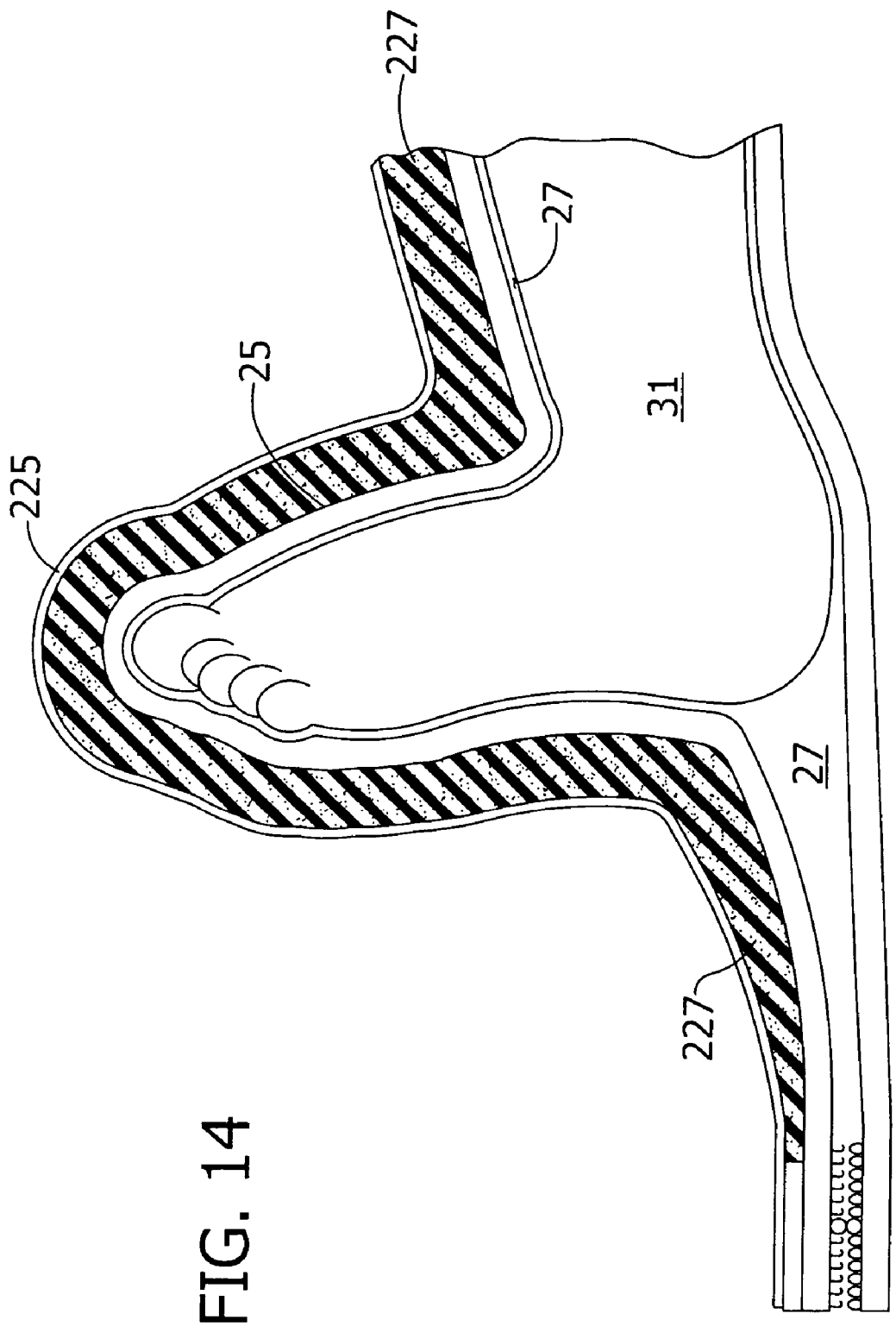
FIG. 14 is a fragmentary section of a second embodiment of apparatus of the present invention having a jacket with a rigidifiable layer.

Referring now to FIGS. 13 and 14, expansion of the enclosure 25 may also be limited by a jacket 221 surrounding the enclosure. The jacket 221 is less elastic than the enclosure 25 and adapted to resist expansion of the enclosure upon pressurizing the interior space 27. The jacket 221 is formed from a material resistant to expansion to thereby generally maintain the shape of the pressurized enclosure 25. For example, a suitable jacket 221 may be constructed from a rigid plastic such as polycarbonate, Acrylonitrile Butadiene Styrene (ABS) or acrylic. This jacket 221 may incorporate reinforcing fibers made of a high tensile strength material such as KEVLAR®, a federally registered mark of E. I. du Pont de Nemours and Company of Wilmington, Del., U.S.A., graphite or glass. Alternately, the jacket 221 may comprise an outer member 225 and a rigidifiable layer 227 between the outer member and the enclosure 25. The rigidifiable layer 227 need not be completely rigid, but is less elastic than the enclosure 25 to limit expansion of the enclosure upon pressurizing the interior space 27. In one configuration, the rigidifiable layer 227 comprises small particulate matter 231, such that the rigidifiable layer may be placed in fluid communication with a vacuum source 235 for removing gas (e.g., air) from between the individual particles of particulate matter, thereby rigidifying the rigidifiable layer between the jacket 221 and enclosure 25 by compacting and densifying the particles with respect to one another (FIG. 13). Once the rigidifiable layer 227 is rigidified, a positive gage pressure may be maintained within the enclosure 25, while limiting further expansion of the enclosure. One suitable particulate matter 231 is polystyrene beads, for example. The rigidifiable layer 227 is shown in FIG. 13 without particulate matter 231 throughout the layer to simplify the figure, although the rigidifiable layer may be fully filled with such matter in actual use. Instead of particulate matter, the rigidifiable layer 227 may comprise a polymer capable of starting as a non-solid and solidifying due to a chemical reaction (FIG. 14). For example, a polymer such as two-component, foam-in-place polyurethane may be used to rigidify the rigidifiable layer 227.

Figure 15:
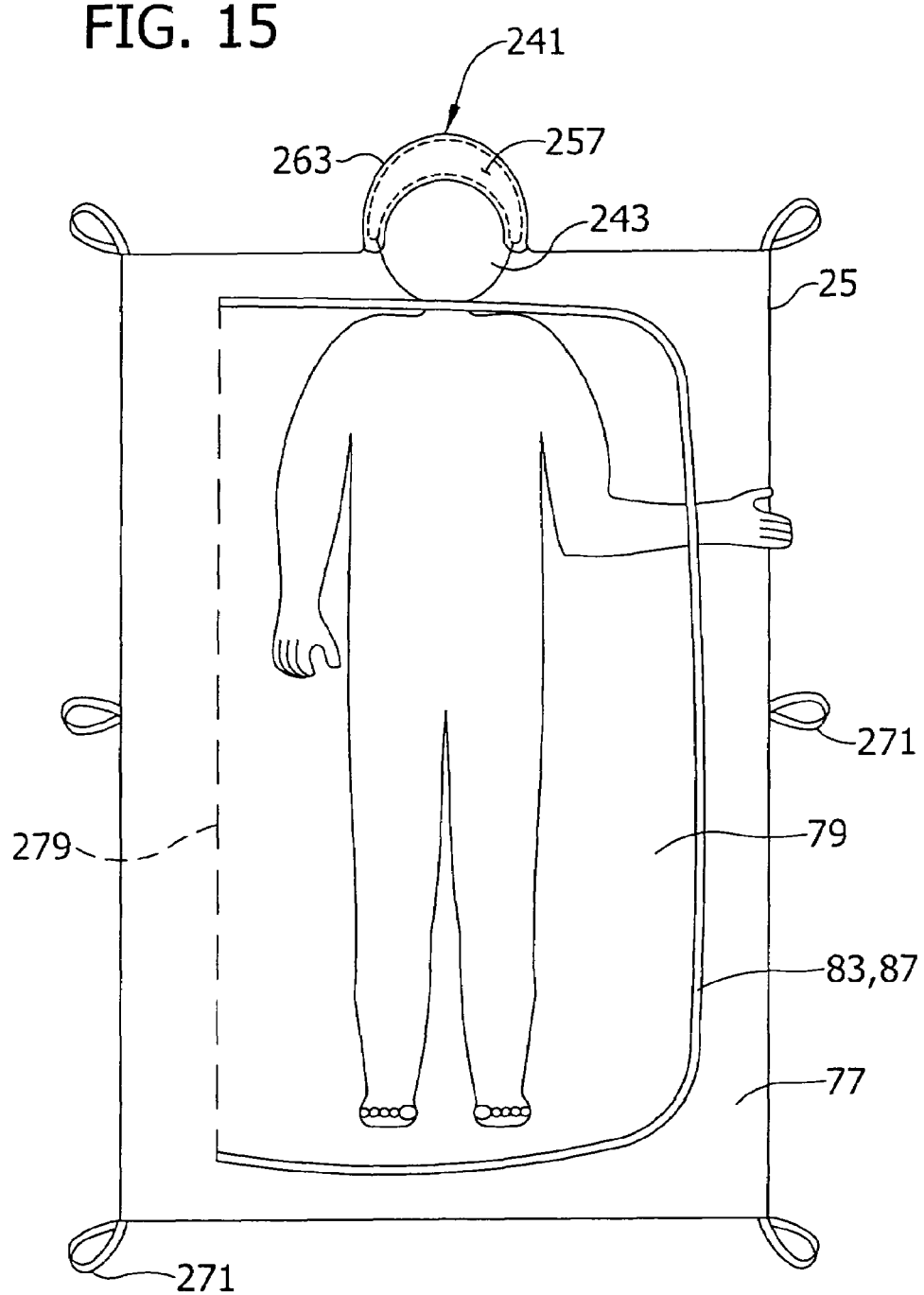
FIG. 15 is a top plan view of a third embodiment of apparatus of the present invention.

With reference to FIG. 15, the apparatus 21 further comprises a head cooling device, generally indicated at 241, engaging the head 243 of the patient for circulating the heat transfer liquid 39 in contact with the head of the patient (FIGS. 1 and 2). The head cooling device 241 further comprises an inlet 247, providing a path for entry of liquid 39 for directly contacting the head 243, and an outlet 249, providing a path for exhausting liquid from the head cooling device. In one embodiment, the head cooling device 241 comprises a helmet 253 for placement upon the head 243 of the patient (FIGS. 1 and 2). The helmet 253 is adapted for sealing engagement with the head 243 of the patient. The helmet 253 is shaped such that the interaction of the helmet and the head 243 form a void 257 so that the heat transfer liquid 39 may flow through the void and contact the head to alter the temperature of the head. In another configuration, the head cooling device 241 comprises a hood 263 attached to the enclosure 25 and wrapping about the head 243 of the patient (FIG. 15). The hood 263 also cooperates with the head 243 to form a void 257 between the hood and the head, thereby allowing the heat transfer liquid 39 to contact the patient's head.

In addition to the head cooling device 241, a mask 267 is adapted for placement over the face of the patient to deliver air to the mouth or nose of the patient via tubing 269 (FIG. 1). The mask 267 may deliver ambient air or oxygen to the patient, as would a conventional breathing mask, or the air delivered through the mask may be at a temperature different than the temperature of the patient's body to aid in cooling or warming the patient.

Additionally, at least a portion of the upper member 79, and possibly the entire upper member, may be transparent for viewing the body portion 31 within the enclosure 25. For instance, a sheet-like body-facing component and sheet-like outer component (as described above) may be formed from a transparent material, such as PVC (polyvinyl chloride), polyethylene or polyurethane.

Referring now to FIGS. 9 and 15, the enclosure 25 may further comprise handles 271 for lifting the enclosure with the body portion 31 received within the enclosure. Such handles 271 may be attachable to the enclosure 25 or formed integrally with the enclosure. For instance, handles 271 may be formed integrally with the lower member, as shown in FIG. 9. Handles 271 provide ease of movement of the enclosure 25, allowing the patient and enclosure to be easily lifted and moved to another location, while heat transfer liquid 39 continues to flow through the enclosure for altering the temperature of the patient.

In another embodiment, depicted in FIG. 15, the upper member 79 is hinged to the lower member 77 along an edge 279 of the upper member. This ensures that the upper member 79 and lower member 77 remain attached and properly aligned for use with respect to one another. In this configuration, the upper member 79 is slightly smaller than the lower member 77. This allows the sealing portions 83,87 of the enclosure 25 to lie laterally inward from the peripheral edge of the lower member 77 of the enclosure.

Figure 16:
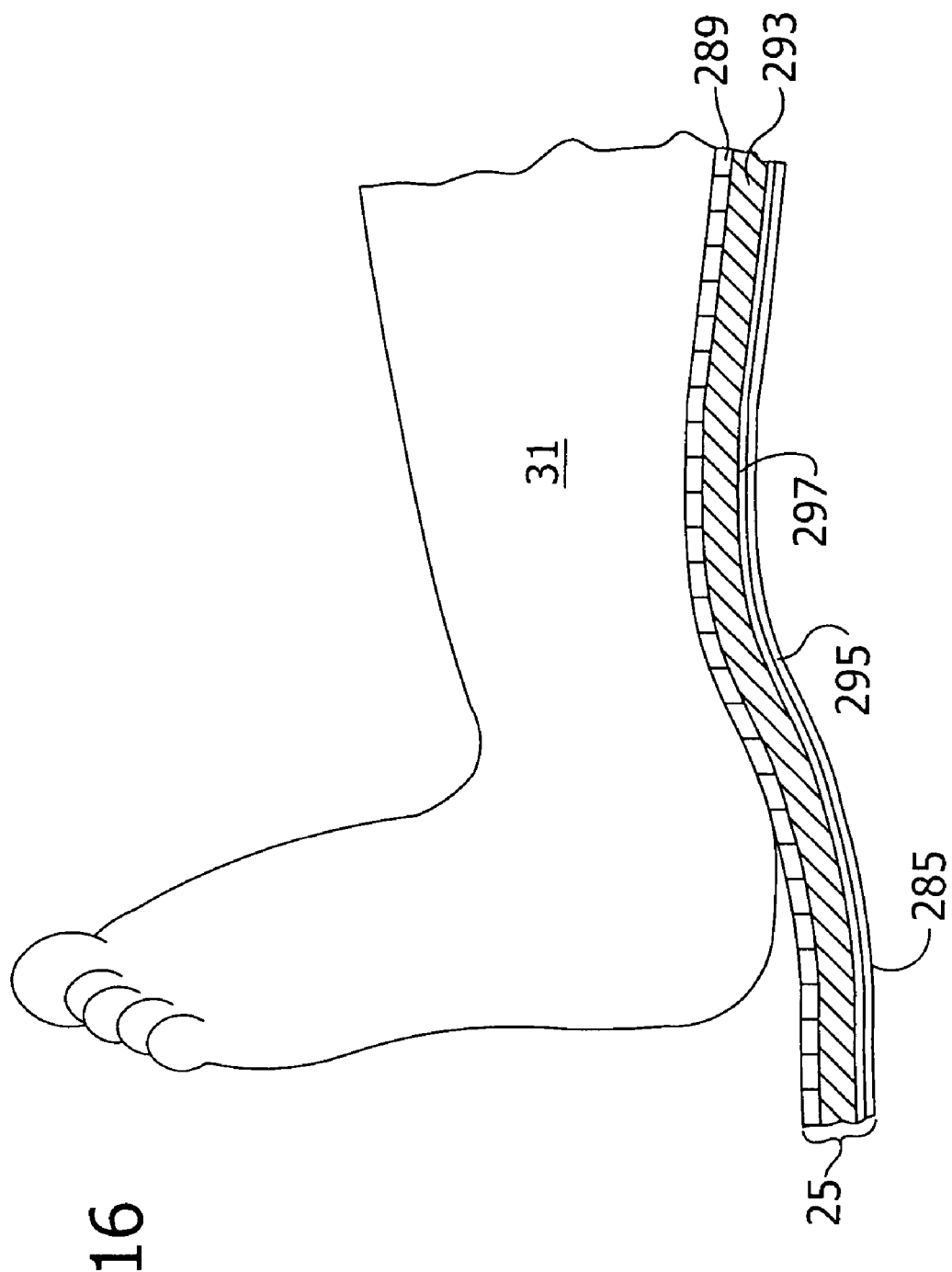
FIG. 16 is an enlarged fragmentary elevation of the enclosure of FIG. 2.

Referring now to FIG. 16, the enclosure 25 of the present invention comprises a liquid impermeable outer layer 285 and a porous layer, such as a layer of batting 293. The liquid impermeable outer layer 285 retains the heat transfer liquid 39 within the enclosure 25, while the porous batting layer 293, which is a substantially hydrophobic material and comprises a matrix of fibers, allows liquid to pass from the batting into contact with the patient's body portion 31 for flow across the skin throughout the enclosure. In addition, a mesh body-facing layer 289 may be used to hold the batting layer 293 in place, allowing substantial contact between the body portion 31 and the liquid 39 within the batting layer. In one configuration, the liquid impermeable outer layer 285 further comprises a neoprene outer shell 295 with an inner layer 297 of aluminum laminated polyester. The outer shell 295 of neoprene repels liquid, while the inner layer 297 helps insulate the enclosure 25. The outer shell 295 comprises about 3.2 mm (0.125 inch) to about 1.6 mm (0.0625 inch) thick Neoprene, which is commercially available from John R. Sweet Co. of Mustoe, Va., USA. The inner layer 297 comprises Aluminum Laminated Polyethylene, which is commercially available from Wal-Mart Stores, Inc. of Bentonville, Ark., USA. In another configuration, the outer layer 285 comprises a transparent material such as PVC (polyvinyl chloride), polyethylene or polyurethane that permits the body portion 31 to be seen through the enclosure 25. The middle layer of batting 293 comprises polyester batting, and the mesh layer 289 comprises a nylon screen. For example, the layer of batting 293 may be rich loft polyester batting, such as is available from Carpenter Co. of Taylor, Tex., USA. The mesh layer 289 is a Nylon screen mesh, such as is available from McMaster-Carr Supply Company of New Brunswick, N.J., USA. Because each of these components is relatively thin, the enclosure 25 may be folded or rolled into a compact shape for ease of storage. The total thickness of each member 77, 79 of the enclosure is less than about 5 mm (0.2 inch).

In one embodiment of a method of the present invention for controlling the body temperature of a patient, at least a portion 31 of the patient's body substantially sealingly enclosed within the interior space 27 of an enclosure 25. The enclosure 25 is generally contiguous with the portion 31 of the patient's body. The method further comprises directing a heat transfer liquid 39 to flow within the interior space 27 in direct liquid contact with the patient's body to promote heat transfer between the heat transfer liquid and the patient's body. Specifically, the method comprises directing the heat transfer liquid 39 to flow from an inlet 35 of the enclosure 25 through the interior space 27 of the enclosure to an outlet 45 thereof. The method may further comprise maintaining heat transfer liquid 39 in contact with the patient's body within the interior space 27 between the enclosure inlet 35 and the enclosure outlet 45. Such a method may also comprise positioning the patient's body generally within the interior space 27 between the enclosure inlet 35 and the enclosure outlet 45, such that the enclosure inlet and enclosure outlet are disposed on generally opposite sides of the patient's body. In addition, the step of directing heat transfer liquid 39 to flow through the interior space 27 of the enclosure 25 may comprise generating a negative pressure within the interior space of the enclosure. The method may further comprise the step of applying a compressive force to the patient's body as heat transfer liquid 39 is directed to flow through the interior space 27 of the enclosure 25.

The method may further comprise the step of performing CPR upon the patient simultaneous with the directing step described above. With prior systems for cooling or heating the patient's body, cooling and heating had to be temporarily stopped during resuscitation. With the method of the present invention, CPR does not interfere with the heating or cooling of the patient.

In still another embodiment, a method for controlling the body temperature of a patient comprises the steps of enclosing at least a portion of the patient's body within the interior space 27 of an enclosure 25 with the enclosure being generally contiguous with at least opposite sides of the portion 31 of the patient's body. The method further comprises directing a heat transfer liquid 39 to flow within the interior space 27 in direct liquid contact with at least the opposite sides of the portion of the patient's body to promote heat transfer between the heat transfer liquid and the patient's body.

Figure 19:
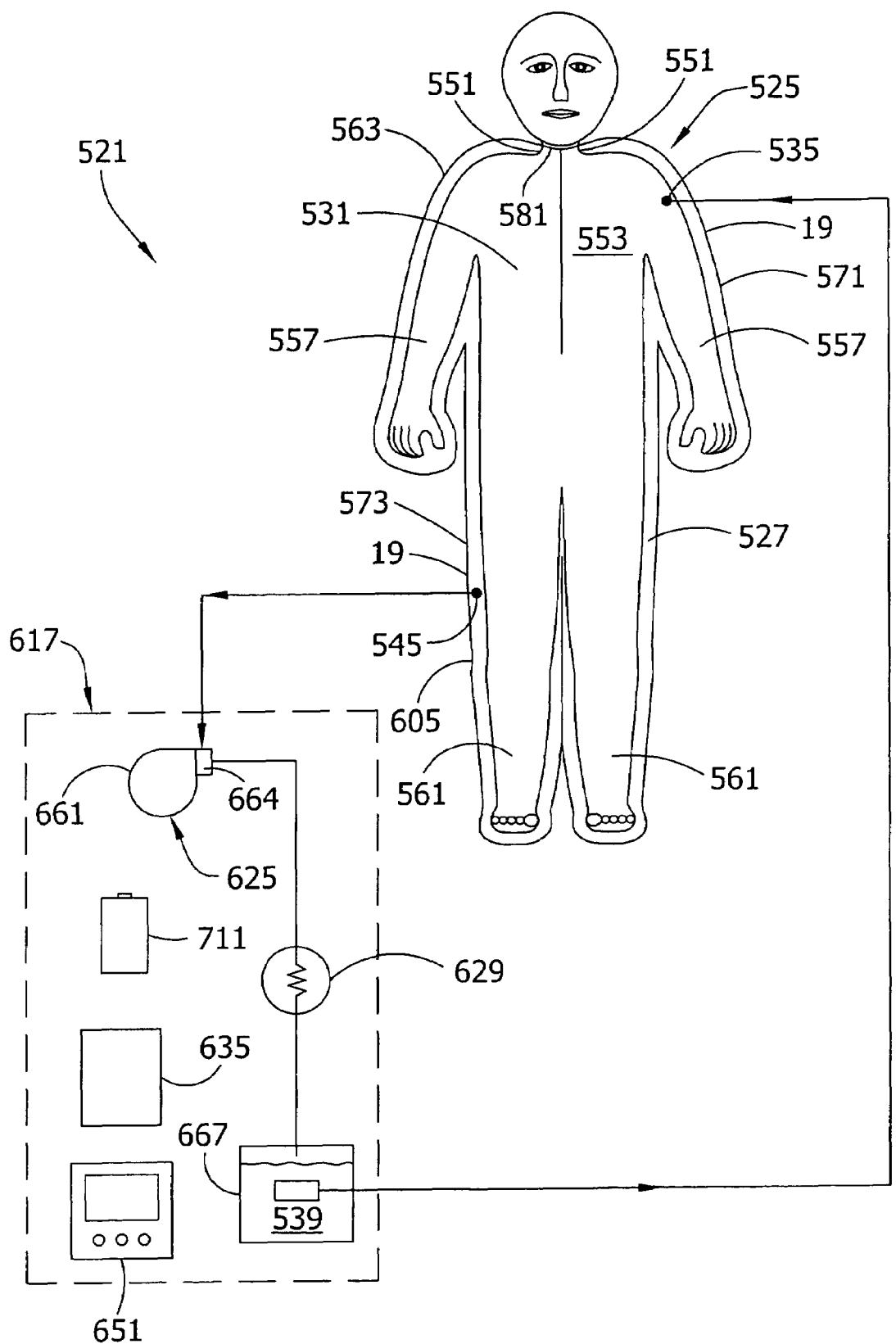
FIG. 19 is a schematic of a fourth embodiment of apparatus of the present invention for altering the body temperature of a patient.

Referring to FIGS. 19-30, and particularly to FIG. 19, reference number 521 generally indicates a fourth embodiment for adjusting the body temperature of a patient. As mentioned above, the apparatus of the present invention generally comprises an enclosure, generally indicated at 525, defining an interior space 527 for receiving at least a portion 531 of a patient's body therein. The enclosure 525 is configured for substantially sealingly enclosing the portion 531 of the patient's body (illustrated in FIG. 19 as all of the patient's body below the head) within the interior space 527 with the enclosure generally contiguous with the patient's body. An inlet 535 of the enclosure 525 is adapted to receive heat transfer liquid 539 into the enclosure. The inlet 535 is further in fluid communication with the interior space 527 of the enclosure 525 to direct heat transfer liquid 539 into the interior space for flowing over the patient's body portion 531 in direct contact therewith to promote heat transfer between the patient's body portion and the heat transfer liquid. The enclosure 525 also has an outlet 545 in fluid communication with the interior space 527 of the enclosure for exhausting the heat transfer liquid 539 from the enclosure.

The enclosure 525 is adapted to generally conform to the portion 531 of the patient's body disposed within the interior space 527. Although any portion of the patient's body may be placed inside the enclosure, the enclosed portion may include a part of the patient's body below the head, such as at least one part of the body of the patient selected from a group including the torso 553, arms 557, and legs 561. Accordingly, alternative garment-type embodiments include a jumpsuit 563 (FIG. 20A) for enclosing all of the patient's body below the head, a shirt 565 (FIG. 20B) for enclosing the torso and arms of the patient, a vest 567 (FIG. 20C) for enclosing the torso of the patient and a pair of pants 569 (FIG. 20D) for enclosing the lower torso and legs of the patient. The enclosure 525 can have other configurations, shapes, or sizes for enclosing other body portions without departing from the scope of the invention.

Referring again to FIG. 19, the enclosure 525 comprises a first portion 571 and a second portion 573 in sealing engagement with one another to form the interior space 527 for receiving the body portion 531. In one version, the first and second portions 571, 573 comprise an impermeable sheet. In another version, the first and second portions 571, 573 comprise a liquid impermeable outer layer 285, a mesh body-facing layer 289 and a layer of batting 293 between the outer layer and the body-facing layer (FIG. 16). The impermeable layer 285, mesh body-facing layer 289 and a layer of batting 293 between the outer layer and body-facing layer are substantially the same as or equivalent to those described previously herein.

The first portion 571 and the second portion 573 illustrated in FIG. 19 cooperate to form a neck opening 581 in the enclosure 525. The neck opening 581 is sized and shaped for sealing engagement of the portions 571, 573 with the neck 551 of the patient at the opening. In addition, as shown in FIGS. 20A, 20B and 20D, there are various possible configurations of the hand regions, generally indicated at 575, and foot regions, generally indicated at 577, of the garment-type enclosures. As illustrated, the hand and foot regions 575, 577 of the jumpsuit 563, shirt 565 or pants 569 embodiments can be enclosed. Alternatively, the hand and/or foot regions 575, 577 can have barrier cuffs 579 adapted for sealing against the portion of the patient's body received within the interior space of the enclosure that allow of the patient's hand or foot to extend outside on the enclosure. Similar barrier cuffs 579 may be used, for example, to seal the neck opening 581 of the various enclosures against the neck of the patient, to seal the waist opening 583 of the vest 567, shirt 565 or pants 569 enclosures against the waist of a user, and to seal the arm openings 585 of the vest 567 enclosure against the upper arm of a user.

Figure 21A:
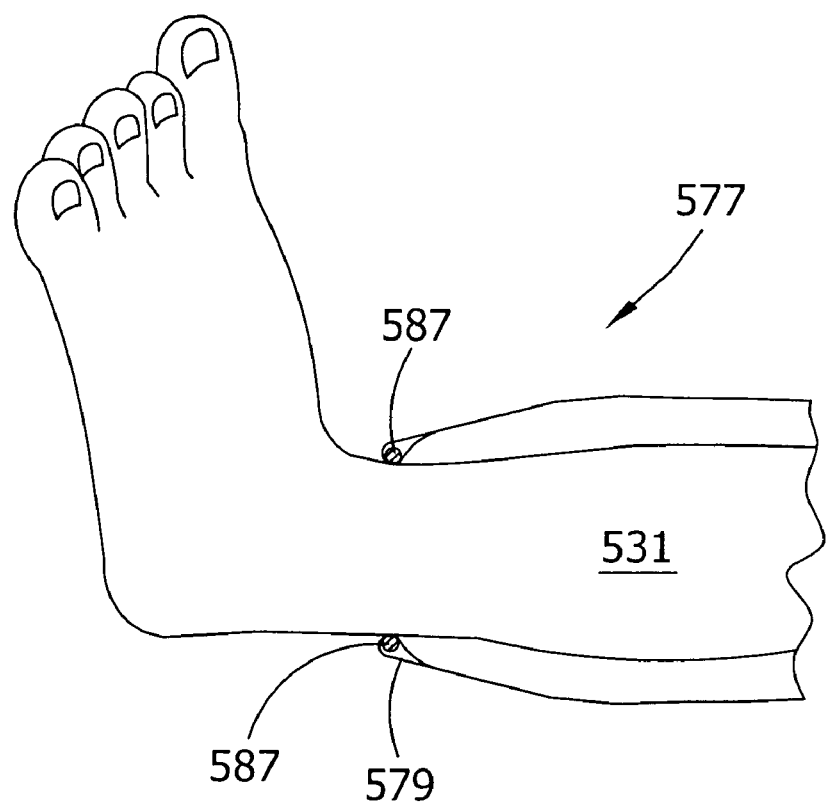
FIG. 21A shows a barrier cuff having an elastic member for sealing the barrier cuff against a portion of a patient's body.
Figure 21B:
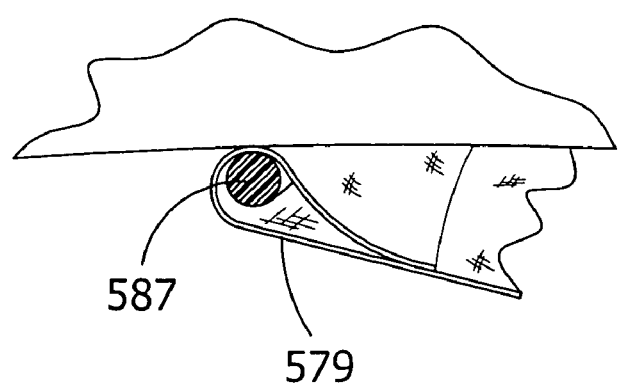
FIG. 21B shows an enlarged view of the elastic member of the barrier cuff of FIG. 21A.
Figure 22A:
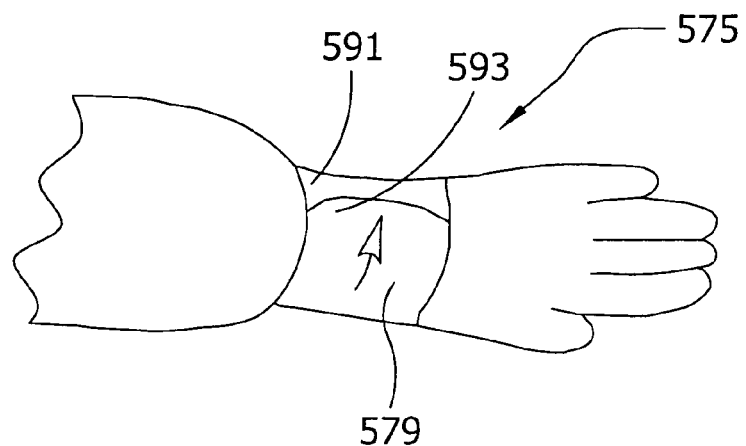
FIG. 22A shows a modified barrier cuff having an adhesive tab for adjusting and securing the barrier cuff against a portion of the patient's body.
Figure 23A:
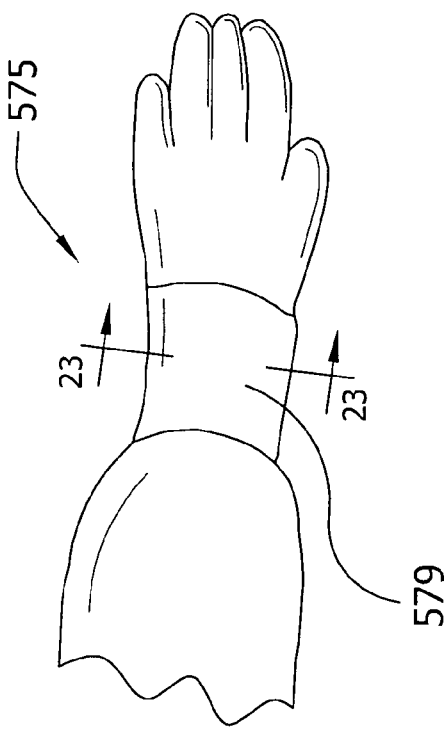
FIG. 23A shows yet another barrier cuff having an inflatable bladder.

As shown in FIGS. 21A, 22A and 23A, the barrier cuff 579 is positioned adjacent the opening (i.e. neck, waist, foot or arm) for encircling a part of the portion 531 of the patient's body enclosed within the interior space 527 thereby creating a liquid impervious seal. Referring to FIGS. 21A and 21B, the barrier cuff 579, in one version, comprises elastomeric material 587, such as at least one stretchable band (broadly, "elastic member"), urging the barrier cuff to collapse inward around the opening for sealing engagement with the portion 531 of the patient's body.

Figure 22B:
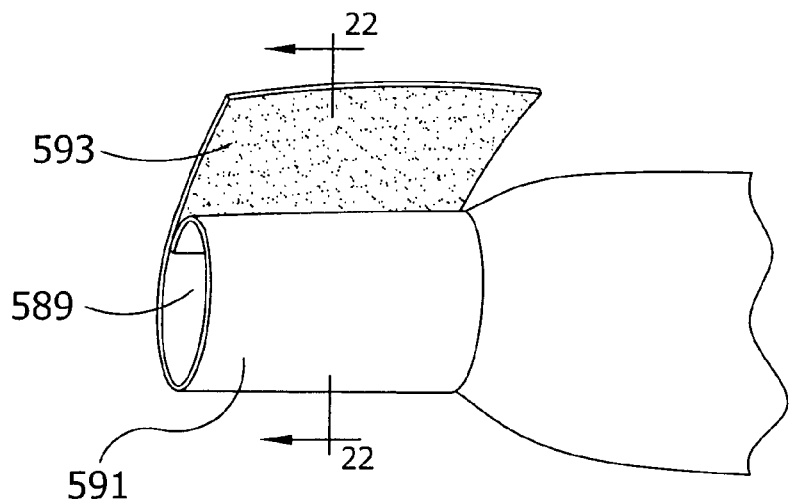
FIG. 22B is a perspective view of the barrier cuff shown in FIG. 22A in an unsealed position.
Figure 22C:
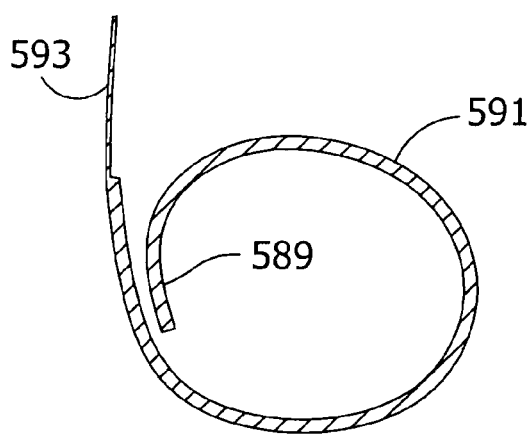
FIG. 22C is a section on line 22-22 of FIG. 22B.
Figure 22D:
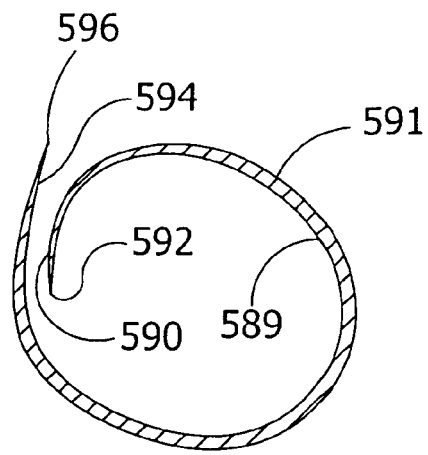
FIG. 22D is a section showing an alternative barrier cuff with a tapered overlapped portion and an overlapping portion.

Another version of the barrier cuff, shown in FIGS. 22A-22C, comprises an inner barrier 589 for engaging the portion of the patient's body, an outer barrier 591 comprising a liquid impervious sheet affixed to the inner barrier and at least one tab 593 secured to the outer barrier. The tab 593 is adapted for selectively sizing the barrier cuff 579 to seal the portion 531 of the patient's body within the enclosure 525. The inner barrier 589 is a foam gasket sized and shaped for conforming to and sealing with the part of the portion of the patient's body. The tab 593 comprises an adhesive tab adapted for being pulled thereby tightening the outer barrier 591 against the inner barrier 589 and thus, the inner barrier against the portion of the patient's body positioned within the enclosure and for securing the tab to the outer barrier thereby holding the inner barrier and outer barrier in a sealing engagement position. In yet another configuration, the inner and outer barriers 589, 591 both comprise a unitary foam gasket, such as a gasket formed from polyvinyl chloride, sized and shaped for conforming to and sealing with the part of the portion of the patient's body (FIG. 22D). The gasket is adapted to selectively encircle and engage the part of the portion of the patient's body. The gasket has a overlapped portion 590 extending from a first edge 592 of the gasket and an overlapping portion 594 extending from an opposite second edge 596 of the gasket. The overlapping portion 594 is adapted to engage and overlap the overlapped portion 590. The overlapped portion is inclined in a direction from the first edge 592 thereby providing a smooth, sloped surface for engagement with the overlapping portion 594. Either or both the overlapping portion 594 and the overlapped portion 590 may include an adhesive for securing the overlapping and overlapped portions together. The sloped surface of the overlapped portion 590 avoids the step (not shown) created when two pieces of material with generally rectangular cross-sections are overlapped. The step could be a point of leakage.

Figure 23C:
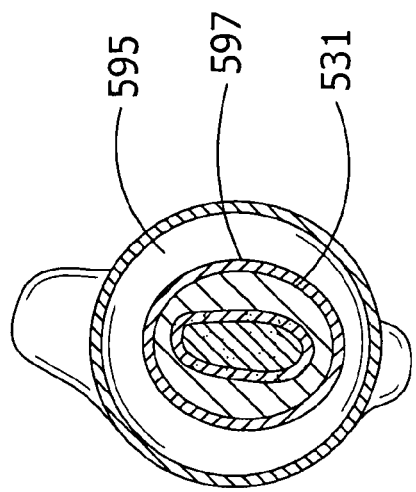
FIG. 23C is the section of FIG. 23A showing the barrier cuff in a sealing position.
Figure 23B:
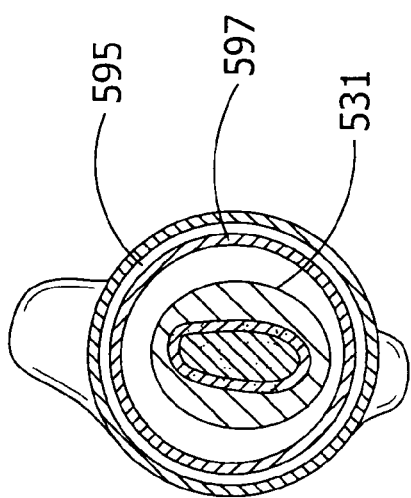
FIG. 23B is a section on line 23-23 of FIG. 23A showing the barrier cuff in a unsealed position.

In another configuration, the inner barrier may be a bladder 595 within a collar 597 (FIGS. 23A-23C). The bladder 595 is adapted to expand for conforming and sealing the collar 597 with the part of the portion 531 of the patient's body positioned within the enclosure 525. The bladder 595 of one embodiment is a pneumatic bladder. Other types of barrier cuffs can be used without departing from the scope of this invention.

Figure 24:
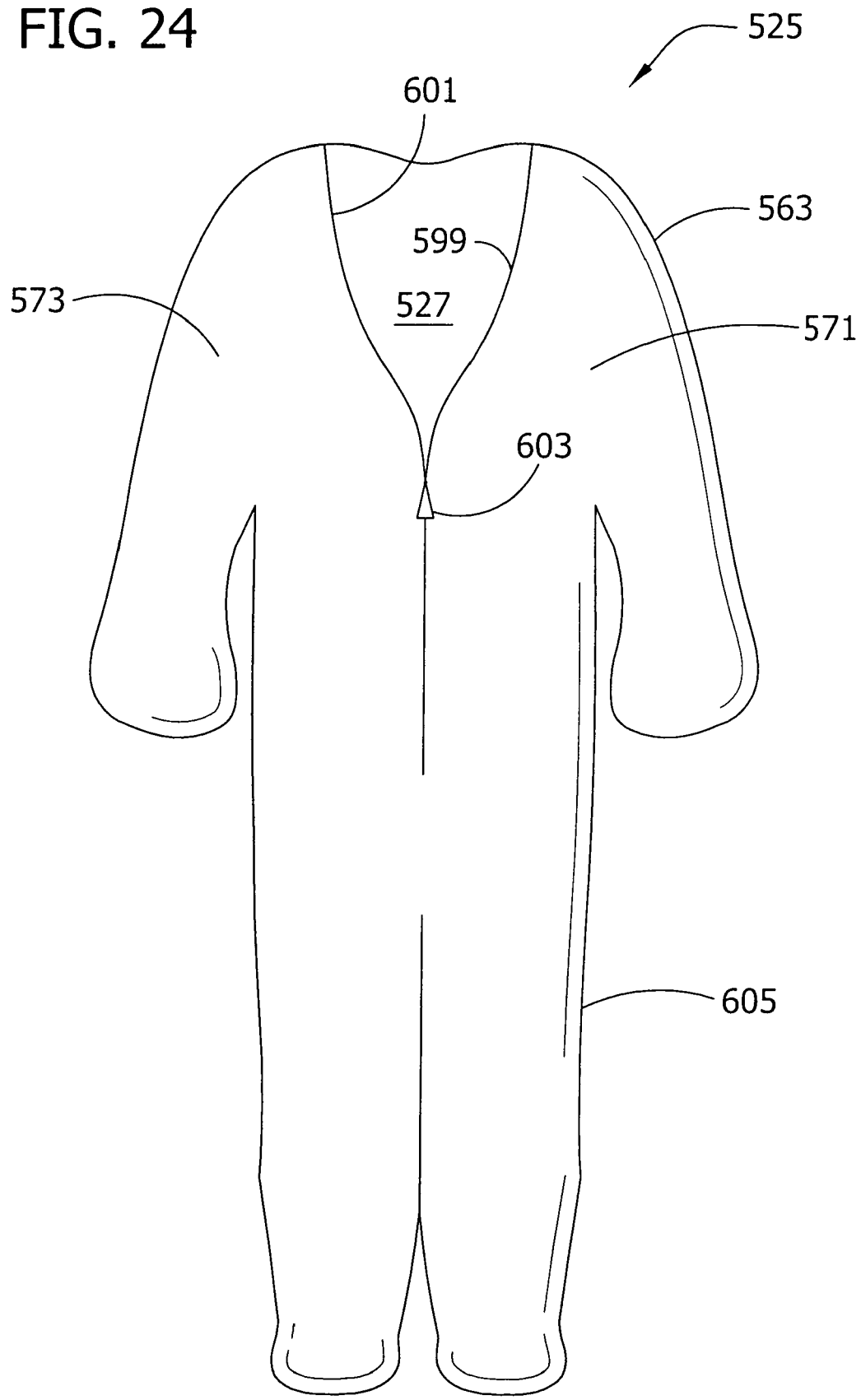
FIG. 24 shows an enclosure having a slide fastener for selectively enclosing a portion of a patient's body within the enclosure.

Referring to FIG. 24, the first portion 571 includes a first sealing portion 599, and the second portion 573 includes a second sealing portion 601. The sealing portions comprise slide fastener members, such as the FLEXIGRIP® 7 manufactured by MiniGrip/ZIP-PAK®, an ITW Company, of Orangeburg, N.Y., USA, which are selectably sealingly engageable with one another for sealing an opening into the interior space 527 of the enclosure 525 using a slide fastener 603. This seal inhibits liquid leakage from the enclosure 525, or a loss of pressure within the interior space 527 of the enclosure.

In the embodiment illustrated in FIG. 19, the inlet 535 extends through the first portion 571 and the outlet 545 extends through the second portion 573. When donned by a patient, one of the portions 571, 573 is disposed adjacent one side of the body portion 531 of the patient and the other portion adjacent the other side of the body portion, thereby arranging the inlet 535 and the outlet 545 on opposite sides of the patient. The first and second portions 571, 573 are configured to receive the left side and right side of the patient's body, respectively. The first and second portions 571, 573 may be have other configurations without departing from the scope of this invention such as being adapted to receive the front and back sides of the patient's body portion 531.

Figure 25:
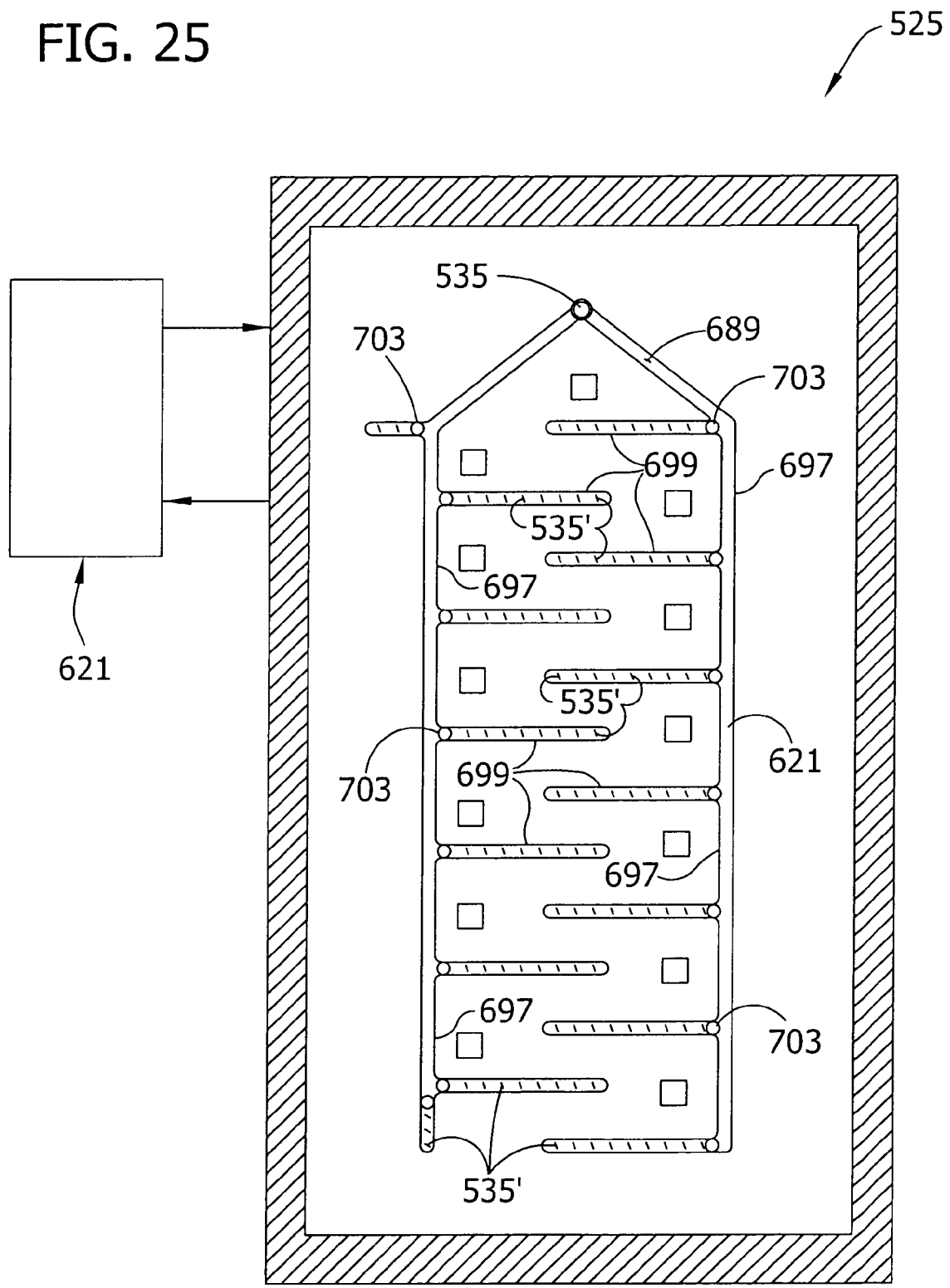
FIG. 25 is a schematic of a control unit integrated with a valve control system and sensors for distributing the heat transfer liquid within the enclosure.
Figure 26:
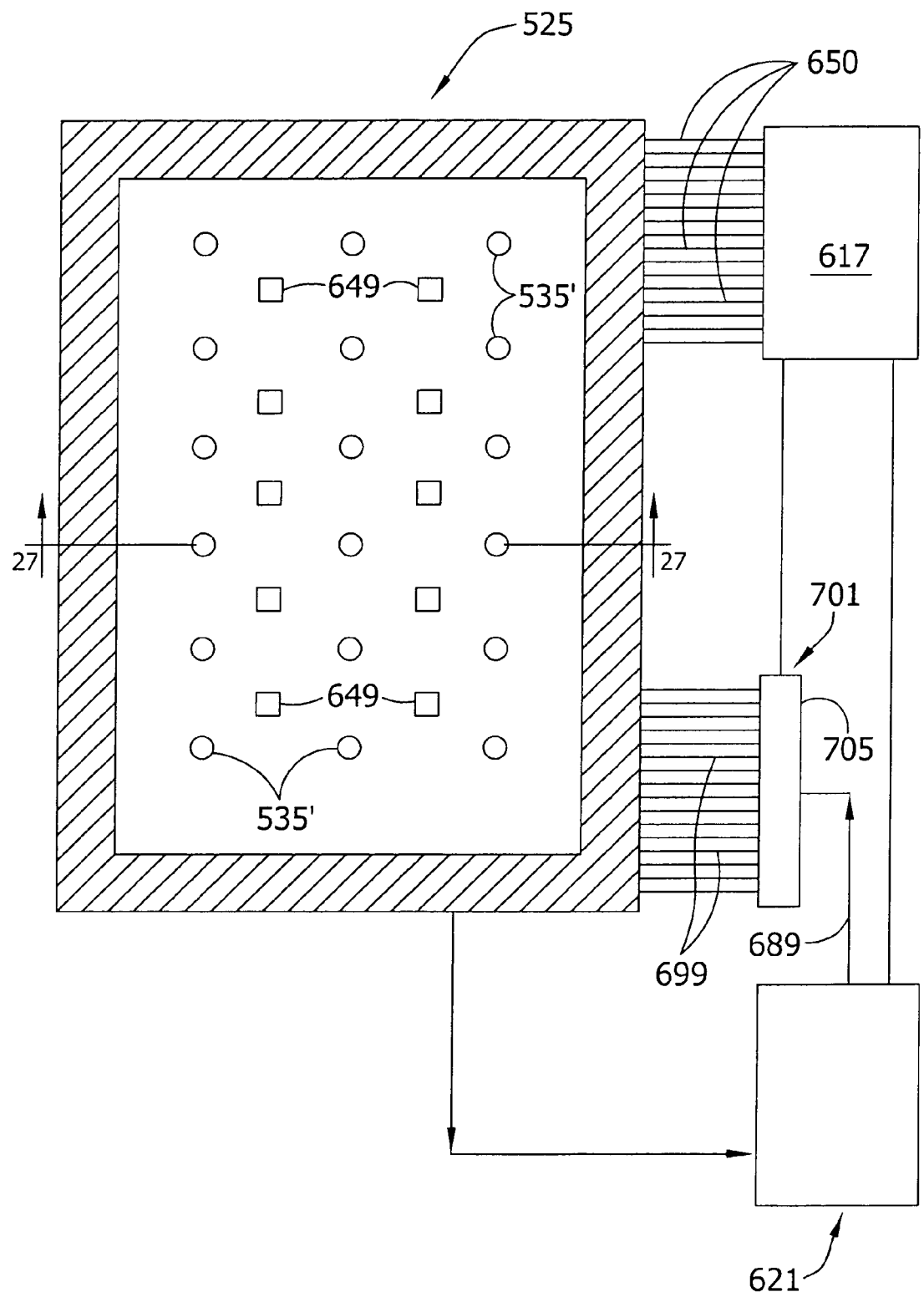
FIG. 26 is a schematic of another control unit integrated with a valve control system and sensors for distributing the heat transfer liquid within the enclosure.
Figure 27A:
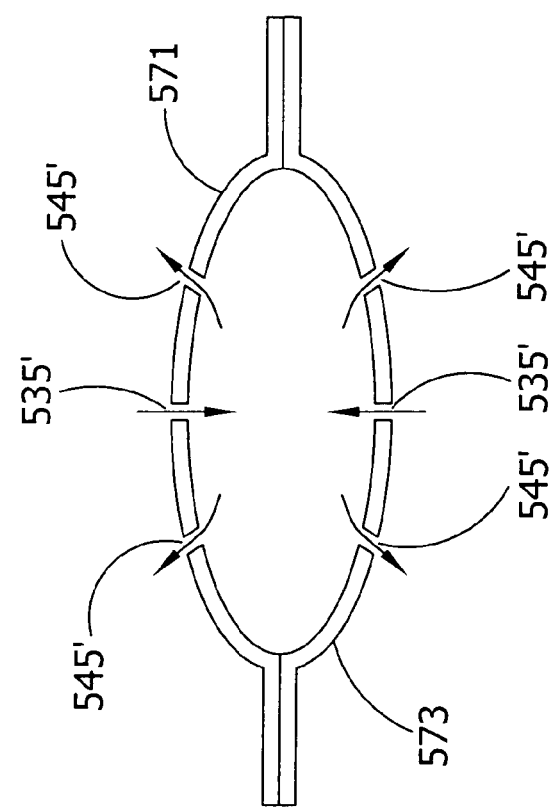
FIG. 27A is a section on line 27-27 of FIG. 26 showing heat transfer liquid entering the enclosure via inlets positioned on a single enclosure portion and discharging from the enclosure via outlets positioned on another enclosure portion.
Figure 27B:
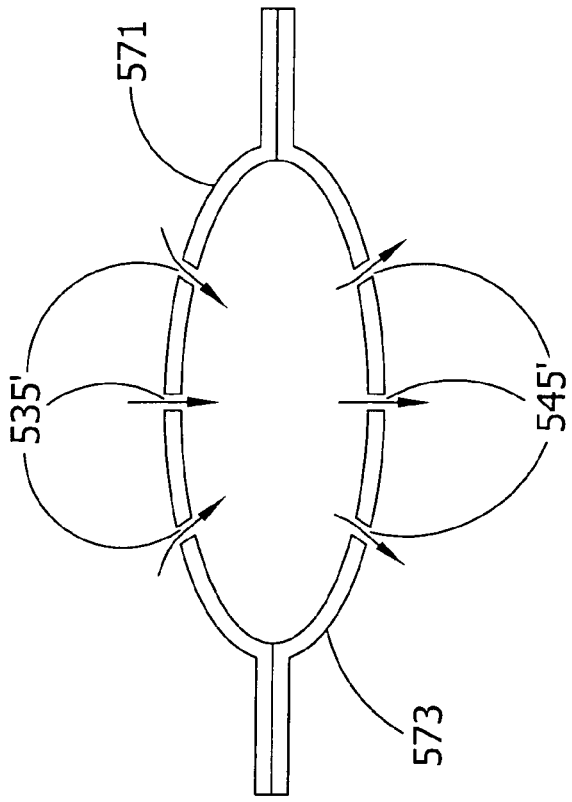
FIG. 27B is the section of FIG. 27A, but showing heat transfer liquid entering the enclosure via inlets positioned in a center of the enclosure portions and discharging from the enclosure via outlets spaced from the center.

As illustrated in FIGS. 25 and 26, the inlet 535 and outlet 545 may comprise multiple sub-inlets 535' and sub-outlets 545' spaced throughout the first and/or second portions of the enclosure 525. Because of their distribution, the sub-inlets 535' and sub-outlets 545' facilitate the flow of heat transfer liquid 539 over a larger area of the enclosed portion 531 of the patient's body, thereby promoting increased contact between the liquid and the portion 531 of the patient's body. As illustrated in FIG. 27A, the first and second portions 571, 573 may contain only sub-inlets 535' or sub-outlets 545' or, alternatively, as shown in FIG. 27B, the first and second portions may contain both sub-inlets 535' and sub-outlets 545'. In one embodiment, inlets 535 are positioned on both the first and second portions 571, 573 at locations generally corresponding to the portion of the patient's body received in the enclosure 525, and more specifically at a position offset from the medial line (i.e., longitudinal centerline) of the patient's body portion 531. However, location of outlets 545 on the medial line does not depart from the scope of the invention. The outlets 545 are positioned in the enclosure 525 at locations spaced from the center of the patient's body received in the enclosure 525 remote from the portion 531 of the patient's body received in the enclosure such as along at least one outer edge 605 of the enclosure (FIG. 19). As a result, heat transfer liquid 539 entering the enclosure 525 is not blocked by the patient's body and is directed both upward and downward to flow over and across both the front side and back side of the patient.

Referring now to FIGS. 29A-30B, the apparatus further comprises a liquid delivery system 621 for directing the heat transfer liquid 539 to flow through the inlet 535 of the enclosure 525 into the interior space 527 to the outlet 545 of the enclosure. The liquid delivery system 621 comprises a pump, generally indicated at 625, a heat exchanger 629, a reservoir 667 and at least one liquid passage (e.g. a conduit 689). The liquid delivery system 621 is a generally closed, continuous flow system whereby liquid exhausted from the outlet 545 of the enclosure 525 is directed to flow back to the inlet 535 for flow into the interior space 527 of the enclosure.

Figure 29A:
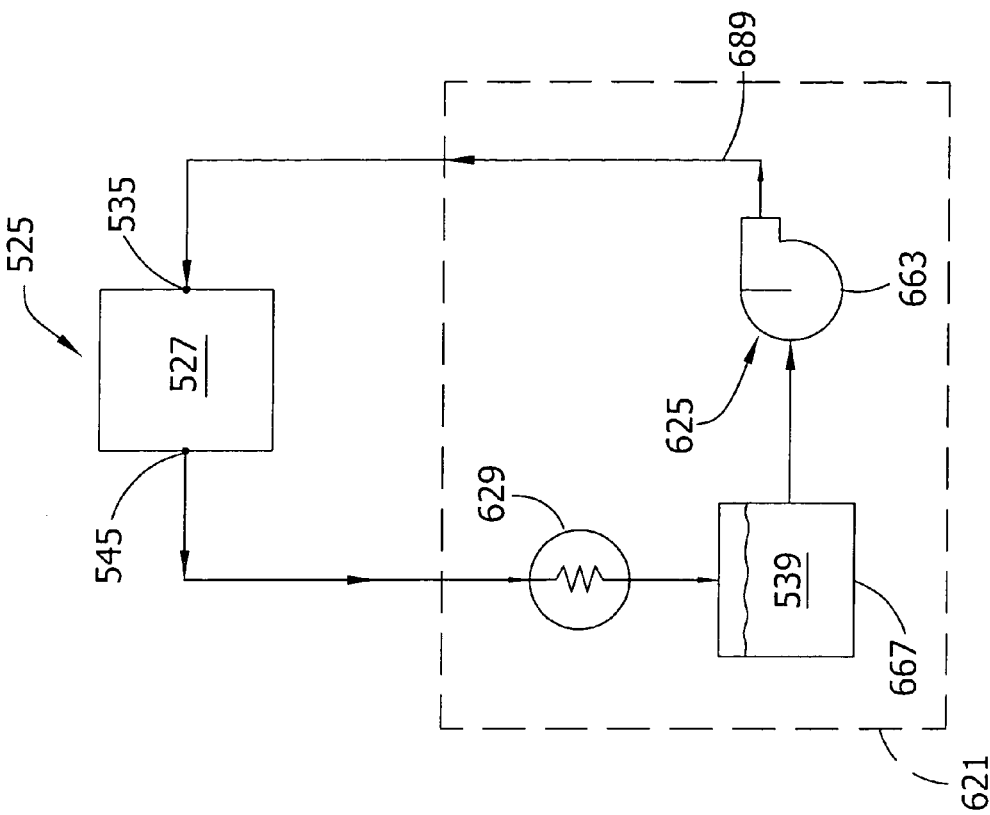
FIG. 29A is a schematic of apparatus of the present invention having an outlet pump.
Figure 29B:
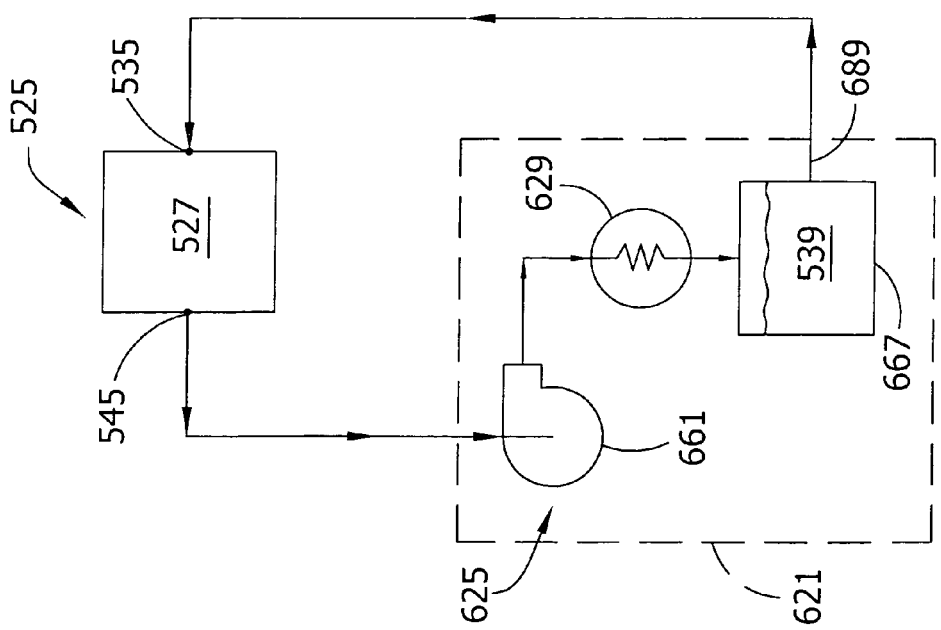
FIG. 29B is a schematic of apparatus of the present invention having an inlet pump.

Referring to FIG. 29A, the pump 625 comprises an outlet pump 661 in fluid communication with the outlet 545 for exhausting heat transfer liquid 539 from the enclosure 525 and in fluid communication with the inlet 535 for pumping heat transfer liquid 539 into the enclosure. For example, the outlet pump 661 may be a diaphragm pump having a pumping capacity of 10 liters per minute (2.75 gallons per minute) positioned adjacent the enclosure outlet 545. The pump draws heat transfer liquid 539 directly from the enclosure 525 and pumps it within the conduit 689 through the heat exchanger 629 and reservoir 667 before pushing it through the inlet 535 and into the interior space 527 of the enclosure. Alternatively, the pump 625 can comprise an inlet pump 663 arranged to discharge heat transfer liquid 539 from the reservoir 667 directly into the inlet 535 of the enclosure 525 and to pull heat transfer liquid 539 from the outlet 545 of the enclosure through the heat exchanger 629 and reservoir 667 (FIG. 29B). Alternatively, the heat transfer liquid 539 may drain from the enclosure 525 to the reservoir 667 by gravity. From the reservoir 667, the heat transfer liquid 539 may be pushed by the inlet pump 663 through the enclosure inlet 535 back into the enclosure. As discussed above, the use of both an inlet pump 663 and an outlet pump 661 is contemplated as being within the scope of this invention. Should higher flow rates or other parameters be required, other pumps, such as higher capacity gear, roller, or centrifugal pumps, may be used without departing from the scope of the present invention.

The heat exchanger 629 alters the temperature of the liquid from an outlet temperature measured after the liquid exits the outlet 545 of the enclosure 525 to an inlet temperature measured before the liquid enters the inlet 535 of the enclosure, so that liquid may be reintroduced into the enclosure after passing through the heat exchanger 629. Alternatively, the heat exchanger 629 may be positioned within the enclosure (not shown). In this embodiment, the pump 625 would be used to circulate the heat transfer liquid 539 over the portion of the patient's body within the enclosure. As previously mentioned, the heat exchanger 629 may be a Peltier device or a phase change material.

As mentioned, the liquid delivery system 621 comprises at least one liquid passageway 689 for allowing liquid to pass through the passageway to the inlets 535 and into the enclosure 525 (FIGS. 25 and 26). The passageway 689 is configured to distribute liquid over a large surface area of the patient's body. For example, the liquid passage 689 may comprise at least one main liquid conduit 697 (broadly, "passage") extending longitudinally of the enclosure 525, and at least two secondary liquid conduits 699 (broadly, "passages") extending laterally out from the main liquid passage 697 (FIG. 25). The main liquid passage 697 may branch into many secondary liquid passages 699 connected with the sub-inlets 535' to distribute liquid to the patient's body portion 531 within the enclosure 525. These conduits may be insulated to inhibit heat transfer from the heat transfer liquid 539 flowing within the passage and the surrounding materials or ambient air. Alternatively, the liquid passage 689 may enter a valve manifold 705 positioned outside the enclosure which directs the heat transfer liquid 539 into a plurality of secondary liquid passages 699 (FIG. 26). The secondary liquid passages 699 are in fluid communication with sub-inlets 535' to distribute liquid to the patient's body portion 531 within the enclosure 525. The paths of these conduits may vary without departing from the scope of the present invention.

Figure 30A:
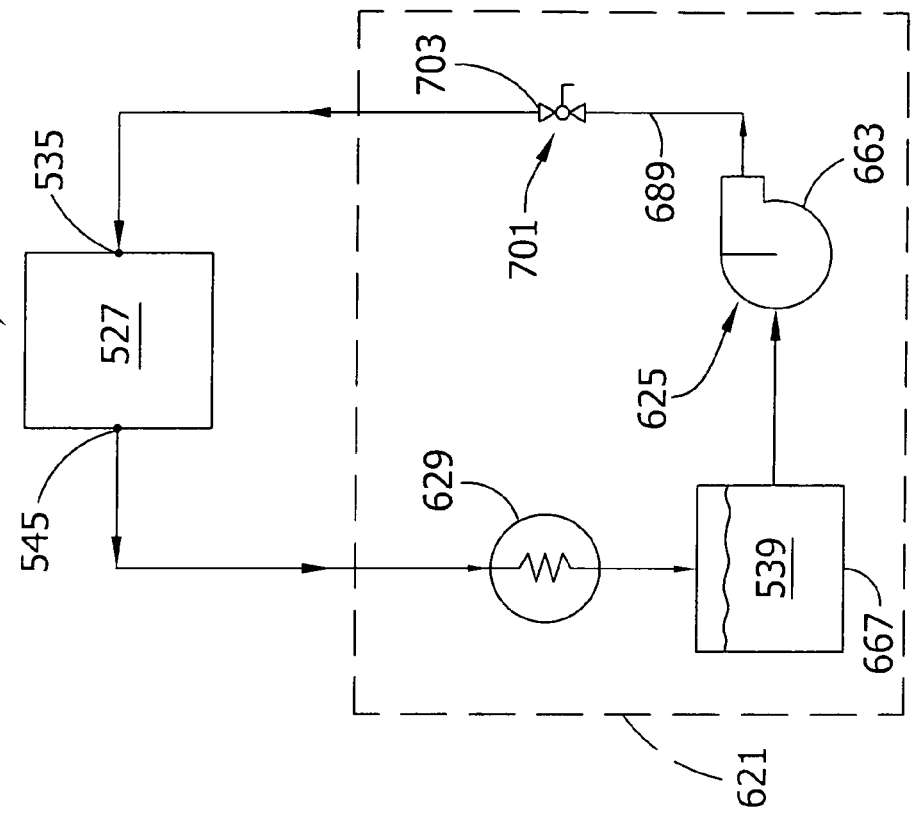
FIG. 30A is a schematic of apparatus of the present invention having an outlet pump and a flow regulating device; and, FIG. 30B is a schematic of apparatus of the present invention having an inlet pump and the flow regulating device.
Figure 30B:
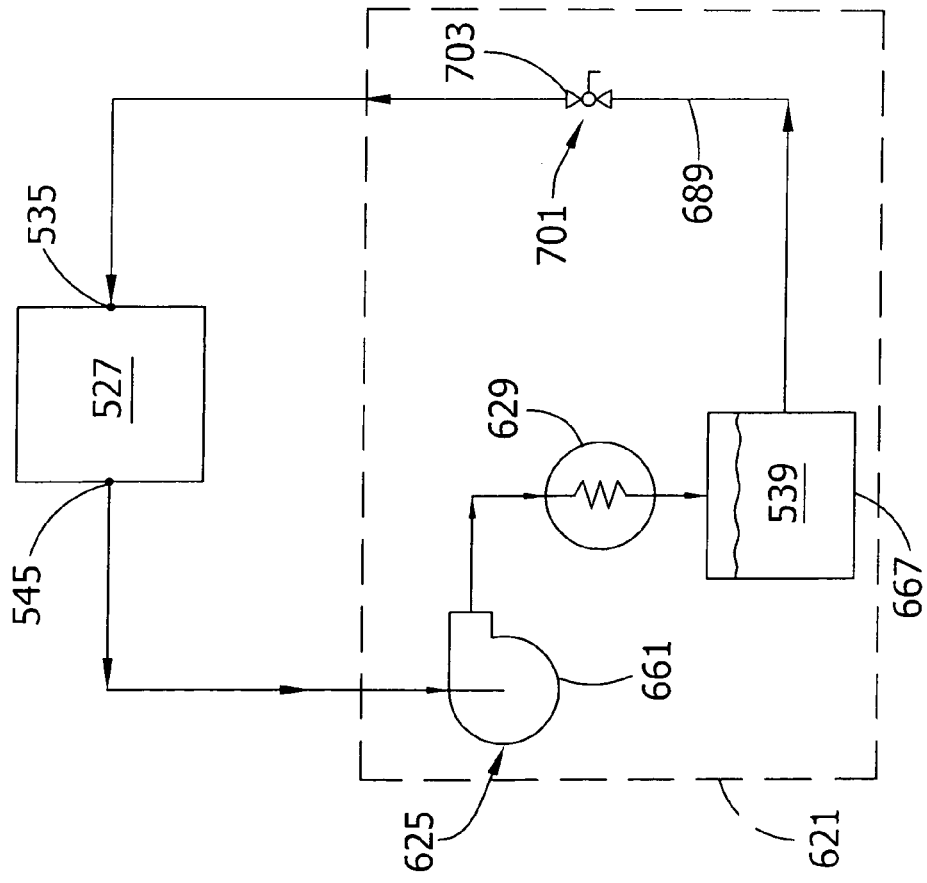

Referring to FIGS. 30A and 30B, the apparatus further comprises a valve system, generally indicated at 701, for controlling the flow of the heat transfer liquid 539 through the passageway 689. The valve system 701 comprises at least one adjustable valve 703 operable to control the flow of the heat transfer liquid 539 within the liquid delivery system 621. The valve 703 is movable from a closed position in which the heat transfer liquid 539 is inhibited from flowing, to an open position where the heat transfer liquid 539 is uninhibited to flow. In one embodiment, a valve 703 is associated with each sub-inlet 535' and sub-outlet 545', thereby maximizing the potential flow patterns within the enclosure 525 (FIG. 25). Alternatively, the valve system 701 may be positioned remote from the sub-inlets 535' and sub-outlets 545', as shown in FIG. 26, which illustrates the valve manifold 705 positioned outside the enclosure 525.

Figure 28:
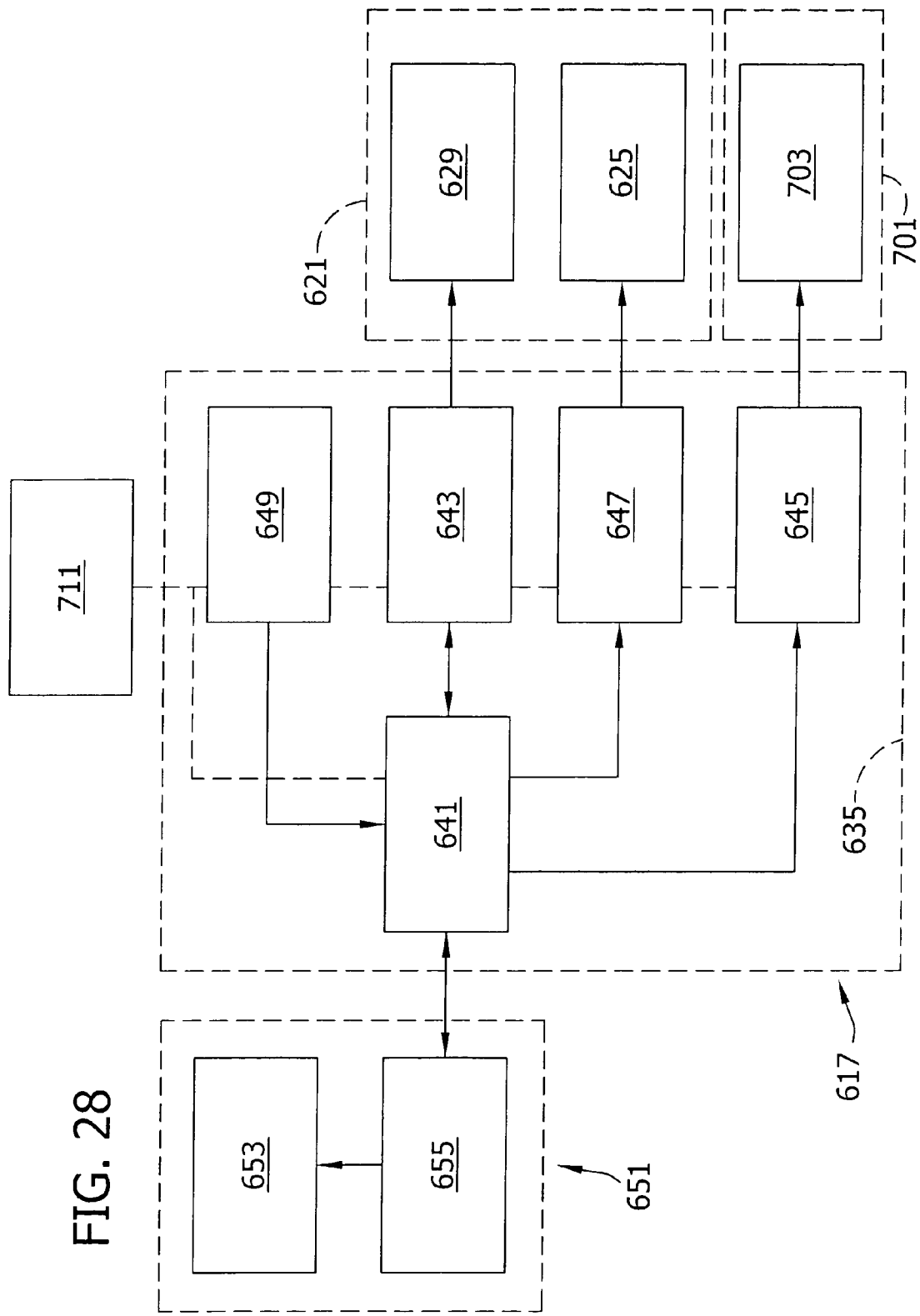
FIG. 28 is a schematic of a modified portable control unit of the apparatus of the present invention.

A fluid control system 635 communicates with the liquid delivery system 621 and valve system 701 to control the flow of liquid through the enclosure (FIG. 28). The control system 635 comprises a control unit, generally indicated at 617, having a programmable controller 641, an H-bridge drive circuit 643, a voltage limiter 645, at least one pump driver 647 and at least one sensor 649. The sensor 649 (e.g., which may measure temperature, flow rate or pressure) is positioned in the enclosure 525 for measuring a property of the heat transfer liquid 539 within the enclosure (FIG. 26). The control unit 617, which is integrated with the sensors 649 via control wires 650, process the property of the heat transfer liquid 539 measured by the sensor and correspondingly actuates the fluid liquid delivery system 621 and valve system 701 to distribute the heat transfer liquid 539 within the enclosure 525 in response to the property of the heat transfer liquid 539. The control system 635 is operable to alter the temperature of the heat transfer liquid 539 via the heat exchanger 629, drive the pump 625 and control the valve system 701. The apparatus further includes a user interface 651 for communicating the status of the system to the user, a display 653 for visually indicating particular parameters of the system and controls 655 that allow the user of the system to selectively control particular system functions. For example, such controls 655 may allow the user to input a set-point, or target, body temperature for the patient. The display 653, for example, could display this set-point temperature along with the actual body temperature of the patient, the liquid temperature and the liquid flow rate, among other things. As mentioned previously, the temperature sensor 131 is adapted for sending a body temperature reading of the patient to the control unit 617.

In operation, the fluid control unit 617 controls the liquid delivery system 621 and the valve system 701. Flow rate of the heat transfer liquid can be regulated by fluid control unit 617 by adjusting either the pumping rate or by adjusting the valve 703. The heat transfer liquid 539 may be maintained at a flow rate between about 0.25 liters per minute (0.06 gallons per minute) and about 10 liters per minute (2.75 gallons per minute), such as between 0.5 liters per minute (0.13 gallons per minute), such as about 5 liters per minute (0.53 gallons per minute). In one embodiment, the heat transfer liquid 539 is controlled by the fluid control system 635 at a flow rate of about 1.5 liters per minute (0.40 gallons per minute).

In addition, the fluid control unit 617 can control the pressure within the interior space 527 of the enclosure 525 by controlling the movement of liquid through the enclosure. A pressure differential can be created using the valve 703 as a resistance element and positioning it between the pump 625 and the enclosure 525 (FIGS. 30A and 30B). For example, when valve 703 creates sufficient resistance to flow entering the enclosure 525 via enclosure inlet 535, pump 625 must exert a negative pressure to pull fluid out of the enclosure 525 via enclosure outlet 545. The result is a negative gage pressure, or vacuum, within the interior space 527 of the enclosure 525. This can be accomplished by positioning the resistance element 703 (i.e. valve) between the outlet pump 661 and the enclosure inlet 535. A negative pressure within the enclosure 525 creates a gage pressure within the interior space 527 of between about 0 kiloPascal (0 pounds per square inch) and about −14 kiloPascals (−2.0 pounds per square inch). Alternately; positive gage pressure may be maintained within the enclosure 525. A positive gage pressure can be created by positioning the resistance element 703 between the enclosure outlet 545 and the inlet pump 663. The resistance element 703 is adjustable to thereby regulate the pressure within the enclosure 525.

The apparatus of the present invention, when equipped with a battery power supply 711, is portable thereby facilitating the cooling or warming of the patient in a remote environment without electricity or while the patient is in transport (FIG. 19).

In one embodiment of a method of the present invention is the administering a temperature responsive pharmaceutical to the body of a patient with a fluid as a carrying agent comprising enclosing at least a portion 531 of the patient's body within an enclosure 525 defining an interior space 527 for receiving the portion 531 of a patient's body therein. The enclosure 525 includes an inlet 535 in fluid communication with the interior space 527 of the enclosure for receiving the fluid into the interior space 527, and an outlet 545 in fluid communication with the interior space 527 of the enclosure for exhausting the fluid from the enclosure. The method further comprises delivering the temperature responsive pharmaceutical into the interior space 527 of the enclosure 525 for direct liquid contact with the portion 531 of the patient's body and controlling the temperature of the fluid within a responsive range of the pharmaceutical wherein the fluid is maintained at a temperature within the responsive range. The liquid temperature may be controlled to be in a selected range between about 0° C. (32° F.) to about 45° C. (113° F.). Generally, the selected temperature responsive pharmaceutical is either a temperature sensitive pharmaceutical or a temperature activated pharmaceutical. More specifically, the temperature responsive pharmaceutical is selected from a group including anti-coagulants, coagulants, antibiotics, antiviral agents, antitoxins, chemotherapy agents, anesthetic agents, anti-inflammatory agents, and analgesics.

In another embodiment, a method for adjusting the body temperature of a patient comprises substantially enclosing at least a portion 531 of a patient's body within an interior space 527 of an enclosure 525. The enclosure includes an inlet 535 for receiving heat transfer liquid 539 into the interior space 527 for flow over the patient's body in direct liquid contact therewith to promote heat transfer between the patient's body and the heat transfer liquid 539, and an outlet 545 in fluid communication with the interior space 527 of the enclosure for exhausting the heat transfer liquid 539 from the enclosure. The method further comprises directing the heat transfer liquid 539 through the inlet 535 of the enclosure 525 into the interior space 527 to the outlet 545 of the enclosure and controlling the heat transfer liquid 539 at a flow rate between about 0.25 liters per minute (0.06 gallons per minute) and about 10.0 liters per minute (2.75 gallons per minute), such as at a flow rate between about 0.5 liters per minute (0.13 gallons per minute) and about 5 liters per minute (0.53 gallons per minute), such as at a flow rate of about 1.5 liters per minute (0.40 gallons per minute). The flow rate of the heat transfer liquid 539 is controlled by the control unit 617 and user interface 651 by adjusting the valve 705.

The pump 625 may be a gear pump, such as the UGP-2000 series manufactured by B&D Pumps, Inc. of Huntley, Ill., USA, or a roller-type pumphead with a motor drive, such as the 500 series process pump manufactured by Watson-Marlow OEM of Paramus, N.J., USA. Other types of pumps could be used without departing from the scope of this invention. Moreover, the pumphead 664 of the pump 625 may be detachable and disposable to minimize the likelihood of cross-contamination to subsequent patients (FIG. 19). In one configuration, the pump 625 comprises a relatively inexpensive pumphead 664 easily removalable from the pump. For example, the pumphead 664 made be from a plastic material and attached to the pump 625 using bolts. After the pumphead 664 has been used, it can be removed from the pump, discarded properly, and a new pumphead installed on the pump for use with another patient.

In yet another embodiment, a method for adjusting the body temperature of a patient comprises substantially enclosing at least a portion of a patient's body within an interior space 527 of an enclosure 525. The enclosure 525 has an inlet 535 for receiving heat transfer liquid 539 into the interior space for flow over the patient's body in direct liquid contact to promote heat transfer between the patient's body and the heat transfer liquid. An outlet 545 is in fluid communication with the interior space 527 of the enclosure 525 for exhausting the heat transfer liquid 539 from the enclosure. Heat transfer liquid 539 is directed through the inlet 535 of the enclosure into the interior space 529 to the outlet 545 of the enclosure 525. In addition, the patient also receives at least one therapy selected from a group of therapies including iced saline infusion, cardiopulmonary bypass, veno-veno bypass, intravascular cooling catheters, temperature-controlled ventilation, intravascular infusion of a slurry of ice and saline, and intrapulmonary infusion of a slurry of ice and saline.

A method for performing cardiopulmonary resuscitation (CPR) on a patient comprises increasing the coronary perfusion pressure in the patient, supplying oxygen to the lungs of the patient, and compressing the thoracic region of the patient. The coronary perfusion pressure in the patient can be increased by enclosing at least a portion of a patient's body within an interior space 527 of an enclosure 525 and directing heat transfer liquid 539 over at least a portion 531 of the patient's body in direct liquid contact therewith to cool the patient's body. The enclosure 525 has an inlet 575 for receiving heat transfer liquid 539 into the interior space 527 and an outlet 545 for exhausting the heat transfer liquid from the enclosure. One of the effects of cooling the skin of the patient is it causes the release of catacholamines, which in turn, results in vasoconstriction in the patient. Vasoconstriction causes the coronary perfusion pressure to increase. It is well known that increased coronary perfusion pressure in the patient increases the chances of resuscitation. It is also known that the coronary perfusion pressure in the patient can be increased using drugs, such as epinephrine and vasopressin. The step of supplying oxygen to the lungs of the patient can be done manually (e.g., mouth-to-mouth) or mechanically using a mask. Likewise, the step of compressing the thoracic region of the patient can be performed manually or mechanically by applying sufficient force to the patient's thoracic region to cause compressions.

To examine the process of induced hypothermia in a quantifiable manner, a series of preliminary experiments were conducted using an acute animal preparation. A description of such experiments follows.

EXAMPLE 1

Swine Packed in Ice

The first example studied the effect of total encasement of an animal, here a swine, in ice. This study was conducted in view of recent clinical reports suggesting that cooling gel packs work reasonably well. The study was done by placement of approximately 45 kg (100 pounds) of ice in 2.3 kg (5 pound) plastic bags both under and around the swine. Swine body temperatures and vital signs were then monitored over time, and the ice was removed when the observed core body temperature had dropped from about 34.5° C. (94.1° F.) to about 28.8° C. (83.8° F.).

More specifically, a first swine having a mass of 36 kg (79 pounds) was anaesthetized with Telazol®, a federally registered mark of A. H. Robins Co. of Richmond, Va., U.S.A., and xylazine. The hair of the swine was also clipped. The swine was then instrumented with an electrocardiogram (ECG) via conventional pads for electrically monitoring its heart rhythm during the experiment and a respirator for maintaining proper ventilation. A pulmonary artery catheter was placed via the jugular vein for monitoring the pulmonary artery pressure and blood temperature within the artery. Catheter placement was confirmed by visualizing right ventricular and subsequently pulmonary artery pressure while advancing the catheter. A thermistor sensor of the catheter was connected to a temperature monitor and calibrated in advance, which was then used to calibrate two other type T thermocouples. The first type T thermocouple was connected to the swine's skin under the right front leg with adhesive tape. The second thermocouple was placed deep within the uppermost ear of the swine and then sealed with foam insulation. All sensors were connected to a DATAQ A/D converter system (available from DATAQ Instruments, Inc. of Akron, Ohio, USA) and digitized during the experiments at a rate of 120 Hertz. Once anaesthetized and lying on its side, the exposed exterior of the swine was packed with conventional 2.3 kilogram (5 pound) bags of ice. Approximately 20 bags were used in the experiment, such that a bag of ice was contacting the majority of the skin of the swine.

Figure 17:
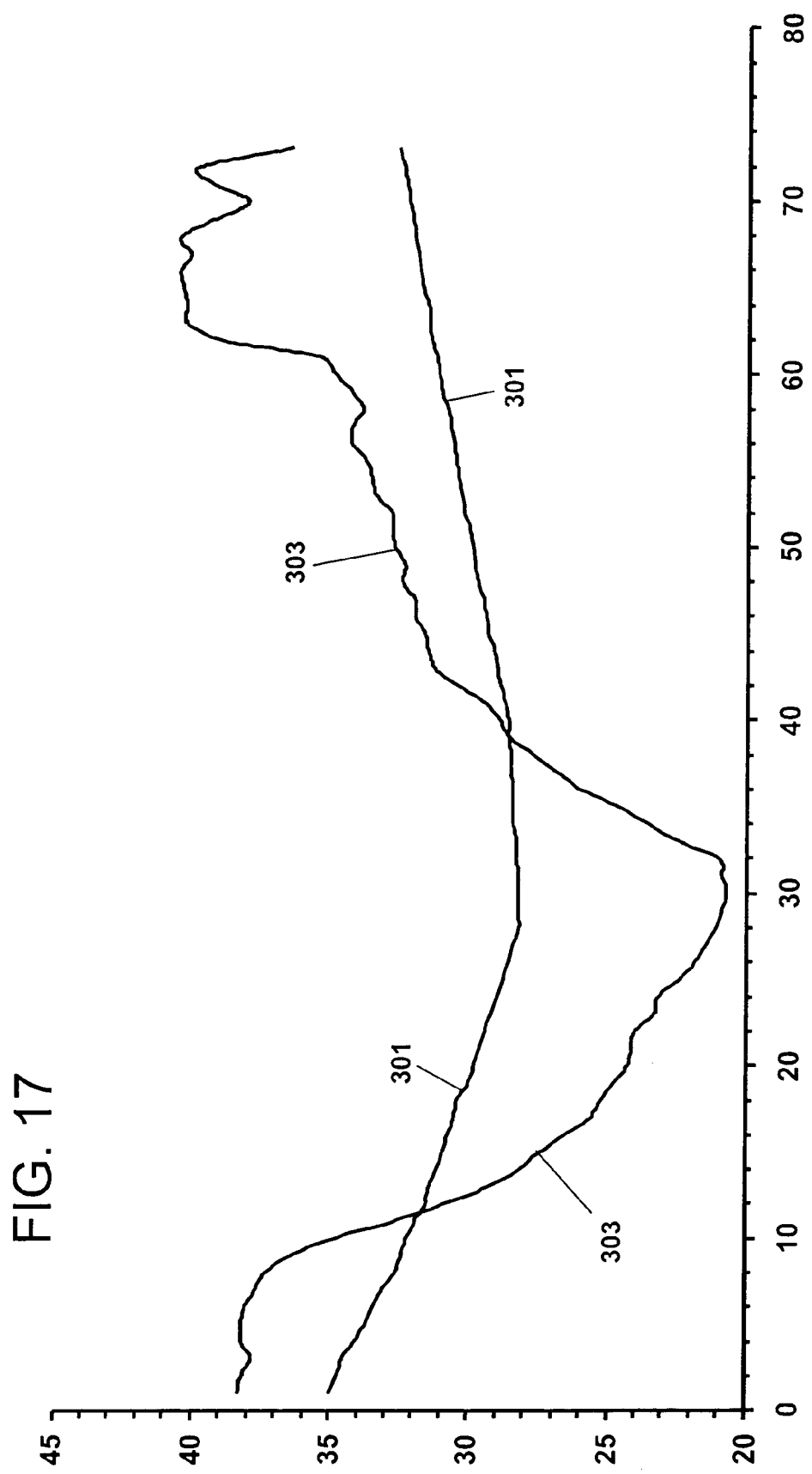
FIG. 17 is a graph depicting the skin temperature and internal body temperature of a swine undergoing the method of the present invention.

The skin temperature and pulmonary artery blood temperature were then recorded over time to determine the cooling rate of the swine due to being packed in ice. The temperature results of this example are depicted in FIG. 17 as curves 301 and 303. For FIGS. 17 and 18, the vertical axis of the chart indicates temperature in Celsius, while the horizontal axis indicates time in minutes. The maximum and minimum values shown on the temperature scales vary between figures. Curve 301 indicates the pulmonary artery temperature of the swine and curve 303 represents the skin temperature. As would be expected, the skin temperature of the swine leads the pulmonary artery temperature, as the skin is providing the cooling for the entire body. Curve 301 demonstrates that eight minutes into the cooling process, the core body temperature of the swine dropped by 1° C. (1.8° F.). After eleven, seventeen and twenty-five minutes, the core temperature had dropped by a total of 2° C. (3.6° F.), 3° C. (5.4° F.) and 4° C. (7.2° F.), respectively.

EXAMPLE 2

Swine in Enclosure with Liquid Flow

In the second example, a second swine was enclosed in a prototype enclosure of apparatus of the present invention, generally as described above. The apparatus was used to cool and re-warm the animal several times over a period of several hours. The enclosure was operated in one of two ways, with water, as the heat transfer liquid, flowing from the top to the bottom of the enclosure or with water flowing oppositely, bottom to top. Pumping water into the interior space at the top of the enclosure and then out of the interior space at the bottom generated a positive gage pressure within the interior space of the enclosure. Pumping water into the interior space at the bottom of the enclosure and then out of the interior space at the top of the enclosure generated a sub-atmospheric pressure, or partial negative pressure, within the interior space of the enclosure. In this mode, the enclosure becomes more conformal to the body and allows for a smaller amount of circulating water as described above.

In this example, a second swine having a mass of 36 kg (79 pounds) was anaesthetized, hairs clipped, instrumented and laid on its side similar to the first swine described above. The swine was then placed within an enclosure sized and shaped for a swine, but substantially as described above. The enclosure was designed to achieve direct liquid contact with the swine's skin. The enclosure included a lower member placed beneath the swine and an upper member placed over the swine only the snout of the swine extended out through an opening in the enclosure, allowing the swine to breathe. The lower member and upper member were joined about first and second sealing portions located generally at the edge margin of each member, generally as described above. The enclosure was sealed around the snout of the swine so that a negative gage pressure could be generated within the interior space of the enclosure. The upper and lower members each additionally included five sub-inlets and five sub-outlets, respectively, for circulating water throughout the interior space of the enclosure. The enclosure was fabricated from layers of neoprene, aluminized polyester, polyester batting and nylon mesh, generally as set forth above.

Cooling or warming water was then pumped by computer-controlled gear pumps from reservoirs located near the swine into the enclosure. The pumps used were capable of moving 1.7 liters (0.45 gallon) per minute. As described above, the enclosure dispersed the liquid within the interior space around, over and under the animal in direct contact therewith. The heat exchange system of this example utilized an ice bath reservoir pumped through the enclosure for cooling. The ice bath kept the inlet temperature of the water at about 1 to 2° C. (34 to 36° F.). For the re-warming portion of the experiment, hot water was applied to the swine at an inlet temperature of 45° C. (113° F.).

Figure 18:
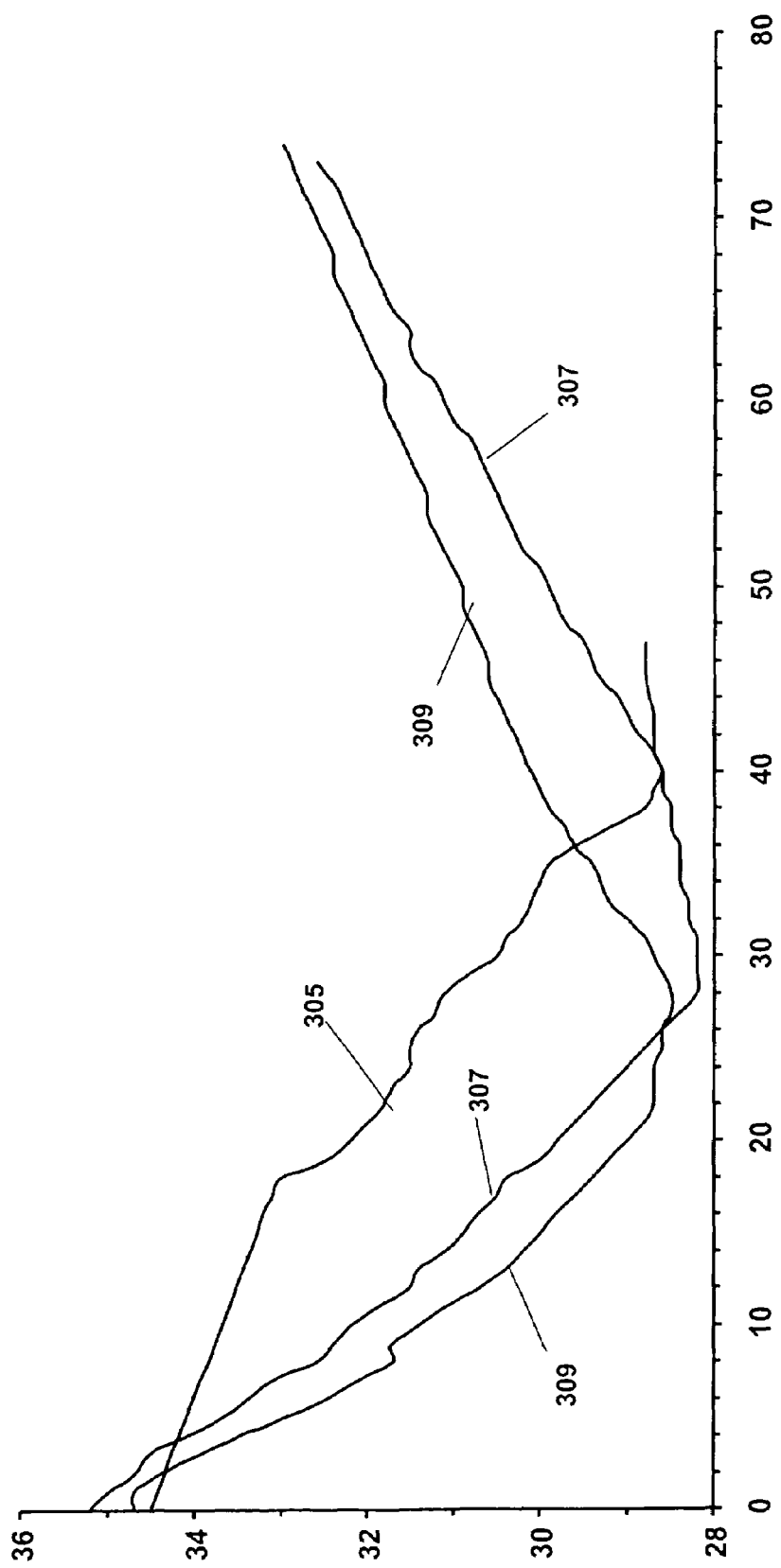
FIG. 18 is a graph of the internal body temperature of a swine subjected to different methods of cooling.

The skin temperature and pulmonary artery blood temperature were then both recorded over time to determine the cooling rate of the swine. The temperature results of this experiment are depicted in FIG. 18 as curves 305, 307 and 309. Curve 305 indicates the pulmonary artery temperature of the swine packed in ice from example 1, curve 307 indicates the pulmonary artery temperature of the swine in the enclosure with water moving from bottom to top and curve 309 indicates the pulmonary artery temperature of the swine in the enclosure with water moving from top to bottom.

Reviewing curve 307, which pertains to bottom to top water flow, the core body temperature of the swine as measured by the pulmonary artery catheter dropped by 1° C. (1.8° F.) in the first four minutes of the cooling process. Such cooling is twice as fast as the swine packed in ice. Moreover, after seven, ten and fourteen minutes, the swine's core temperature had fallen by a total of 2° C. (3.6° F.), 3° C. (5.4° F.) and 4° C. (7.2° F.), respectively. This method cooled the swine by 4° C. (7.2° F.) in fourteen minutes, which is 79% faster than the swine packed in ice. Similarly, the enclosure employing top to bottom flow, curve 309, cooled the swine more quickly than example 1. At three, six, eight and twelve minutes after beginning the test, for example, the swine's core temperature had fallen by a total of 1° C. (1.8° F.), 2° C. (3.6° F.), 3° C. (5.4° F.) and 4° C. (7.2° F.), respectively. The top to bottom flow cooled the swine by 4° C. (7.2° F.) in twelve minutes, which is 108% faster than the swine packed in ice.

Comparing this rate to published cooling rates from experiments using cooled air, the cooling rates of the present example are much better. Comparing with the hypothermia research noted above (Sterz F. et al., *Mild Therapeutic Hypothermia to Improve the Neurologic Outcome after Cardiac Arrest*, 346 NEW ENG. J. MED. 549-556 (2002)), where cooled air was the medium selected for cooling body temperature, Sterz notes a 1° C. (1.8° F.), 2° C. (3.6° F.) and 3° C. (5.4° F.) core temperature drop in 4 hours, 6 hours and 10 hours, respectively, on human subjects. Obtaining such cooling rates in a swine in a matter of minutes, indicates much more rapid cooling, even recognizing body mass differences between swines and humans.

The results of these examples are summarized in the following table:

| Cooling Method | Packed Ice [*] | Enclosure, Bottom to Top Cooling [*] | Enclosure, Top to Bottom Cooling [*] | Cooled Air (Sterz) [**] |
|---|---|---|---|---|
| 1 C. ° (1.8 F. °) drop in temperature | 8 minutes | 4 minutes | 3 minutes | 4 hours |
| 2 C. ° (3.6 F. °) drop in temperature | 11 minutes | 7 minutes | 6 minutes | 6 hours |
| 3 C. ° (5.4 F. °) drop in temperature | 17 minutes | 10 minutes | 8 minutes | 10 hours |
| 4 C. ° (7.2 F. °) drop in temperature | 25 minutes | 14 minutes | 12 minutes | — |

[*] 36 Kg Swine
[**] Clinical subjects

To summarize, a 4° C. (7.2° F.) temperature drop can be achieved in a 36 kg (79 pounds) animal with normal circulation in 12 minutes. This is a significantly faster core temperature drop than that achieved by packing the same size animal in ice or in clinical studies with human subjects utilizing cooled air. While the animals of the examples had relatively normal circulation, and were under anesthetic agents, the cooling rates achieved are significant. Such therapeutic cooling has the potential to significantly increase the chances of neurologically intact survival following cardiac arrest. Such therapy may also be effective in the treatment of stroke.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. Apparatus for adjusting the body temperature of a patient, said apparatus comprising:
    an enclosure defining an interior space for receiving a portion of a patient's body, the enclosure being constructed for receiving heat transfer liquid into the interior space for direct liquid contact with the portion of the patient's body to promote heat transfer between the patient and said heat transfer liquid;
    at least a portion of said enclosure including an outer layer and a porous inner fluid transfer layer engageable with the portion of the patient's body for carrying said heat transfer liquid, said transfer layer being formed from a substantially hydrophobic material, wherein the fluid transfer layer comprises a matrix of fibers.

2. Apparatus as set forth in claim 1 wherein the enclosure has an inlet and an outlet, and the fluid transfer layer is arranged for transporting heat transfer liquid from the inlet to the outlet.

3. Apparatus as set forth in claim 1 further comprising a liquid delivery system for driving heat transfer liquid into the enclosure through the inlet, through the fluid transfer layer, and out of the outlet.

4. Apparatus as set forth in claim 1 wherein said fluid transfer layer comprises a layer of batting.

5. Apparatus as set forth in claim 1 wherein at least a portion of the enclosure is transparent for viewing at least a part of the portion of the patient's body received in the interior space.

6. Apparatus as set forth in claim 1 for adjusting the body temperature of a patient, said apparatus comprising:
    an enclosure defining an interior space for receiving a portion of a patient's body, the enclosure being constructed for receiving heat transfer liquid into the interior space for direct liquid contact with the portion of the patient's body to promote heat transfer between the patient and said heat transfer liquid, wherein said enclosure has an opening for accessing the interior space;
    at least a portion of said enclosure including an outer layer and a porous inner fluid transfer layer engageable with the portion of the patient's body for carrying said heat transfer liquid, said transfer layer being formed from a substantially hydrophobic material.

7. Apparatus as set forth in claim 6 wherein the enclosure has an inlet and an outlet, and the fluid transfer layer is arranged for transporting heat transfer liquid from the inlet to the outlet.

8. Apparatus as set forth in claim 6 further comprising a liquid delivery system for driving heat transfer liquid into the enclosure through the inlet, through the fluid transfer layer, and out of the outlet.

9. Apparatus as set forth in claim 6 wherein said fluid transfer layer comprises a layer of batting.

10. Apparatus as set forth in claim 6 wherein at least a portion of the enclosure is transparent for viewing at least a part of the portion of the patient's body received in the interior space.

11. Apparatus as set forth in claim 6 wherein said opening is sealable for enclosing said portion of the patient's body.

12. Apparatus as set forth in claim 11 wherein said opening is sealable using a slide fastener.

13. Apparatus as set forth in claim 1 wherein said outer layer comprises a sheet-like body-facing component and a sheet-like outer component, said sheet-like body-facing component and sheet-like outer component being in face-to-face relationship with one another, said components further being joined to one another along their facing sides to form at least one liquid passage between the components, said liquid passage being in fluid communication with the interior space of the enclosure for allowing liquid to pass from the liquid passage to the interior space.

14. Apparatus as set forth in claim 13 further comprising an inlet in the body-facing component in fluid communication with the liquid passage and the interior space of the enclosure for directing heat transfer liquid into said interior space.

15. Apparatus as set forth in claim 14 wherein said inlet comprises a plurality of inlets for directing the flow of heat transfer fluid over a larger area of the enclosed portion of the patient's body.

16. Apparatus as set forth in claim 1 further comprising an outlet in fluid communication with the interior space of the enclosure for exhausting the heat transfer liquid from the interior space.

17. Apparatus as set forth in claim 1 wherein said outer layer is formed from a flexible material.

18. Apparatus as set forth in claim 17 wherein said outer layer is formed from a flexible material selected from a group of materials including polyvinyl chloride, polyethylene, and polyurethane.

19. Apparatus as set forth in claim 1 wherein said heat transfer liquid has a volume between about 4 liters and about 30 liters.

20. Apparatus for adjusting the body temperature of a patient, said apparatus comprising:
    an enclosure defining an interior space for receiving a portion of a patient's body, the enclosure being constructed for receiving heat transfer liquid into the interior space for direct liquid contact with the portion of the patient's body to promote heat transfer between the patient and said heat transfer liquid, wherein said enclosure is constructed to receive a portion of the patient from the neck downward;
    at least a portion of said enclosure including an outer layer and a porous inner fluid transfer layer engageable with the portion of the patient's body for carrying said heat transfer liquid, said transfer layer being formed from a substantially hydrophobic material; wherein the fluid transfer layer comprises a matrix of fibers.

21. Apparatus for adjusting the body temperature of a patient, said apparatus comprising:
an enclosure defining an interior space for receiving a portion of a patient's body, the enclosure being constructed for receiving heat transfer liquid into the interior space for direct liquid contact with the portion of the patient's body to promote heat transfer between the patient and said heat transfer liquid, wherein said heat transfer liquid has a temperature between about 0° C. and about 5° C.;
at least a portion of said enclosure including an outer layer and a porous inner fluid transfer layer engageable with the portion of the patient's body for carrying said heat transfer liquid, said transfer layer being formed from a substantially hydrophobic material.

22. Apparatus for adjusting the body temperature of a patient, said apparatus comprising:
an enclosure defining an interior space for receiving a portion of a patient's body, said enclosure being constructed for receiving heat transfer liquid into said interior space for direct liquid contact with the portion of the patient's body to promote heat transfer between the patient's body and the heat transfer liquid;
at least a portion of the enclosure including a sheet-like body-facing component and a sheet-like outer component, said sheet-like body-facing component and sheet-like outer component being in face-to-face relationship with one another, said components further being joined to one another along their facing sides to form at least one liquid passage between the components, said liquid passage being in fluid communication with the interior space of the enclosure, the body-facing component having at least one inlet therein corresponding to the liquid passage for allowing liquid to pass from the liquid passage to between the body-facing component and the portion of the patient's body, wherein said inlet comprises a plurality of inlets for directing the flow of heat transfer fluid over a larger area of the enclosed portion of the patient's body; and
a liquid delivery system for driving said heat transfer liquid to flow through the liquid passage and inlet into the interior space.

23. Apparatus as set forth in claim 22 wherein said enclosure further comprises a porous layer capable of carrying said heat transfer liquid throughout the enclosure.

24. Apparatus as set forth in claim 23 wherein said porous layer of the upper member comprises a layer of batting.

25. Apparatus as set forth in claim 22 including a plurality of liquid passages.

26. Apparatus as set forth in claim 25 wherein each of said liquid passages are in fluid communication with at least one inlet.

27. Apparatus as set forth in claim 22 wherein the liquid delivery system comprises a fluid control system for controlling the liquid delivery system to deliver said heat transfer liquid at a flow rate between about 0.25 liters per minute (0.06 gallons per minute) and about 10.0 liters per minute (2.75 gallons per minute).

28. Apparatus as set forth in claim 27 wherein said fluid control system is configured for controlling the liquid delivery system to deliver said heat transfer liquid at a flow rate between about 0.5 liters per minute (0.13 gallons per minute) and about 5 liters per minute (0.53 gallons per minute).

29. Apparatus as set forth in claim 28 wherein said fluid control system is configured for controlling said heat transfer liquid at a flow rate of about 1.5 liters per minute (0.40 gallons per minute).

30. Apparatus as set forth in claim 22 wherein said sheet-like body-facing component and sheet-like outer component are joined to one another by a heat seal to form the liquid passage between the components.

31. Apparatus for adjusting the body temperature of a patient, said apparatus comprising:
an enclosure defining an interior space for receiving a portion of a patient's body, said enclosure being constructed for receiving heat transfer liquid into said interior space for direct liquid contact with the portion of the patient's body to promote heat transfer between the patient's body and the heat transfer liquid;
at least a portion of the enclosure including a sheet-like body-facing component and a sheet-like outer component, said sheet-like body-facing component and sheet-like outer component being in face-to-face relationship with one another, said components further being joined to one another along their facing sides to form at least one liquid passage between the components, said liquid passage being in fluid communication with the interior space of the enclosure, the body-facing component having at least one inlet therein corresponding to the liquid passage for allowing liquid to pass from the liquid passage to between the body-facing component and the portion of the patient's body; and
a liquid delivery system for driving said heat transfer liquid to flow through the liquid passage and inlet into the interior space, wherein the liquid delivery system is a generally closed, continuous flow system whereby liquid exhausted from the interior space of the enclosure is directed to flow back to said inlet for flow into the interior space of the enclosure.

32. Apparatus as set forth in claim 31 wherein said liquid delivery system further comprises at least one liquid conduit for allowing liquid exhausted from said enclosure to pass through the conduit to the liquid passage and into the enclosure.

33. Apparatus as set forth in claim 32 wherein at least a portion of said conduit is insulated.

34. Apparatus for adjusting the body temperature of a patient, said apparatus comprising:
an enclosure defining an interior space for receiving a portion of a patient's body, said enclosure being constructed for receiving heat transfer liquid into said interior space for direct liquid contact with the portion of the patient's body to promote heat transfer between the patient's body and the heat transfer liquid;
at least a portion of the enclosure including a sheet-like body-facing component and a sheet-like outer component, said sheet-like body-facing component and sheet-like outer component being in face-to-face relationship with one another, said components further being joined to one another along their facing sides to form at least one liquid passage between the components, said liquid passage being in fluid communication with the interior space of the enclosure, the body-facing component having at least one inlet therein corresponding to the liquid passage for allowing liquid to pass from the liquid passage to between the body-facing component and the portion of the patient's body;
a liquid delivery system for driving said heat transfer liquid to flow through the liquid passage and inlet into the interior space; and
a pump for transferring said heat transfer liquid.

35. Apparatus as set forth in claim 34 wherein the pump has a detachable pumphead.

36. Apparatus as set forth in claim 35 wherein the pumphead is disposable.

37. Apparatus as set forth in claim 34 wherein the pump is a gear pump.

38. Apparatus as set forth in claim 34 wherein the pump is a roller pump.

39. Apparatus as set forth in claim 34 further comprising a reservoir in fluid communication with the pump such that liquid exhausted from the interior space of the enclosure flows into the reservoir before entering into the liquid passage.

40. Apparatus as set forth in claim 39 wherein the reservoir is a disposable reservoir.

41. Apparatus as set forth in claim 39 wherein the reservoir comprises a first compartment for holding a phase change material and a second compartment for holding the heat transfer liquid, the compartments being arranged such that said phase change material alters the temperature of said heat transfer liquid.

42. Apparatus as set forth in claim 41 wherein said phase change material is ice.

43. Apparatus as set forth in claim 41 wherein at least a portion of one of the compartments of the reservoir is thermally conductive.

44. Apparatus for adjusting the body temperature of a patient, said apparatus comprising:
an enclosure defining an interior space for receiving a portion of a patient's body, said enclosure being constructed for receiving heat transfer liquid into said interior space for direct liquid contact with the portion of the patient's body to promote heat transfer between the patient's body and the heat transfer liquid, wherein said enclosure is configured to receive a portion of the patient from the neck downward;
at least a portion of the enclosure including a sheet-like body-facing component and a sheet-like outer component, said sheet-like body-facing component and sheet-like outer component being in face-to-face relationship with one another, said components further being joined to one another along their facing sides to form at least one liquid passage between the components, said liquid passage being in fluid communication with the interior space of the enclosure, the body-facing component having at least one inlet therein corresponding to the liquid passage for allowing liquid to pass from the liquid passage to between the body-facing component and the portion of the patient's body; and
a liquid delivery system for driving said heat transfer liquid to flow through the liquid passage and inlet into the interior space.

45. Apparatus as set forth in claim 44 wherein the liquid passage has a height of about 3 mm and a width of about 25 mm.

46. Apparatus for adjusting the body temperature of a patient, said apparatus comprising
an enclosure defining an interior space for receiving a portion of a patient's body, and
a liquid delivery system for driving heat transfer liquid into said interior space of the enclosure for direct liquid contact with the portion of the patient's body received therein to promote heat transfer between the patient's body and the heat transfer liquid, the liquid delivery system having a fluid reservoir, said reservoir having a first compartment for holding a phase change material and a second compartment for holding the heat transfer liquid, said compartments being arranged such that the phase change material alters the temperature of the heat transfer liquid.

47. Apparatus as set forth in claim 46 wherein the reservoir is a thermally conductive reservoir.

48. Apparatus as set forth in claim 47 wherein the reservoir is made of aluminum.

49. Apparatus as set forth in claim 48 wherein the reservoir is disposable.

50. Apparatus as set forth in claim 46 wherein said heat transfer liquid is water, and said phase change material is ice.

51. Apparatus as set forth in claim 46 wherein the first compartment overlies the second compartment.

52. Apparatus as set forth in claim 51 wherein the first and second compartments have conical cross-sections.

53. Apparatus as set forth in claim 46 wherein the first and second compartments further comprise Peltier devices for maintaining predetermined temperatures within the compartments.

54. Apparatus as set forth in claim 53 wherein the first compartment is maintained at a temperature different than the second compartment.

55. Apparatus as set forth in claim 54 wherein the first compartment is maintained at a temperature less than or equal to 0° C., and the second compartment is maintained at a temperature above 0° C.

56. Apparatus as set forth in claim 55 wherein said heat transfer liquid is water, and said phase change material is ice.

57. Apparatus for adjusting the body temperature of a patient, said apparatus comprising
an enclosure defining an interior space for receiving a portion of a patient's body, and
a liquid delivery system for driving heat transfer liquid into said interior space of the enclosure for direct liquid contact with the portion of the patient's body received therein to promote heat transfer between the patient's body and the heat transfer liquid, at least a portion of said liquid delivery system being in direct fluid communication with the heat transfer liquid after it has contacted the portion of the patient's body, said portion of the liquid delivery system being disposable, the liquid delivery system comprising a pump for transferring a heat transfer liquid and a disposable fluid reservoir, said reservoir comprising a first compartment for holding the phase change material and a second compartment for holding the heat transfer liquid, said compartments being arranged such that the phase change material alters the temperature of the heat transfer liquid.

58. Apparatus as set forth in claim 57 wherein the pump includes a detachable pumphead, the pumphead being disposable.

59. Apparatus as set forth in claim 58 wherein the pump is a gear pump.

60. Apparatus as set forth in claim 58 wherein the pump is a roller pump.

61. A method for adjusting the body temperature of a patient, said method comprising:
substantially enclosing at least a portion of a patient's body within an interior space of an enclosure, said enclosure having an inlet for receiving heat transfer liquid into said interior space to flow over the patient's body in direct liquid contact therewith to promote heat transfer between the patient's body and said heat transfer liquid, and an outlet in fluid communication with the interior space of the enclosure for exhausting said heat transfer liquid from the enclosure;

directing said heat transfer liquid through the inlet of the enclosure into the interior space to the outlet of the enclosure; and simultaneous with the directing heat transfer liquid step administering to the patient at least one therapy selected from a group of therapies including iced saline infusion, cardiopulmonary bypass, veno-veno bypass, intravascular cooling catheters, temperature-controlled ventilation, intravascular infusion of a slurry of ice and saline, and intrapulmonary infusion of a slurry of ice and saline.

62. Apparatus for adjusting the body temperature of a patient, said apparatus comprising:

an enclosure defining an interior space for receiving at least a torso of a patient's body;

a heat transfer liquid for transferring into the interior space for direct liquid contact with the patient's torso to promote heat transfer between the patient and said heat transfer liquid, the volume of the heat transfer liquid being less than about 30 liters, the enclosure comprising an outer layer and a porous inner fluid transfer layer engageable with the portion of the patient's body for carrying said heat transfer liquid, said transfer layer being formed from a substantially hydrophobic material; wherein the fluid transfer layer comprises a matrix of fibers.

63. Apparatus as set forth in claim 62 wherein the volume of heat transfer liquid is less than about 16 liters.

64. Apparatus as set forth in claim 62 wherein the enclosure includes an inlet and an outlet, and the fluid transfer layer being arranged for transporting heat transfer liquid from the inlet to the outlet.

65. Apparatus as set forth in claim 64 further comprising a liquid delivery system for driving heat transfer liquid into the enclosure through the inlet, through the fluid transfer layer, and out of the outlet.

66. Apparatus as set forth in claim 65 wherein the liquid delivery system drives said heat transfer liquid into the interior space of the enclosure at a flow rate between about 0.25 liters per minute (0.06 gallons per minute) and about 10.0 liters per minute (2.75 gallons per minute).

67. Apparatus as set forth in claim 62 wherein the enclosure is adapted to substantially seal the portion of the patient's torso in the interior space of the enclosure.

68. Apparatus as set forth in claim 62 wherein said enclosure is constructed to receive a portion of the patient from the neck downward.

69. Apparatus for adjusting the body temperature of a patient comprising an enclosure sized and shaped for receiving at least a majority of the body surface area, and a liquid delivery system adapted to connect to the enclosure for driving heat transfer liquid through the enclosure, the enclosure and liquid delivery system being sized to operate on less than 30 liters of heat transfer liquid, the liquid delivery system further comprising a heat exchanger for maintaining the temperature of the heat transfer liquid being driven into the enclosure between about 0° C. and about 5° C.

70. A method of reducing the temperature of a patient comprising:

enclosing a majority of the patient's body surface area in an enclosure; and driving a cooling liquid having a temperature between about 0° C. and about 5° C. into the enclosure at a rate greater than about 5 liters a minute for direct fluid contact with the patient's body surface area enclosed in the enclosure.

71. The method as set forth in claim 70 wherein the step of driving a cooling liquid includes circulating a total volume of cooling liquid that is less than about 30 liters.

72. The method as set forth in claim 70 further comprising monitoring the core body temperature of the patient, and discontinuing the driving of a cooling liquid when the patient's core body temperature reaches between about 32° C. and about 34° C.

* * * * *